(12) United States Patent
Lardizabal et al.

(10) Patent No.: US 7,741,532 B2
(45) Date of Patent: *Jun. 22, 2010

(54) DIACYLGLYCEROL ACYL TRANSFERASE PROTEINS

(75) Inventors: Kathryn Dennis Lardizabal, Woodland, CA (US); Gregory A. Thompson, Clarkston, WA (US); Deborah Hawkins, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/181,149

(22) Filed: Jul. 28, 2008

(65) Prior Publication Data

US 2009/0151027 A1      Jun. 11, 2009

Related U.S. Application Data

(63) Continuation of application No. 11/528,485, filed on Sep. 27, 2006, which is a continuation of application No. 10/208,018, filed on Jul. 31, 2002, now Pat. No. 7,135,617, which is a continuation-in-part of application No. 10/121,857, filed on Apr. 15, 2002, now Pat. No. 6,822,141, which is a continuation of application No. 09/345,461, filed on Jun. 30, 1999, now abandoned.

(60) Provisional application No. 60/091,631, filed on Jul. 2, 1998, provisional application No. 60/130,829, filed on Apr. 23, 1999.

(51) Int. Cl.
| | |
|---|---|
| C12N 15/31 | (2006.01) |
| C12N 15/52 | (2006.01) |
| C12N 15/82 | (2006.01) |
| A01H 5/00 | (2006.01) |

(52) U.S. Cl. .................. 800/281; 800/288; 800/312; 800/314; 800/320.1; 800/322; 435/183; 435/320.1; 435/419; 536/23.1; 536/23.2; 536/23.7

(58) Field of Classification Search ................. None
See application file for complete search history.

(56) References Cited

U.S. PATENT DOCUMENTS

| | | | | |
|---|---|---|---|---|
| 5,880,334 | A | 3/1999 | Suzuki et al. | 800/298 |
| 6,051,755 | A | 4/2000 | Zou et al. | 800/281 |
| 6,100,077 | A | 8/2000 | Sturley et al. | 435/193 |
| 6,344,548 | B1 | 2/2002 | Farese et al. | 536/23.2 |
| 6,444,876 | B1 | 9/2002 | Lassner et al. | 800/281 |
| 6,822,141 | B2 * | 11/2004 | Lardizabal et al. | 800/281 |
| 7,041,872 | B2 | 5/2006 | Lassner et al. | 800/281 |
| 7,355,097 | B2 | 4/2008 | Zou et al. | 800/278 |
| 7,417,176 | B2 | 8/2008 | Lardizabal et al. | 800/281 |
| 2005/0193446 | A1 | 9/2005 | Zou et al. | 800/281 |

FOREIGN PATENT DOCUMENTS

| | | |
|---|---|---|
| WO | WO 98/55631 | 6/1998 |
| WO | WO 00/01713 | 6/1999 |

OTHER PUBLICATIONS

Anderson et al., "Purification of diacylglycerol: acyltransferase from rat liver to near homegeneity", *Journal of Lipid Research*, Abstract, 35:535-545, 1994.
Bell, et al., "Enzymes of glycerolipid synthesis in eukaryotes," *Annu. Rev. Biochem.*, 49:459-487, 1980.
Blum et al., "Improved silver staining of plant proteins, RNA and DNA in polyacrylamide gels," *Electrophoresis*, 8:93-99, 1987.
Bouvier-Nave et al., "Expression in yeast and tobacco of plant cDNAs encoding acyl coA: diacylglycerol acyltransferase," *Eur. J. Biochem.*, 267:85-96, 2000.
Bradford, "A rapid and sensitive method for the quantitation of microgram quantities of protein utilizing the principle of protein-dye binding," *Anal. Biochem.*, 72:248, 1976.
Brindley, "Metabolism of triacylglycerols," In: *Biochemistry of Lipids, Lipoproteins and Membranes*, Vance et al. (eds.), Elsevier, Amsterdam, pp. 171-203, 1991.
Broun et al., "Cataytic plasticity of fatty acid modification enzymes underlying chemical diversity of plant lipids," *Science*, 283:1315-1317, 1998.
Cases et al., "Identification of a gene encoding an acyl CoA: diacylclycerol acyltransferase, a key enzyme in triacylglycerol synthesis", *Proc. Natl. Acad. Sci. USA*, Abstract, 95(22):13018-13023, 1998.
Coleman et al., "Physiological and nutritional regulation of enzymes of triacylglycerol synthesis," *Annu. Rev. Nutr*, 20:77-103, 2000.
Dahlqvist et al., Phospholipid: diacylglycerol acyltransferase: an enzyme that catalyzes the acyl-CoA-independent formation of triacylglycerol in yeast and plants, *Proc. Natl. Acad. Sci. USA*, 97:6487-6492, 2000.
Dahlqvist et al., "Selective channelling of unusual fatty acids into triacylglycerols," In: *Advances in Plant Lipid Research*, Sanches, et al. (Eds.), Universidad de Sevilla, Seville, Spain, pp. 211-214, 1998.
Daum et al., "Biochemistry, cell biology and molecular biology of lipids of *Saccharomyces cerevisiae,*" *Yeast*, 14:1471-1510, 1998.
Delepelaire et al., "Lithium dodecyl sulfate/polyacrylamide gel electrophoresis of thylakoid membranes at 4° C.: characterizations of two additional chlorophyll a-protein complexes," *Proc. Natl. Acad. Sci. USA*, 76:111-115, 1979.

(Continued)

*Primary Examiner*—Russell Kallis
(74) *Attorney, Agent, or Firm*—Chunping Li, Esq.; Sonnenschein Nath & Rosenthal LLP

(57) ABSTRACT

The invention provides diacylglycerol acyltransferase (DAGAT) proteins, wherein said proteins are active in the formation of triacylglycerol from fatty acyl and diacylglycerol substrates. In one aspect, *Mortierella ramanniana* DAGAT proteins have been isolated and have molecular weights of between approximately 36 and 37 kDa as measured by SDS-PAGE. The invention also provides novel DAGAT polynucleotide and polypeptide sequences and to methods of producing such polypeptides using recombinant techniques. In addition, methods are provided for using such sequences to alter triacylglycerol levels in plants and to treat diseases associated with altered DAGAT activity or expression.

21 Claims, 29 Drawing Sheets

OTHER PUBLICATIONS

EMBL Accession No. AA822348, Abstract, Feb. 1998.
EMBL Accession No. AA880703, Abstract, Mar. 1998.
EMBL Accession No. AA880955, Abstract, Mar. 1998.
EMBL Accession No. AT83514, Abstract, Aug. 1995.
EMBL Accession No. CEAF3384, Abstract, May 1997.
EMBL Accession No. HS84166, Abstract, Jul. 1995.
EMBL Accession No. SCYOR245c, Abstract, Jul. 1996.
Harwood, "Recent advances in the biosynthesis of plant fatty acids," *Biochim. Biophys Acta*, 1301:7-56, 1996.
Hobbs et al., "Cloning of a cDNA encoding diacylglycerol acyltransferase from *Arabidopsis thaliana* and its functional expression," *FEBS Letters*, 452:145-149, 1999.
Jako et al., "Seed-specific over-expression of an *Arabidopsis* cDNA encoding a diacylglycerol acyltransferase enhances seed oil content and seed weight," *Plant Physiology*, 126:861-874, 2001.
Jones et al., "Palmitoyl-acyl carrier protein (ACP) thioesterase and the evolutionary origin of plant acyl-ACP thioesterases," *The Plant Cell*, 7:359-371, 1995.
Kamisaka et al., "Activation of detergent-solubilized diacylglycerol acyltransferase by anionic phospholipids," *J. Biochem.*, 119:520-523, 1996.
Kamisaka et al., "Characterization of the diacylglycerol acyltransferase activity in the membrane fraction from a fungus," *Lipids*, 28:583-587, 1993.
Kamisaka et al., "Purification and characterization of diacylglycerol acyltransferase from the lipid body fraction of an oleaginous fungus," *Journal of Biochemistry*, Abstract, 6(121):1107-1114, 1907.
Kamisaka et al., "Purification and characterization of diacylglycerol acyltransferase from the lipid body fraction of an oleaginous fungus," *J. Biochem.*, 121:1107-1114, 1997.
Katavic et al., "Alteration of seed fatty acid composition by an ethyl methanesulfonate-induced mutation in *Arabidopsis thaliana* affecting diacylglycerol acyltranferase activity," *Plant Physiol*, 108:399-409, 1995.
Knutzon et al., "Modification of brassica seed oil by antisense expression of a stearoyl-acyl carrier protein desaturase gene," *Proc. Natl. Acad. Sci. USA*, 89:2624-2628, 1992.
Kwanyuen et al., "Isolation and purification of diacylglycerol acyltransferase from germinating soybean cotyledons," *BBA—Lipids and Lipid Metabolism, Elsevier Science*, 877:238-245, 1986.
Laemmli, "Cleavage of structural proteins during the assembly of the head of bacteriophage T4," *Nature*, 277:680-685, 1970.
Lardizabal et al., "Purification of a jojoba embryo wax synthase, cloning of its cDNA, and production of high levels of wax in seeds of transgenic arabidopsis," *Plant Physiol.*, 122:645-655, 2000.
Lewin et al., "Analysis of amino acid motifs diagnostic for the sn-glycerol-3-phosphate acyltransferase reaction," *Biochemistry*, 38:5764-5771, 1999.
Little et al., "Solubilization and characterization of diacylglycerol acyltransferase from microspore-derived cultures of oilseed rape," *Biochemical Journal*, 304:951-958, 1994.
Metz et al., "Purification of a jojoba embryo fatty acyl-coenzyme a reductase and expression of its cDNA in high erucic acid rapeseed," *Plant Physiol.*, 122:635-644, 2000.
Neuwald, "Barth syndrome may be due to an acyltransferase deficiency," *Current Biology*, 7:465-466, 1997.
Nishizuka, "Intracellular signaling by hydrolysis of phospholipids and activation of protein kinase C," *Science*, 258:607-614, 1992.
Oelkers et al., "A lecithin cholesterol acyltransferase-like gene mediates diacylglycerol esterification in Yeast," *J. Biol. Chem.*, 275:15609-15612, 2000.
Ohlrogge et al., "Fatty acid syntesis: from Co2 to functional genomics," *Biochemical Society Transactions*, 28(6):567-573, 2000.
Roesler et al., "Targeting of the arabidopsis homomeric acetyl-coenzyme a carboxylase to plastids of rapeseeds," *Plant Physiol.*, 113:75-81, 1997.
Routaboul et al., "The TAG1 locus of arabidopsis encodes for a diacylglycerol acyltransferase," *Plant Physiol. Biochem.*, 37:831-840, 1999.
Smith et al., "Obesity resistance and multiple mechanisms of triglyceride synthesis in mice lacking Dgat," *Nature Genetics*, 25:87-90, 2000.
Sorger et al., "Synthesis of triacylglycerols by the acyl-coenzyme A:diacyl-glycerol acyltransferase Dga1p in lipid particles of the yeast *Saccharomyces cerevisiae* ," *J. of Bacteriology*, 184(2):519-524, 2002.
Stobart et al., "Triacylglycerols are synthesized and utilized by transacylation reactions in microsomal preparations of developing safflower (*Carthamus tictorius* L.) seeds," *Planta*, 203:58-66, 1997.
Voelker et al., "Fatty acid biosynthesis redirected to medium chains in transgenic oilseed plants," *Science*, 257:72-74, 1992.
Waterhouse et al., "Virus resistance and gene silencing: killing the messenger," *Trends in Plant Sciences*, 4(11):452-457, 1999.
Zou et al., "The *Arabidopsis thaliana* TAG1 mutant has a mutation in a diacylglycerol acyltransferase gene," *The Plant Journal*, 19: 645-653, 1999.
Broun et al., "Accumulation of ricinoleic, lesquerolic, and densipolic acids in seeds of transgenic arabidopsis plants that express a fatty acyl hydroxylase cDNA from castor bean," *Plant Physiol.*, 113:933-942, 1997.

\* cited by examiner

Tandem Yellow 86-Agarose / Hydroxylapatite Chromatography

Figure 13

```
       1                                                           60
MR1    MASKDQHLQQKVKHTLEAIPSPRYAPLR-VPLRRRLQTLAVLLWCSMMSICMFIFFFLCS
MR2    .....MEQVQVTALLDHIPKVHWAPLRGIPLKRRLQTSAIVTWLALLPICLIIYLYLFT 61                                                          120
MR1    IPVLLWFPIILYLTWILVWDKAPENGGRPIRWLRNAAWWKLFAGYFPAHVIKEADLDPSK
MR2    IP-LLWPILIMYTIW-LFFDKAPENGGRRISLVRKLPLWKHFANYFPVTLIKEGDLDPKG 121                                                         180
MR1    NYIFGYHPHGIISMGSFCTFSTNATGFDDLFPGIRPSLLTLTSNFNIPLYRDYLMACGLC
MR2    NYIMSYHPHGIISMAAFANFATEATGFSEQYPGIVPSLLTLASNFRLPLYRDFMMSLGMC 181                                                         240
MR1    SVSKTSCQNILTKGGPGRSIAIVVGGASESLNARPGVMDLVLKRRFGFIKIAVQTGASLV
MR2    SVSRHSCEAIL-RSGPGRSIVIVTGGASESLSARPGTNDLTLKKRLGFIRLAIRNGASLV 241                                                         300
MR1    PTISFGENELYEQIESNENSKLHRWQKKIQHALGFTMPLFHGRGVFNYDFGLLPHRHPIY
MR2    PIFSFGENDIYEQYDNKKGSLIWRYQKWFQKITGFTVPLAHARGIFNYNAG.........

301                            357
MR1    TIVGKPIPVPSIKYGQTKDEIIRELHDSYMHAVQDLYDRYKDIYAKDRVKELEFVE.
MR2    ..........................................................
```

Figure 19

Figure 25
Field Grown
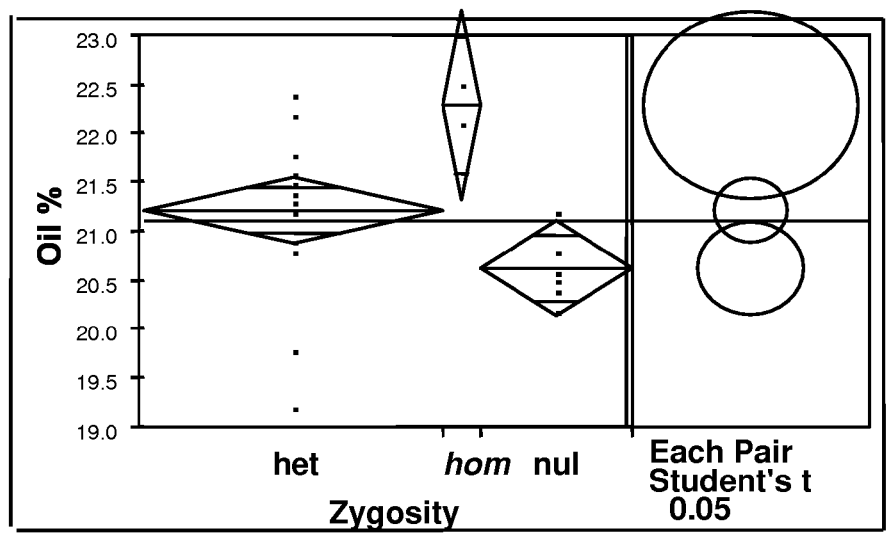
pCGN 8832 R2 seed oil/protein data - Jerseyville, IL
Event 13414
Oil (%) By Zygosity
+ 1.7% Oil
Greenhouse Grown
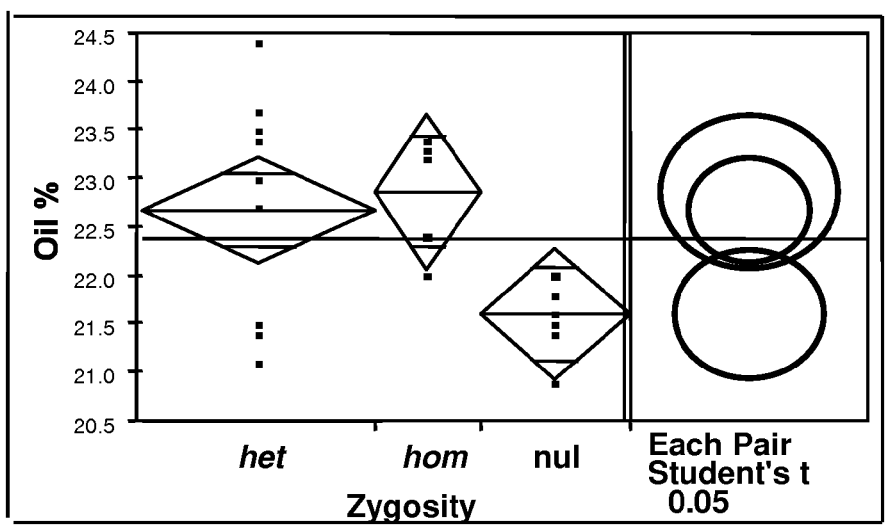
pCGN 8832 R2 seed oil/protein content - Chesterfield, MO
Event 13414 by class
Oil (%) By Class
+ 1.3% Oil

Figure 26
Field Grown
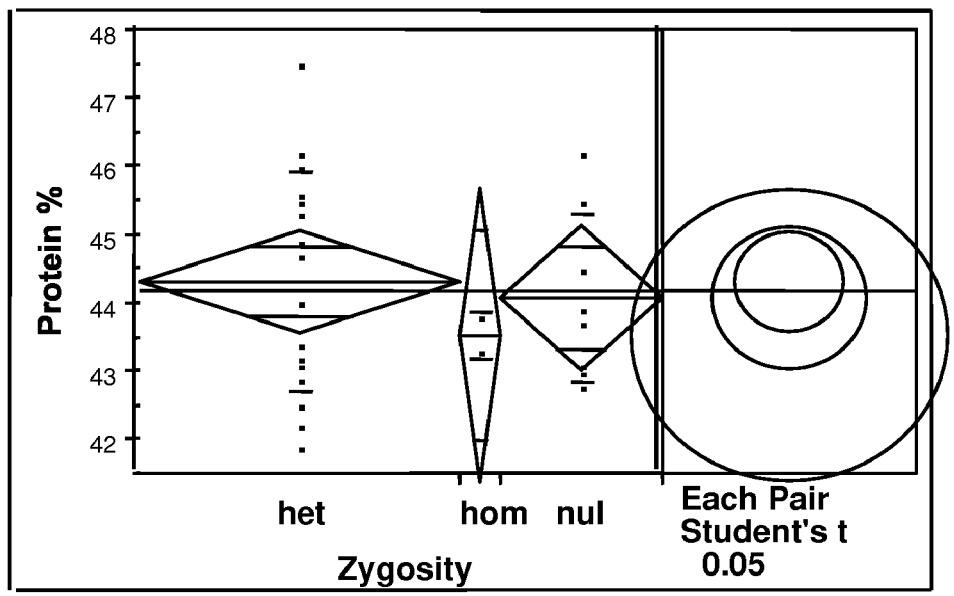
pCGN 8832 R2 seed oil/protein data - Jerseyville, IL
Event 13414
Oil (%) By Zygosity
Greenhouse Grown
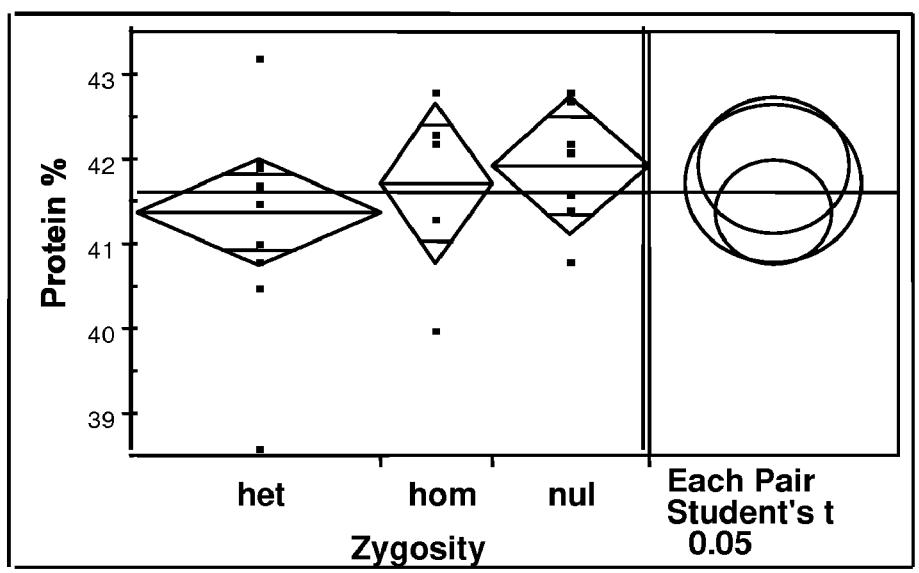
pCGN 8832 R2 seed oil/protein content - Chesterfield, MO
Event 13414 by class
Oil (%) By Class

SEQUENCE LISTING

<160> NUMBER OF SEQ ID NOS: 127

<210> SEQ ID NO 1
<211> LENGTH: 10
<212> TYPE: PRT
<213> ORGANISM: Mortierella ramanniana

<400> SEQUENCE: 1

Glu Leu His Asp Ser Tyr Met His Ala Val
1               5                   10

```
<210> SEQ ID NO 2
<211> LENGTH: 16
<212> TYPE: PRT
<213> ORGANISM: Mortierella ramanniana

<400> SEQUENCE: 2

Lys Ile Gln His Ala Leu Gly Phe Thr Met Pro Leu Phe His Gly Arg
 1               5                  10                  15

<210> SEQ ID NO 3
<211> LENGTH: 7
<212> TYPE: PRT
<213> ORGANISM: Mortierella ramanniana

<400> SEQUENCE: 3

His Pro Ile Tyr Thr Ile Val
 1               5

<210> SEQ ID NO 4
<211> LENGTH: 6
<212> TYPE: PRT
<213> ORGANISM: Mortierella ramanniana

<400> SEQUENCE: 4

Asn Ala Ala Trp Pro Lys
 1               5

<210> SEQ ID NO 5
<211> LENGTH: 8
<212> TYPE: PRT
<213> ORGANISM: Mortierella ramanniana

<400> SEQUENCE: 5

Val Lys Glu Leu Glu Phe Val Glu
 1               5

<210> SEQ ID NO 6
<211> LENGTH: 3
<212> TYPE: PRT
<213> ORGANISM: Mortierella ramanniana

<400> SEQUENCE: 6

Phe Gly Phe
 1

<210> SEQ ID NO 7
<211> LENGTH: 11
<212> TYPE: PRT
<213> ORGANISM: Mortierella ramanniana
<220> FEATURE:
<221> NAME/KEY: unsure
<222> LOCATION: (1)..(11)
<223> OTHER INFORMATION: unsure at all Xaa locations

<400> SEQUENCE: 7

Tyr Xaa His Asp Ala Tyr Pro His Ala Val Glu
 1               5                  10

<210> SEQ ID NO 8
<211> LENGTH: 16
<212> TYPE: PRT
<213> ORGANISM: Mortierella ramanniana

<400> SEQUENCE: 8

Glu Leu His Asp Ser Tyr Met His Ala Val Gln Asp Leu Tyr Asp Arg
 1               5                  10                  15
```

-continued

<210> SEQ ID NO 9
<211> LENGTH: 13
<212> TYPE: PRT
<213> ORGANISM: Mortierella ramanniana

<400> SEQUENCE: 9

Gly Val Phe Asn Tyr Asp Phe Gly Leu Leu Pro His Arg
1 5 10

<210> SEQ ID NO 10
<211> LENGTH: 8
<212> TYPE: PRT
<213> ORGANISM: Mortierella ramanniana
<220> FEATURE:
<221> NAME/KEY: unsure
<222> LOCATION: (1)..(8)
<223> OTHER INFORMATION: unsure at all Xaa locations

<400> SEQUENCE: 10

Xaa Leu Ala Gly Ile Phe Pro Ala
1 5

<210> SEQ ID NO 11
<211> LENGTH: 15
<212> TYPE: PRT
<213> ORGANISM: Mortierella ramanniana

<400> SEQUENCE: 11

Ile Ala Val Gln Thr Gly Ala Gly Leu Val Pro Thr Leu Ser Phe
1 5 10 15

<210> SEQ ID NO 12
<211> LENGTH: 15
<212> TYPE: PRT
<213> ORGANISM: Mortierella ramanniana

<400> SEQUENCE: 12

Ser Ile Ala Ile Val Val Gly Ser Ala Ser Glu Ser Ile Asn Ala
1 5 10 15

<210> SEQ ID NO 13
<211> LENGTH: 10
<212> TYPE: PRT
<213> ORGANISM: Mortierella ramanniana
<220> FEATURE:
<221> NAME/KEY: unsure
<222> LOCATION: (1)..(10)
<223> OTHER INFORMATION: unsure at all Xaa locations

<400> SEQUENCE: 13

Gly Phe Phe Asn Tyr Asp Phe Xaa Xaa Leu
1 5 10

<210> SEQ ID NO 14
<211> LENGTH: 10
<212> TYPE: PRT
<213> ORGANISM: Mortierella ramanniana

<400> SEQUENCE: 14

Glu Leu His Asp Ser Tyr Met His Ala Val
1 5 10

<210> SEQ ID NO 15
<211> LENGTH: 7
<212> TYPE: PRT

```
<213> ORGANISM: Mortierella ramanniana

<400> SEQUENCE: 15

Val His Trp Ala Pro Leu Arg
  1               5

<210> SEQ ID NO 16
<211> LENGTH: 6
<212> TYPE: PRT
<213> ORGANISM: Mortierella ramanniana

<400> SEQUENCE: 16

Lys Leu Pro Leu Phe Lys
  1               5

<210> SEQ ID NO 17
<211> LENGTH: 9
<212> TYPE: PRT
<213> ORGANISM: Mortierella ramanniana
<220> FEATURE:
<221> NAME/KEY: unsure
<222> LOCATION: (1)..(9)
<223> OTHER INFORMATION: unsure at all Xaa locations

<400> SEQUENCE: 17

Val Asp Leu Asp Xaa Ala Pro Pro Arg
  1               5

<210> SEQ ID NO 18
<211> LENGTH: 10
<212> TYPE: PRT
<213> ORGANISM: Mortierella ramanniana

<400> SEQUENCE: 18

Ile Thr Gly Phe Thr Val Pro His Ala His
  1               5                  10

<210> SEQ ID NO 19
<211> LENGTH: 10
<212> TYPE: PRT
<213> ORGANISM: Mortierella ramanniana
<220> FEATURE:
<221> NAME/KEY: unsure
<222> LOCATION: (1)..(10)
<223> OTHER INFORMATION: unsure at all Xaa locations

<400> SEQUENCE: 19

Glu Leu His Asp Ser His Met Leu Xaa Val
  1               5                  10

<210> SEQ ID NO 20
<211> LENGTH: 13
<212> TYPE: PRT
<213> ORGANISM: Mortierella ramanniana

<400> SEQUENCE: 20

Gly Ile Phe Asn Tyr Asn Ala Gly Phe Ile Pro Phe Arg
  1               5                  10

<210> SEQ ID NO 21
<211> LENGTH: 13
<212> TYPE: PRT
<213> ORGANISM: Mortierella ramanniana

<400> SEQUENCE: 21

His Pro Ile Tyr Thr Ile Val Gly Lys Pro Ile Pro Val
```

<210> SEQ ID NO 22
<211> LENGTH: 8
<212> TYPE: PRT
<213> ORGANISM: Mortierella ramanniana

<400> SEQUENCE: 22

Gly Ser Cys Glu Ala Ile Leu Arg
 1               5

<210> SEQ ID NO 23
<211> LENGTH: 26
<212> TYPE: PRT
<213> ORGANISM: Mortierella ramanniana

<400> SEQUENCE: 23

His Pro Ile Val Thr Val Val Gly Lys Pro Ile Ala Val Pro Leu Leu
 1               5                  10                  15

Ala Glu Gly Glu Thr Glu Pro Pro Ser Glu
            20                  25

<210> SEQ ID NO 24
<211> LENGTH: 29
<212> TYPE: PRT
<213> ORGANISM: Mortierella ramanniana

<400> SEQUENCE: 24

Ser Arg Asp Ser Thr Pro Val Ile Thr Glu His Lys Gln Pro Met Glu
 1               5                  10                  15

Gln Val Gln Val Thr Ala Leu Leu Asp His Ile Pro Val
            20                  25

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: degenerate
      primer for peptide in SEQ ID NO: 5
<220> FEATURE:
<221> NAME/KEY: unsure
<222> LOCATION: (1)..(28)
<223> OTHER INFORMATION: unsure at all n locations

<400> SEQUENCE: 25
cactgcagac raaytcnary tcyttnac                                      28

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Degenerate
      primer to SEQ ID NO: 9
<220> FEATURE:
<221> NAME/KEY: unsure
<222> LOCATION: (1)..(30)
<223> OTHER INFORMATION: unsure at all n locations

<400> SEQUENCE: 26
ccaagcttgg ngtnttyaay taygayttyg                                    30

<210> SEQ ID NO 27
<211> LENGTH: 30
<212> TYPE: DNA

```
<213> ORGANISM: Artificial Sequence
<220> FEATURE:
<223> OTHER INFORMATION: Description of Artificial Sequence: degenerate
      primer to SEQ ID NO: 9
<220> FEATURE:
<221> NAME/KEY: unsure
<222> LOCATION: (1)..(30)
<223> OTHER INFORMATION: unsure at all n locations

<400> SEQUENCE: 27
cactgcagcr aartcrtart traanacncc                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: degenerate
      primer to SEQ ID NO: 8
<220> FEATURE:
<221> NAME/KEY: unsure
<222> LOCATION: (1)..(30)
<223> OTHER INFORMATION: unsure at all n locations

<400> SEQUENCE: 28
cactgcagcy tgnacngcng crtgcatrta                                    30

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 11
<220> FEATURE:
<221> NAME/KEY: unsure
<222> LOCATION: (1)..(28)
<223> OTHER INFORMATION: unsure at all n locations

<400> SEQUENCE: 29
ccaagcttat hgcngtncar acnggngc                                      28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 3
<220> FEATURE:
<221> NAME/KEY: unsure
<222> LOCATION: (1)..(28)
<223> OTHER INFORMATION: unsure at all n locations

<400> SEQUENCE: 30
ccaagcttaa rcayccnath tayacnat                                      28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 3
<220> FEATURE:
<221> NAME/KEY: unsure
<222> LOCATION: (1)..(28)
<223> OTHER INFORMATION: unsure at all n locations

<400> SEQUENCE: 31
```

```
cactgcagac datngtrtad atnggrtg                                          28
```

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 2
<220> FEATURE:
<221> NAME/KEY: unsure
<222> LOCATION: (1)..(28)
<223> OTHER INFORMATION: unsure at all n locations

<400> SEQUENCE: 32

```
ccaagcttgc nytnggntty acnatgcc                                          28
```

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 2
<220> FEATURE:
<221> NAME/KEY: unsure
<222> LOCATION: (1)..(28)
<223> OTHER INFORMATION: unsure at all n locations

<400> SEQUENCE: 33

```
ccaagctttt yacnatgccn ytnttyca                                          28
```

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 2
<220> FEATURE:
<221> NAME/KEY: unsure
<222> LOCATION: (1)..(28)
<223> OTHER INFORMATION: unsure at all n locations

<400> SEQUENCE: 34

```
cactgcagaa rtgraanarn ggcatngt                                          28
```

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: RACE PCR
      primer for MR1

<400> SEQUENCE: 35

```
ggtttgctcc cccatcgcca tcctatc                                           27
```

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: RACE PCR
      primer for MR1

<400> SEQUENCE: 36

```
gataggatgg cgatggggga gcaaacc                                           27
```

<210> SEQ ID NO 37
<211> LENGTH: 1065
<212> TYPE: DNA
<213> ORGANISM: Mortierella ramanniana

<400> SEQUENCE: 37

```
atggccagca aggatcaaca tttacagcag aaggtcaagc atacgctaga agctatccca    60
tcccctcgct atgctccatt gcgagtgcca ttaagacgga gattacaaac attggcagta   120
tttattatgg tgttccatga tgtcaatatg catgtcatat tcttctttt atgctcattc    180
ctgttctcct ttggttccca ttatctttat ttgacctgga tcttggtgtg ggataaggcg   240
ccagagaacg gtggaagacc tattcgctgc ctgcggaatg ctgcttggtg aagctgttt    300
gcagggtatt ttcccgcaca tatcatcaag gaagccgatt tagatccatc caagaacaca   360
atctttggtt atcaccccca tggaatcata tccatgggct cgttctgtac ttttaagtcc   420
aatgctactg gctttgatga cttgttccca ggcatccggc atcgctttt gacattaaca    480
tctaatttta atatcccact ttatcgtgat tatttgatgg cgtgcggact ttgctccgtc   540
tccaaaacat cctgtcaaaa tattttaacc aaaggtggtc cgggccgttc cattgccatt   600
gtcgtgggag gtgcttccga gtctctcaat gctagacccg tgtcatgga ccttgtgttg    660
aagagacgct ttggttttat caagattgct gttcaaaccg tgcaagtct agtgcccact    720
atcagttttg gtgaaaatga gctgtacgaa cagattgaaa gcaatgaaaa ctcaaagttg   780
catagatggc aaaagaagat tcaacatgct cttggtttta ctatgccgct ctttcatgga   840
cgcggtgtat tcaattatga ctttggtttg ctcccccatc gccatcctat ctacacgatt   900
gttggaaagc ccatcccgt ccctagcatc aagtatggac agacaaagga tgagattata    960
agagaactac atgactcgta catgcatgcc gtgcaggatc tctatgatcg ttacaaggat  1020
atctatgcaa aggatcgggt aaaagaacta gaattcgtcg aatag                  1065
```

<210> SEQ ID NO 38
<211> LENGTH: 354
<212> TYPE: PRT
<213> ORGANISM: Mortierella ramanniana

<400> SEQUENCE: 38

```
Met Ala Ser Lys Asp Gln His Leu Gln Gln Lys Val Lys His Thr Leu
  1               5                  10                  15

Glu Ala Ile Pro Ser Pro Arg Tyr Ala Pro Leu Arg Val Pro Leu Arg
                 20                  25                  30

Arg Arg Leu Gln Thr Leu Ala Val Phe Ile Met Val Phe His Asp Val
             35                  40                  45

Asn Met His Val Ile Phe Phe Phe Leu Cys Ser Phe Leu Phe Ser Phe
         50                  55                  60

Gly Ser His Tyr Leu Tyr Leu Thr Trp Ile Leu Val Trp Asp Lys Ala
 65                  70                  75                  80

Pro Glu Asn Gly Gly Arg Pro Ile Arg Cys Leu Arg Asn Ala Ala Trp
                 85                  90                  95

Trp Lys Leu Phe Ala Gly Tyr Phe Pro Ala His Ile Ile Lys Glu Ala
            100                 105                 110

Asp Leu Asp Pro Ser Lys Asn Thr Ile Phe Gly Tyr His Pro His Gly
        115                 120                 125

Ile Ile Ser Met Gly Ser Phe Cys Thr Phe Lys Ser Asn Ala Thr Gly
    130                 135                 140
```

```
Phe Asp Asp Leu Phe Pro Gly Ile Arg Pro Ser Leu Leu Thr Leu Thr
145                 150                 155                 160

Ser Asn Phe Asn Ile Pro Leu Tyr Arg Asp Tyr Leu Met Ala Cys Gly
                165                 170                 175

Leu Cys Ser Val Ser Lys Thr Ser Cys Gln Asn Ile Leu Thr Lys Gly
            180                 185                 190

Gly Pro Gly Arg Ser Ile Ala Ile Val Val Gly Gly Ala Ser Glu Ser
        195                 200                 205

Leu Asn Ala Arg Pro Gly Val Met Asp Leu Val Leu Lys Arg Arg Phe
    210                 215                 220

Gly Phe Ile Lys Ile Ala Val Gln Thr Gly Ala Ser Leu Val Pro Thr
225                 230                 235                 240

Ile Ser Phe Gly Glu Asn Glu Leu Tyr Glu Gln Ile Glu Ser Asn Glu
                245                 250                 255

Asn Ser Lys Leu His Arg Trp Gln Lys Lys Ile Gln His Ala Leu Gly
            260                 265                 270

Phe Thr Met Pro Leu Phe His Gly Arg Gly Val Phe Asn Tyr Asp Phe
        275                 280                 285

Gly Leu Leu Pro His Arg His Pro Ile Tyr Thr Ile Val Gly Lys Pro
290                 295                 300

Ile Pro Val Pro Ser Ile Lys Tyr Gly Gln Thr Lys Asp Glu Ile Ile
305                 310                 315                 320

Arg Glu Leu His Asp Ser Tyr Met His Ala Val Gln Asp Leu Tyr Asp
                325                 330                 335

Arg Tyr Lys Asp Ile Tyr Ala Lys Asp Arg Val Lys Glu Leu Glu Phe
            340                 345                 350

Val Glu

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Primer for
      amplification of MR1 coding sequence

<400> SEQUENCE: 39
aattcgcggc cgcatggcca gcaaggatca acatttacag c                        41

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Primer for
      amplification of MR1 coding sequence

<400> SEQUENCE: 40
tgctgcagct attcgacgaa ttctagttct tttacccgat cc                       42

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: degenerate
      primer for SEQ ID NO: 23
<220> FEATURE:
<221> NAME/KEY: unsure
<222> LOCATION: (1)..(23)
<223> OTHER INFORMATION: unsure at all n locations
```

<400> SEQUENCE: 41
ggcacngcda tnggyttncc nac                                                  23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: degenerate
      primer for SEQ ID NO: 20
<220> FEATURE:
<221> NAME/KEY: unsure
<222> LOCATION: (1)..(23)
<223> OTHER INFORMATION: unsure at all n locations

<400> SEQUENCE: 42
ccngcrttrt arttraadat ncc                                                  23

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: primer for
      5' RACE amplification of MR2

<400> SEQUENCE: 43
tgcctagtga catcatgaaa tctcg                                                25

<210> SEQ ID NO 44
<211> LENGTH: 845
<212> TYPE: DNA
<213> ORGANISM: Mortierella ramanniana

<400> SEQUENCE: 44
atggaacaag tccaagtcac tgcattgctc gaccacattc ccaaagtcca ttgggcaccg          60
ctccgcggga tcccttttgaa gcgtcgctta caaacgtcgg ctatcgtcac atggctggct        120
ttgcttccta tctgtctcat tatataccctg tacctattca ccattccctt attatggccc        180
atcctcatta tgtatacgat atggctgttt tcgacaaag cccctgaaaa cggaggcaga          240
cgaatttcgc tggtgaggaa attgccgctg tggaagcatt tgccaattaa tttcccagtc         300
actttgatca aggaaggaga cctcgacccc aagggaaact acatcatgtc atatcatccg         360
catggaataa tatccatggc ggcttttgcc aatttttgcga ctgaggcgac tgggttttcc       420
gagcaatatc cgggtattgt tccttcatta ctgacgctag catccaattt tcggttgcca        480
ttgtaccgag atttcatgat gtcactaggc atgtgctcgg tatcgcgaca ctcctgtgaa        540
gctatccttc gttcggggcc cggtcgatcc attgtgattg ttacaggcgg agcttcagaa        600
tcccttagcg cacgaccagg caccaacgac ctcaccctca gaaacgatt gggtttcatc         660
cgactagcca ttcgaaatgg tgccagttta gtgcctatct tttcgtttgg agagaacgac        720
atctacgagc aatatgataa caaaagggc agtttgatat ggcggtacca aaaatggttc        780
caaaaaatta caggattcac ggttcctttg gctcatgccc gtggaatytt caactacaac       840
gcggg                                                                    845

<210> SEQ ID NO 45
<211> LENGTH: 281
<212> TYPE: PRT
<213> ORGANISM: Mortierella ramanniana

<400> SEQUENCE: 45

Met Glu Gln Val Gln Val Thr Ala Leu Leu Asp His Ile Pro Lys Val
1               5                   10                  15

His Trp Ala Pro Leu Arg Gly Ile Pro Leu Lys Arg Arg Leu Gln Thr
            20                  25                  30

Ser Ala Ile Val Thr Trp Leu Ala Leu Leu Pro Ile Cys Leu Ile Ile
        35                  40                  45

Tyr Leu Tyr Leu Phe Thr Ile Pro Leu Leu Trp Pro Ile Leu Ile Met
    50                  55                  60

Tyr Thr Ile Trp Leu Phe Phe Asp Lys Ala Pro Glu Asn Gly Gly Arg
65                  70                  75                  80

Arg Ile Ser Leu Val Arg Lys Leu Pro Leu Trp Lys His Phe Ala Asn
                85                  90                  95

Tyr Phe Pro Val Thr Leu Ile Lys Glu Gly Asp Leu Asp Pro Lys Gly
            100                 105                 110

Asn Tyr Ile Met Ser Tyr His Pro His Gly Ile Ile Ser Met Ala Ala
        115                 120                 125

Phe Ala Asn Phe Ala Thr Glu Ala Thr Gly Phe Ser Glu Gln Tyr Pro
    130                 135                 140

Gly Ile Val Pro Ser Leu Leu Thr Leu Ala Ser Asn Phe Arg Leu Pro
145                 150                 155                 160

Leu Tyr Arg Asp Phe Met Met Ser Leu Gly Met Cys Ser Val Ser Arg
                165                 170                 175

His Ser Cys Glu Ala Ile Leu Arg Ser Gly Pro Gly Arg Ser Ile Val
            180                 185                 190

Ile Val Thr Gly Gly Ala Ser Glu Ser Leu Ser Ala Arg Pro Gly Thr
        195                 200                 205

Asn Asp Leu Thr Leu Lys Lys Arg Leu Gly Phe Ile Arg Leu Ala Ile
    210                 215                 220

Arg Asn Gly Ala Ser Leu Val Pro Ile Phe Ser Phe Gly Glu Asn Asp
225                 230                 235                 240

Ile Tyr Glu Gln Tyr Asp Asn Lys Lys Gly Ser Leu Ile Trp Arg Tyr
                245                 250                 255

Gln Lys Trp Phe Gln Lys Ile Thr Gly Phe Thr Val Pro Leu Ala His
            260                 265                 270

Ala Arg Gly Ile Phe Asn Tyr Asn Ala
        275                 280

<210> SEQ ID NO 46
<211> LENGTH: 355
<212> TYPE: DNA
<213> ORGANISM: Zea mays

<400> SEQUENCE: 46
tgcctaagac tggttgcttt tcttaaatca agaaaaggtt ttgtcaagat agctatacag      60
tctggatgtc ctttagtccc agttttctgc tttgggcaga gctatgcata caagtggtgg     120
aggcctggtg gtaaattgtt tatcaagatc gctagagcag ttaaatttac tcctattatc     180
ttctgggata gatttggcac accattcccc ttcccaaaac ccatgcatgt ggtcgtgggt     240
aaaccaattg aagtcaataa gattcccat cctacaattg acgagattaa tgaagtccat      300
ggacagttca tcattgccat gcgggacctc tttgagagct gtatcatcag tgtct          355

<210> SEQ ID NO 47
<211> LENGTH: 375

```
<212> TYPE: DNA
<213> ORGANISM: Zea mays

<400> SEQUENCE: 47
cccacgcgtc cgcgagctta tgtttttgct tatgaaccgc attcggtgct gcctattggc    60
gtttgtgcgc ttgcggatca tacaggtttt ttgcccctgc cgaagattaa ggctcttgcg   120
agtaccgcgg ttttctatgt gccgtttgtg aggcagatat ggacatggtt ggggcttgtc   180
cctgcgtcga gaaggaattt ttacgagtac ttggcggctg ggtatagttg catcatagtg   240
ccgggtggtg tgcaggagtt gttgtatatg gaatgtgatt cggaggttgc tttttcttaaa   300
tcaaggaaag gatttgtaaa gatagccatg gagatgggtc aacctcttgt acctgtattc   360
tgctttggtc agagt                                                    375

<210> SEQ ID NO 48
<211> LENGTH: 477
<212> TYPE: DNA
<213> ORGANISM: Brassica napus
<220> FEATURE:
<221> NAME/KEY: unsure
<222> LOCATION: (1)..(477)
<223> OTHER INFORMATION: unsure at all n locations

<400> SEQUENCE: 48
aacnttactt gccaggcacc ggtcaagaan tcccgggtcg acccacgcgt ccgcaaatac    60
ggtcgaatgc tcgctaggta catatgtaaa cacgcgtgta gttatttccc cgttactctc   120
catgtcgagg attacgaagc tttccagcct actcgtgcct atgttttttgg ttatgaacca   180
cattcggtgt ggcctattgg agctgttgca cttgctgatc ttacggggtt catgcctctt   240
cctaacatca aagttcttgc tagtactgct gttttctaca cacccttttct gaggcaaata   300
tggacgtggt tagggctcgc ccctgcttct aggaagaatt tcgcttccta tttggactct   360
ggctatagtt gtatcctcgt acctggtggt gtccaggaga catttcacat gaaacatgat   420
gttgagaact tattcctttc atccgagaan ggggtttgtg cgcatcgcca tgggagc      477

<210> SEQ ID NO 49
<211> LENGTH: 498
<212> TYPE: DNA
<213> ORGANISM: Glycine max
<220> FEATURE:
<221> NAME/KEY: unsure
<222> LOCATION: (1)..(498)
<223> OTHER INFORMATION: unsure at all n locations

<400> SEQUENCE: 49
nngcttccta tcaacgtgca gtgggatttg gccgaagatt gtcgaggttc atatgcaagc    60
acgcagtgca attactctcc gatcacgctt cacgtagagg atatgaaagc ctttgatcct   120
aaccgtgctt atgttttttgg gtatgaacca cattcagttt tgccaattgg catacgtnnt   180
gcattggctg accacacagg tttcatgcct cttccaaaag ttaaagttct tgctagcagc   240
acggtgttct acacaccatt ttacacacca tttttgagac acatatggac atggttgggt   300
ctaacgccag tgacaaagaa aaggtttacc tcgctgttgg atgctggcta tagttgtatc   360
ttgatacctg gtggagtgca agaagcattt tcattgagc atggtctga gattgccttt   420
cttaaatcaa ggagaggatt tgtccgcata gcaatggaga agggaaaacc cctggttcca   480
gttttctgct ttggtcag                                                 498

<210> SEQ ID NO 50
```

<211> LENGTH: 393
<212> TYPE: DNA
<213> ORGANISM: Arabidopsis thaliana
<220> FEATURE:
<221> NAME/KEY: unsure
<222> LOCATION: (1)..(393)
<223> OTHER INFORMATION: unsure at all n locations

<400> SEQUENCE: 50

| | |
|---|---|
| gcgtccgtcg ccatggccat ctggcttggc gccattcact tcaacgtcgc tcttgttctc | 60 |
| tgttctctca ttttccttcc tccttctcta tctctcatgg tcttgggctt gctctctctg | 120 |
| tttatcttta tcccaatcga tcatcgtagc aaatatggtc gtaagctcgc taggtacata | 180 |
| tgcaagcacg cgtgtaatta tttccccgtc tctctgtacg tcgaggatta cgaancttc | 240 |
| cagcctaatc gtgcctatgt ctttggttat gaaccacatt cggtgctacc gattggantt | 300 |
| gtngctcttt gtgatctcac anggtttatg cctaatccta acattaaagt tcttgcaant | 360 |
| agtgctaaat tcaaaattcc ctttcaaagg ata | 393 |

<210> SEQ ID NO 51
<211> LENGTH: 344
<212> TYPE: DNA
<213> ORGANISM: Arabidopsis thaliana
<220> FEATURE:
<221> NAME/KEY: unsure
<222> LOCATION: (1)..(344)
<223> OTHER INFORMATION: unsure at all n locations

<400> SEQUENCE: 51

| | |
|---|---|
| cttgccgtgc cggtccgaaa taacgggtcg acncacgcgt ccgtgtacgt cgaggattac | 60 |
| gaagctttcc agcctaatcg tgcctatgtc tttggttatg aaccacattc ggtgctaccg | 120 |
| attggagttg ttgctctttg tgatctcaca gggtttatgc cnattcctaa cattaaagtt | 180 |
| cttgcaagta gtgctatatt ctacactccc tttctaaggc atatatggac atggttaggg | 240 |
| ctcaccgctg cttctaggaa naatttcact tcccttttgg attctggcta cagttgtgtt | 300 |
| cttgtacctg gtgggtgtgc aggagacttt tcanatgcan catg | 344 |

<210> SEQ ID NO 52
<211> LENGTH: 462
<212> TYPE: DNA
<213> ORGANISM: Arabidopsis thaliana

<400> SEQUENCE: 52

| | |
|---|---|
| cgagagaagc acattttggg gtacgcacca catggtatgt cccgatgggc gcctcttat | 60 |
| ctccacaaca cctcgatgtg gatggaactc ttcccaaaca ttgtgcctta tacacttaca | 120 |
| gcgacggtga ctcatctggt tccgtttcta agagaagtga ctcagtataa cggaggtgtt | 180 |
| gaagtcagtc aaagtagttt tgcaaacgcg ttgatgaaat tcaaaaacgt tttgctggtc | 240 |
| cccggaggac aacatgaaat gttactcatc agcgacgacc ataacgaagt gcttttatcc | 300 |
| gccaaacaca agggattcat tcgattagcc ttgcaatcgg cagcagaaaa cccagatgaa | 360 |
| gtcatcaacc tcgtcccggt gtacgctttt ggagaaaaag acaaaatgta taacgcattc | 420 |
| cctgcgagtc tctctctgca gcgatatctg gtggccaagc tg | 462 |

<210> SEQ ID NO 53
<211> LENGTH: 489
<212> TYPE: DNA
<213> ORGANISM: Human
<220> FEATURE:
<221> NAME/KEY: unsure

```
<222> LOCATION: (1)..(489)
<223> OTHER INFORMATION: unsure at all n locations

<400> SEQUENCE: 53
cccagcccca gcttcgggca ggccgtggtc atcatggtgg ggggtgcgca cgaggccctg      60
tattcagtcc ccggggagca ctgccttacg ctccagaagc gcaaaggctt cgtgcgcctg     120
gcgctgaggc acgggcgtn cntggtgccc gtgtactcct ttggggagaa tgacatcttt     180
agacttaagg cttttgccac aggnncctgg cagnattggt gccagctcac cttcaagaag     240
ctcatgggct tntcnccttg catnttctgg ggtncggtn tcttctcagc cacntcntgg     300
ggcctgctgn nctttgctgt gcccatcacn actgtggtgg nnngnacnat nnccntnaan     360
cagaaccncc acccnaccga ggaggaaatn aatnactatn acgnnntcta catgacggnc     420
ntggagcagn tcttcgagga gnanaaggaa agntgtgggg accngcttc cacctgcntn     480 accttnatc                                                             489

<210> SEQ ID NO 54
<211> LENGTH: 333
<212> TYPE: DNA
<213> ORGANISM: Human

<400> SEQUENCE: 54
tggcccttct ctgtttttta cttggtgtgg ctctatgtgg actgggacac acccaaccaa      60
ggtggaaggc gttcggagtg gataaggaac cgggcaattt ggagacaact aagggattat     120
tatcctgtca agctggtgaa acagcagag ctgcccccgg atcggaacta cgtgctgggc     180
gcccaccctc atgggatcat gtgtacaggc ttcctctgta atttctccac cgagagcaat     240
ggcttctccc agctcttccc ggggctccgg ccctggttag ccgtgctggc tggcctcttc     300
tacctcccgg tctatcgcga ctacatcatg tcc                                  333

<210> SEQ ID NO 55
<211> LENGTH: 222
<212> TYPE: DNA
<213> ORGANISM: Human

<400> SEQUENCE: 55
atcattgtag ggggtgccca ggaggccctg gatgccaggc ctggatcctt cacgctgtta      60
ctgcggaacc gaaagggctt cgtcaggctc gccctgacac acggggcacc cctggtgcca     120
atcttctcct tcggggagaa tgacctattt gaccagattc caactcttc tggctcctgg     180 ttacgctata tccagaatcg gttgcagaag atcatgggca tc                        222

<210> SEQ ID NO 56
<211> LENGTH: 827
<212> TYPE: DNA
<213> ORGANISM: Human

<400> SEQUENCE: 56
ctccagtggg tcctgtcctt ccttgtactg ggagtggcct gcagtgccat cctcatgtac      60
atattctgca ctgattgctg gctcatcgct gtgctctact tcacttggct ggtgtttgac     120
tggaacacac ccaagaaagg tggcaggagg tcacagtggg tccgaaactg gctgtgtgg     180 cgctactttc gagactactt tcccatccag ctggtgaaga cacacaacct gctgaccacc     240
aggaactata tctttggata ccaccccat ggtatcatgg gcctgggtgc cttctgcaac     300
ttcagcacag aggccacaga agtgagcaag aagttcccag gcatacggcc ttacctggct     360
```

```
acactggcag gcaacttccg aatgcctgtg ttgagggagt acctgatgtc tggaggtatc    420
tgccctgtca gccgggacac catagactat ttgctttcaa agaatgggag tggcaatgct    480
atcatcatcg tggtcggggg tgcggctgag tctctgagct ccatgcctgg caagaatgca    540
gtcaccctgc ggaaccgcaa gggctttgtg aaactggccc tgcgtcatgg agctgacctg    600
gttcccatct actcctttgg agagaatgaa gtgtacaagc aggtgatctt cgaggagggc    660
tcctggggcc gatgggtcca gaagaagttc cagaaataca ttggtttcgc cccatgcatc    720
ttccatggtc gaggcctctt ctcctccgac acctgggggc tggtgcccta ctccaagccc    780
atcaccactg ttgtgggaga gcccatcacc atccccaagc tggagca                 827
```

```
<210> SEQ ID NO 57
<211> LENGTH: 265
<212> TYPE: DNA
<213> ORGANISM: Human
<220> FEATURE:
<221> NAME/KEY: unsure
<222> LOCATION: (1)..(265)
<223> OTHER INFORMATION: unsure at all n locations

<400> SEQUENCE: 57
agcgattatt tccctctcaa gcttctgaag actcatgaca tctgccccag ccgcaactac    60
atcctcgtct gccaccctca tgggctcttt gccatggat ggtttggcca ctttgccaca    120
gaggcctcag gcttctccaa gatatttccn ggcatcaccc cttacatact cacactggga    180 gccttttct ggatgccttt cctcagagaa tatgtaatgt ctacagggc ctgctctgtg    240 agtcgatcct ccattgactt tctgc                                          265
```

```
<210> SEQ ID NO 58
<211> LENGTH: 342
<212> TYPE: DNA
<213> ORGANISM: murine

<400> SEQUENCE: 58
ctmgtgcagg tgtgcattgg aattatggtg atgctggtcc tgtacaacta ttggttcctt    60
tacatcccat atctggtctg gttttactat gactggagaa ccccagagca aggaggcaga    120
agatggaact gggtccaaag ctggcctgtg tggaagtatt ttaaggagta ttttccaatc    180
tgtcttgtca aaacgcagga tttggatccg ggtcacaatt atatatttgg gtttcaccct    240
catggaatat tcgtgcctgg agcctttgga aattttgta caaaatactc ggacttcaag    300
aagctatttc ctggctttac atcgtatctc cacgtggcca ag                      342
```

```
<210> SEQ ID NO 59
<211> LENGTH: 375
<212> TYPE: DNA
<213> ORGANISM: murine
<220> FEATURE:
<221> NAME/KEY: unsure
<222> LOCATION: (1)..(375)
<223> OTHER INFORMATION: unsure at all n locations

<400> SEQUENCE: 59
nttacctccc tcagggtcct gggcatcatg tcttgctcta tgaagactga acacttacag    60
agtctgagcc ttctgcagtg gcccttgagc tacgttgcca tgttttggat tgtgcagcca    120
ttgttaattt gcctattgtt cacacccttg tggccgctac aacagtttta ctttgtctgg    180
ttacttctcg actggaagac tccagataaa ggtggcaggc gttcagactg ggtacggaac    240
tggaatgtct ggaaccacat caggggactat ttccccatta caatcctgaa gactaaggac    300
```

```
ctgtcacctt cagagaacta catcatgggg gtccacccca tnggtctcct gaccttcggt    360
gccttctgca acttc                                                     375
```

<210> SEQ ID NO 60
<211> LENGTH: 885
<212> TYPE: DNA
<213> ORGANISM: murine
<220> FEATURE:
<221> NAME/KEY: unsure
<222> LOCATION: (1)..(885)
<223> OTHER INFORMATION: unsure at all n locations

<400> SEQUENCE: 60

```
gtactacaat gggtcctatc cttcctggtg ctaggagtgg cctgcagtgt catcctcatg     60
tacaccttct gcacagactg ctggctgata gctgtgctct acttcacctg gctggcattt    120
gactggaaca cgcccaagaa aggtggcagg agatcgcagt gggtgcgaaa ctgggccgtg    180
tggcgctact tccgagacta ctttcccatc agctggtga agacacacaa cctgctgacc    240
accaggaact atatctttgg ataccacccc catggcatca tgggcctggg tgccttctgt    300
aacttcagca cagaggctac tgaagtcagc aagaagtttc ctggcataag gcctatttg    360 gctacgttgg ctggtaactt ccggatgcct gtgcttcgcg agtacctgat gtctggaggc    420
atctggcctg tcaaccgaga caccatagac tacttgctct ccaagaatgg gagtggcaat    480
gctatcatca tcgtggtggg aggtgcagct gagtccctga gctccatgcc tggcaagaac    540
gcagtcaccc tgaagaaccg caaaggcttt gtgaankyyg gatccmtgcg ccatggagct    600
gatctggttc ccacttattc ctttggagag aatgaggtat acaagcaggt gatctttgag    660
gagggttcct ggggccgatg ggtccagaag aagttccaga agtatattgg tttcgccccc    720
tgcatcttcc atggccgagg cctcttctcc tctgacacct gggggctggt gcctactcca    780
agcccatcac caccgtcgtg ggggagccca tcactgtccc caagctggag cacccgaccc    840
agaaagacat cgacctgtac catgccatgt acatggaggc cctgg                    885
```

<210> SEQ ID NO 61
<211> LENGTH: 809
<212> TYPE: DNA
<213> ORGANISM: Aspergillus fumigatus
<220> FEATURE:
<221> NAME/KEY: unsure
<222> LOCATION: (1)..(809)
<223> OTHER INFORMATION: unsure at all n locations

<400> SEQUENCE: 61

```
gtcctcctcn acatcctcta cgtcaaatat ctcgccaaag cacacaaaac cggcactta     60 gctctccgca acgaccgcct ccgcacgtcc tggatctgga agcctacgc ctcctacttc    120 cccctccgcc tctaccgctc ggtgcccntc tcccccgca aaaagtacat cttcggctac    180
catccccacg gcatcgccct ccgaggagca ctcgggaccc tagccgccga cgctgccgca    240
ttctccgatc tcttccccgg cgttacgaac acgctcctga tgaaagacga ggcgttctac    300
cagcctatat atagggagta ccttctctct acggggtga gcggcgtgtc ccactcgtcg    360
tgtatccgac acctgacccg cgcaggacat gatgggcagg gtatgggccg gcgattacc    420 atcaccgttg gcggaagtcg cgagtataac attgcgcggc cggggacgat gtgtgtggtc    480
gtccgcatcc gcaanggctt tgtgcgggtg gcggttgaga cggggcggga tctcgttcct    540
gttattgcct tcggggagaa tgagctcttt gattgtgtga atgtgtcctc gtcgactgtg    600
```

```
ctgggggttg tggccagggt atgggagtgg gctgttggcc acaaggtggc gttttcgatt      660
gtcggttcaa catttctgtc cgtatcgcgg ccggtgaatg ttgttgtngg ggancccgatt     720 cctgtgacgc ancancggtg ggatccgatc aagcgtatan tgaccattgc atggcatata     780
tccanggcac tggaanaatt ttnggaatg                                        809
```

<210> SEQ ID NO 62
<211> LENGTH: 668
<212> TYPE: DNA
<213> ORGANISM: Aspergillus fumigatus
<220> FEATURE:
<221> NAME/KEY: unsure
<222> LOCATION: (1)..(668)
<223> OTHER INFORMATION: unsure at all n locations

<400> SEQUENCE: 62

```
nctgcatttg ctactgaagc actcggattt tcgaggttgt ttccgggaat tacaaacact       60
ttacttaccc ttgattcgaa ttttcgaatt ccgttctaca gagaatatgc tcttgccatg      120
ggactcgcca gtgtttcccg ggagtcctgt gaaaacctgc tatctaaagg tggtgctgat     180
ggggaaggca tggccgcgc gattacaatt gtcattggtg gggctcgtga gtccctgcat      240
gctttacctc actctctgcg ccttgtttta aaatgccgca aaggattcat aaggctagca     300
attcgcaccg gtgctgatct tgtgccagta cttgctttcg gcgaaaacga tctctatgag     360
caggtgcgat cagatcagca tcccattata cacaagcttc aaatgctcat taagcgtacg    420
atggggttca cagttccgct ctttcatgct cgtggggttt tcaattatga cgtgggactg    480
atgccttatc gacgtccgtt gaatattgtc gttggcagac ctatacaagt cgttcaacag    540
cgtgacagag acaagattga cgaaacgtac attgatgacc ttcatgccaa gtatatacaa    600
gaactttcga cgcttrtngg gancaataca aaagatgtct tttgcggaag acccgaatc    660 ctcctgga                                                                668
```

<210> SEQ ID NO 63
<211> LENGTH: 435
<212> TYPE: DNA
<213> ORGANISM: Aspergillus ochraceus

<400> SEQUENCE: 63

```
atcaccatgc tcattacgtc ttgcttgaag cgacgtatgg ggttcataaa gctagccatc      60
cgcactggtg ctgaccttgt accagtcttg gcttttggag aaaatgatct atacgaacag     120
gtccgttcag atagccatcc ccttattcac aagttccaaa tgttggtgaa acagacactg    180
ggattcacca ttccgctgtt tcatgcacgc ggtgttttca attacgatgt tggcttgatg    240
ccgtaccgcc gcccgctgaa tattgttgtc ggccggccaa ttcatgtggt tcagcaacag    300
gacagaaaca aaatcaatga cgactatatt gatcaactcc attcagagta cgtgagagaa    360
cttgagaggc tgtgggaaga gtggaaggac gtctacgcca agaccgggt ttctgaaatt    420 gaaatagtgg cctag                                                        435
```

<210> SEQ ID NO 64
<211> LENGTH: 597
<212> TYPE: DNA
<213> ORGANISM: Candida albicans

<400> SEQUENCE: 64

```
atgaaaaatt tcatcatctg ggattggttt gtcagatatt tccctataaa ggtttataag      60
tctgtcgaat tggaaccaac attcaaagaa gttttggtag aggagactga aagttcagaa    120
```

```
gatgatgatg agcaagattt agtgtctgaa cggagcagaa cgttagttga taaagttttc    180
aaattttttg ggttgaaaaa acgtttgaat gacacttctc tggggaagtc agaaacctac    240
aagacagtgt ctactggtcc caggtatatt tttggatacc atcctcatgg agttatttca    300
atgggtgggg ttggtttatt tgctactaat tcattacgta acgagccata tacgccattt    360
ctaaaatttt tgaaaccatt cttccatgac agttccaaag gtgaacgttt atttcctggt    420
cttggaaata ttttcttgtt gacaattacc acacaatttg ccataccatt ttatcgtgat    480
tatttaatgg gattggggt tactagtgca tcagcaaaga atattagaag tttgattagc     540
aacggtgata attctgtctg tattgtagtt ggtggggcag aagagtcttt gttaaac      597

<210> SEQ ID NO 65
<211> LENGTH: 362
<212> TYPE: DNA
<213> ORGANISM: Fusarium graminearum

<400> SEQUENCE: 65
atgtctattg ccacattggt ttcggccttt tggttgattt gcgccaaccc acttgcctgg     60
cctattatta tcccttattt aattcatctt gctctatcaa ctgccggtac taatggcaac    120
ttgacatacc gctcagaatg ggttcgaagc ctgaagttgt ggaaactttt cgctggatat    180
ttccccatga agttgcacaa aacgcacgat ctgcctaccg atagaaagta catttttgga    240
taccatcccc acggtatcat ttcccatggt gcctttgccg cttttggtac caatgcccctt   300 ggattccgtg agctcttccc tgggatcaca aacacgttac ttactctaga gggggatcca    360
ct                                                                   362

<210> SEQ ID NO 66
<211> LENGTH: 431
<212> TYPE: DNA
<213> ORGANISM: Mortierella alpina
<220> FEATURE:
<221> NAME/KEY: unsure
<222> LOCATION: (1)..(431)
<223> OTHER INFORMATION: unsure at all n locations

<400> SEQUENCE: 66 ccccctgatca tcatgtacct gctctgggcc ttcatactgg accgaggccc agagcgtggt    60
gcacgcccag tgcagtggta tcgtaactgg atcggatgga aacactttgc tcaatacttt   120
cccatgactc ttgtcaagga aggagaactg gatccgtcca agaactacat ctttggctac   180
cacccgcacg gcatcatctc cttgggcgcg ttctgcacct tcgggaccga nggccttcat   240
ttctcaaaac gctttcnagg catcaagccg cagctgttga ccctgcatgc caactttcan   300
gttccgctct accgcgaaat ggtcatggcc cacggctgtg cttcggtctc tagagcctct   360
tgtgaacaca ttctgcggtc cggtgaagga tgctcggtcg tgatcgtcnt tgggggggtgc   420 tcaaganant t                                                         431

<210> SEQ ID NO 67
<211> LENGTH: 285
<212> TYPE: DNA
<213> ORGANISM: Schizochytrium aggregatum
<220> FEATURE:
<221> NAME/KEY: unsure
<222> LOCATION: (1)..(285)
<223> OTHER INFORMATION: unsure at all n locations

<400> SEQUENCE: 67
```

-continued

| | |
|---|---|
| tctatctcan nggcctatct gggaaatccg cgcatcanng gcanacggcg cttgggatcc | 60 |
| cggatattcc nttttcgcat tgttgaagac catttcagcc tctcgatggt gcgcacgtct | 120 |
| gaagagcctt gggacccgga gcacgagtac atttgtggct atcaccctca cggnctcgtg | 180 |
| cccttgggng ccgcttacat gaaaatgacc ccacaatggt cggagctcct ccccaatatt | 240 |
| gtgcccntta ctctcagcgc angcattncg cntcangtac cnana | 285 |

<210> SEQ ID NO 68
<211> LENGTH: 1080
<212> TYPE: DNA
<213> ORGANISM: Caenorhabditis elegans

<400> SEQUENCE: 68

| | |
|---|---|
| atgagactcc ggctgagctc gatatctgga aaggcgaagc ttcccgataa agaaatatgc | 60 |
| tcatcagttt cgagaatatt ggcaccattg cttgttccat ggaagcgacg actcgagact | 120 |
| cttgccgtga tgggtttcat tttcatgtgg gtaatcctac caatcatgga cctctgggta | 180 |
| ccattccacg tcttgttcaa tactcgatgg tggttccttg ttccactcta cgctgtctgg | 240 |
| ttctactatg attttgatac accgaaaaaa gcttcaagaa gatggaattg gccagaaga | 300 |
| cacgtagcct ggaagtactt tgccagctac ttcccattga gattgatcaa gactgctgac | 360 |
| cttccggcgg atcgtaatta catcattggc tctcatcctc atggaatgtt ctcggttggt | 420 |
| ggttttactg caatgagcac caacgcgacc ggatttgaag acaagttccc gggaataaaa | 480 |
| tctcacatca tgacgctaaa tgggcaattt tatttcccat tcgtcgaga attcggaata | 540 |
| atgctcggtg aatcgaagt tcgaaagaa tcacttgaat acactctaac taaatgtgga | 600 |
| aaaggacgag catgcgcaat tgtcattggc ggagcctcgg aggctcttga agctcatccc | 660 |
| aataaaaata cattgacgtt gatcaatcga cgtggtttct gcaaatatgc tctgaagttt | 720 |
| ggggcagacc tcgtaccaat gtacaatttc ggagagaatg atttatacga gcagtatgaa | 780 |
| aacccgaagg gatctagatt gcgagaagtt caggagaaaa tcaaggacat gttcggattg | 840 |
| tgtcccccat gctccgcgg tcgatcgttg ttcaaccaat accttatcgg attgctgccg | 900 |
| ttccgaaaac cagttacaac agtcatggga aggccaattc gggtcaccca aaccgacgag | 960 |
| ccaaccgttg agcagattga tgagctgcat gcaaaatatt gtgatgctct ctacaatctg | 1020 |
| ttcgaggagt acaagcatct tcactccatt cctcccgaca ctcatctcat cttccagtga | 1080 |

<210> SEQ ID NO 69
<211> LENGTH: 1020
<212> TYPE: DNA
<213> ORGANISM: Caenorhabditis elegans

<400> SEQUENCE: 69

| | |
|---|---|
| atgccacatc tactaggagt tgagtgggct ccgctcaata ttccgttggc tcggcgtctt | 60 |
| caaactttgg gagcacttca tttcttcttc atcactctct tcacaccagt actcgttctc | 120 |
| accgttccat tctacatgtt ataccgta ctctggcctt tgatctttct gtatgggctt | 180 |
| tggatgattt acgattggaa ttcaccaaag aagggagcct atatgagcaa ttggttccag | 240 |
| agacaaagaa ttcattcgtg gtatgccaac tattttccag tcaaattgca cacaacatct | 300 |
| gacatgccag aagaacataa ctatttgatt gggtaccatc cgcatggaat aatttcaatg | 360 |
| gccgcattca tcaactttgc aacaaatgga actggaattc tcgatactct tccacgaatt | 420 |
| cgtttccatt tgtgcacact tgttggtcaa ttctggactc cgtggagacg tgagtgggga | 480 |
| ttgttgcacg gaatgatgaga ctgcagtcga gaaagcatca agcacgtttt ggagcatgaa | 540 |

```
aagaaaggaa aagcagttgt attggtggtt ggtggagctg aagaagcact tgatgcacat      600
ccaggatgcc atattttgac tttgaaaaaa aggaaaggat tcgtgaaaat tgccctgcaa      660
actggagctc aactggttcc atgctattca ttcggtgaaa atgatatttt caatcaagcc      720
gaaaatccaa agggatcaac aattcgacag ttccaaacga taatgaaaag agtcttggga      780
ttctcccctc cagcattcta tgggagagga gtattcaact atacatttgg tcttcttcca      840
ttcaggaaac ctatcaacac tgttctcggc gctccaattt cagtgacaaa gacagtgaat      900
ccaactcaag aacaaatcga cacacttcat cagacataca tggaccgtct tcatgagctt      960
ttcgaggagc acaagacaaa atacgatgtc tctccaacta cacaacttgt tatcaattaa     1020
```

<210> SEQ ID NO 70
<211> LENGTH: 1038
<212> TYPE: DNA
<213> ORGANISM: Caenorhabditis elegans

<400> SEQUENCE: 70

```
atgctaaact accaaattca caaaaagctc accgacatca gtgggtgaa catcttctcc        60 ccatgggatc gccagcgtgc ctacttcgcc ttggtcgtct ggttcgggct catctaccca      120
ttctgctgcc tgtgccaggt ggctccgttt gtgctctttt tcaccggcca gtggattatt      180
ttgggtctct acgcagtttg gtacctttac gatcgagaat ctccgagaag aggaggatat      240
cgggataatt ggttcagaaa tttgtcgctg cacaagtggt tcgccgagta ttttcctgtt      300
aaacttcaca aaactgcgga gttggatcca aaccaaaatt atttattcgg atatcatcct      360
catggaattc tcggtgtcgg agcgtggtct tgttttggat tgatgcgtg caatgtgaag      420 caagtgttca aaggcatccg cttcaacatc tgcaccttgc ccggcaactt caccgcaatg      480
ttccgccgcg agatcctcct cagcatcggt atgatcgaga ctccaaaga atccatcgag      540 cacgtgctca actccgagga aaagggccgt gccgttgtaa ttgtcgtggg tggagccgct      600
gaagctcttg aagctcaccc agggaagcat actctaacac tggcaaatcg caaaggtttc      660
gtgagagaag ccgtgaagac cggagctcat ctggtgccag tttatgcgtt tggagagaat      720
gacatatata agcaaattga aacccggaa ggctcgaaat tacggaaaat tcaagaatgg      780
ggaaagaaga aaatgggaat ttcactgcca ctaatctacg aagaggata ttttcaaatg      840 gctcttgggc ttcttccaat gagccgagct gtgaatgtag ttgtcggagc gcctattcaa      900
gtggaaaaag agctcgatcc ttctaaggaa gtcattgatg aaattcatgg agtttatatg      960
gaaaagctcg ccgagttatt tgaagagcac aaggcaaagt tcggagtttc caaggacact     1020
cggctcgttt ttcagtga                                                   1038
```

<210> SEQ ID NO 71
<211> LENGTH: 315
<212> TYPE: PRT
<213> ORGANISM: Caenorhabditis elegans
<220> FEATURE:
<221> NAME/KEY: unsure
<222> LOCATION: (1)..(315)
<223> OTHER INFORMATION: unsure at all Xaa locations

<400> SEQUENCE: 71

Met Ala Glu Thr His Arg Ala Gly Xaa Ser Ser Pro His Arg Val Ser
1               5                   10                  15

Phe Pro Leu Lys Met Pro Gln Phe Leu Gly Ile Glu Trp Val Asp Leu
            20                  25                  30

```
Phe Ser Ser Ile Gln Arg Lys Lys Thr Tyr Leu Gly Val Val Tyr His
        35                  40                  45

Phe Met Leu Thr Tyr Pro Leu Ala Leu Phe Val Thr Ile Leu Pro Phe
    50                  55                  60

Phe Leu Leu Phe Thr Phe Gln Trp His Ile Leu Ala Leu Tyr Ala Cys
65                  70                  75                  80

Xaa Val Leu Leu Arg Tyr Gly Phe Ser Glu Xaa Glu Val Asp Ile Pro
                85                  90                  95

Xaa Asp Trp Met Ala Cys Gln Arg Leu Gly Ser Pro Asn Thr Ser Gln
            100                 105                 110

Ser Thr Cys Thr Lys Leu Pro Asn Ser Pro Arg Thr Arg Thr Ile Trp
        115                 120                 125

Leu Glu Ser Ile Xaa His Gly Ile Ile Ser Met Ala Ala Trp Ser Asn
130                 135                 140

Phe Ala Thr Asn Gly Thr Gly Ile Tyr Glu Lys Phe Pro Gly Ile Arg
145                 150                 155                 160

Trp Asn Leu Cys Thr Leu Ala Leu Gln Phe Arg Met Ala Ile Arg Arg
                165                 170                 175

Glu Leu Leu Leu Leu Thr Gly Leu Ile Asp Cys Ser Arg Glu Ser Ile
            180                 185                 190

Glu Tyr Val Leu Asp Lys Cys Gly Gln Lys Gly Arg Ala Val Val Leu
        195                 200                 205

Val Ile Gly Gly Ala Glu Glu Ala Leu Asp Ala His Pro Gly Tyr His
210                 215                 220

Thr Leu Thr Leu Ala Ser Arg Lys Gly Phe Val Arg Glu Ala Leu Ile
225                 230                 235                 240

Thr Gly Ala Tyr Leu Val Pro Val Tyr Ser Phe Gly Glu Asn Asp Val
                245                 250                 255

Phe Glu Gln Met Glu Asn Pro Val Gly Ser Arg Leu Arg Asn Phe Gln
            260                 265                 270

Glu Trp Cys Lys Ser Ile Phe Gly Ile Ser Tyr Pro Ile Phe His Gly
        275                 280                 285

Arg Gly Phe Phe Gln Leu Thr Phe Gly Tyr Leu Pro Phe Arg Lys Pro
290                 295                 300

Ile Asp Thr Val Xaa Arg Ser Pro Asn Ser Arg
305                 310                 315

<210> SEQ ID NO 72
<211> LENGTH: 1257
<212> TYPE: DNA
<213> ORGANISM: Saccharomyces cerevisiae

<400> SEQUENCE: 72
atgtcaggaa cattcaatga tataagaaga aggaagaagg agaaggaag ccctacagcc      60
ggtattaccg aaaggcatga gaataagtct ttgtcaagca tcgataaaag agaacagact    120
ctcaaaccac aactagagtc atgctgtcca ttggcgaccc cttttgaaag aaggttacaa    180
actctggctg tagcatggca cacttcttca tttgtactct tctccatatt tacgttattt    240
gcaatctcga caccagcact gtgggttctt gctattccat atatgattta ttttttttc    300
gataggtctc ctgcaactgg cgaagtggta aatcgatact ctcttcgatt cgttcattg    360
cccattttgga agtggtattg tgattatttc cctataagtt tgattaaaac tgtcaattta    420
aaaccaactt ttcgctttc aaaaaataag agagttaacg aaaaaaatta caagattaga    480
ttgtggccaa ctaagtattc cattaatctc aaaagcaact ctactattga ctatcgcaac    540
```

```
caggaatgta cagggccaac gtacttattt ggttaccatc cacacggcat aggagcactt    600
ggtgcgtttg gagcgtttgc aacagaaggt tgtaactatt ccaagattt cccaggtatt     660 cctatttctc tgatgacact ggtcacacaa tttcatatcc cattgtatag agactactta    720
ttggcgttag gtatttcttc agtatctcgg aaaaacgctt taaggactct aagcaaaaat    780
cagtcgatct gcattgttgt tggtggcgct agggaatctt tattaagttc aacaaatggt    840
acacaactga ttttaaacaa agaaagggt tttattaaac tggccattca acggggaat     900 attaacctag tgcctgtgtt tgcatttgga gaggtggact gttataatgt tctgagcaca    960
aaaaaagatt cagtcctggg taaaatgcaa ctatggttca agaaaacttt tggttttacc   1020
attcccattt tctacgcaag aggattattc aattacgatt tcggtttgtt gccatttaga   1080
gcgcctatca atgttgttgt tggaaggcct atatacgttg aaaagaaaat aacaaatccg   1140
ccagatgatg ttgttaatca tttccatgat ttgtatattg cggagttgaa aagactatat   1200
tacgaaaata gagaaaaata tggggtaccg gatgcagaat tgaagatagt tgggtaa      1257
```

```
<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: PCR primer
      for SEQ ID NO: 68

<400> SEQUENCE: 73
gcgcggccgc ctgcagtcac tggaagatga g                                    31

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: PCR primer
      for SEQ ID NO: 68

<400> SEQUENCE: 74
gcgcggccgc atgagactcc ggctgagctc g                                    31

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: PCR primer
      for SEQ ID NO: 69

<400> SEQUENCE: 75
gagcggccgc atgccacatc tactaggagt tga                                  33

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: PCR primer
      for SEQ ID NO: 69

<400> SEQUENCE: 76
cggcggccgc ctgcagttaa ttgataacaa gttgt                                35

<210> SEQ ID NO 77
```

```
<211> LENGTH: 32
<212> TYPE: DNA
<213> ORGANISM: Artificial Sequence
<220> FEATURE:
<223> OTHER INFORMATION: Description of Artificial Sequence: PCR primer
      for SEQ ID NO: 70

<400> SEQUENCE: 77
gcgcggccgc atgctaaact accaaattca ca                                    32

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: PCR primer
      for SEQ ID NO: 70

<400> SEQUENCE: 78
tggcggccgc ctgcagtcac tgaaaaacga gcc                                   33

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: PCR primer
      for SEQ ID NO: 71

<400> SEQUENCE: 79
cagcggccgc atgtcaggaa cattc                                            25

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: PCR primer
      for SEQ ID NO: 71

<400> SEQUENCE: 80
cactgcagtt acccaactat cttcaa                                           26

<210> SEQ ID NO 81
<211> LENGTH: 55
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 81
cgcgatttaa atggcgcgcc ctgcaggcgg ccgcctgcag ggcgcgccat ttaat           55

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 82
tcgaggatcc gcggccgcaa gcttcctgca gg                                    32

<210> SEQ ID NO 83
<211> LENGTH: 32
```

```
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 83
tcgacctgca ggaagcttgc ggccgcggat cc                                32

<210> SEQ ID NO 84
<211> LENGTH: 1068
<212> TYPE: DNA
<213> ORGANISM: Artificial Sequence
<220> FEATURE:
<223> OTHER INFORMATION: Description of Artificial Sequence:
      Resynthesized MR1 nucleic acid sequence

<400> SEQUENCE: 84
atggctagca aggaccagca cctccaacag aaggtgaagc acacccttga ggccatccca    60
tcccctaggt atgctccact cagggtccca cttaggagaa ggctccaaac ccttgctgtt   120
ctcctctggt gctccatgat gagcatctgc atgttcatct tcttcttcct ctgcagcatc   180
cctgtgctcc tttggttccc aattatcctc tacttgacct ggattttggt gtgggataag   240
gcccctgaga acggaggcag acctatcagg tggctcagga cgcagcttg gtggaagctc   300 tttgctggat acttcccagc tcatgttatc aaggaggctg accttgaccc atccaagaac   360
tacatctttg gttaccaccc acatggtatc atcagcatgg gtagcttctg caccttctcc   420
accaacgcta ctggtttcga tgacctcttc ccaggaatca ggccttcctt gctcacccrc   480
accagcaact tcaacatccc actctacagg gattacctca tggcctgtgg actctgctca   540
gtgtctaaga cctcctgcca gaacatcctc accaagggtg tccaggaag tccattgct    600 attgtggtgg gaggtgcctc tgagtccttg aacgccagac caggagtgat ggaccttgtg   660
ttgaagagga ggtttggatt catcaagatt gctgtgcaga ctggtgctag ccttgtccct   720
accatctcct ttggtgagaa tgagctttat gagcagattg agagcaatga gaactctaag   780
cttcacaggt ggcagaagaa gatccagcat gctcttggtt tcaccatgcc actcttccat   840
ggaaggggtg tgttcaacta cgactttggt ctcctcccac acaggcaccc aatttacacc   900
attgtgggta agccaatccc agtcccatct atcaagtacg tcagaccaa ggatgagatc   960 atcagggagc tccatgactc ttacatgcac gctgtgcagg acctctatga caggtacaag  1020
gacatctacg ccaaggacag ggtcaaggag cttgagtttg tggagtga                1068

<210> SEQ ID NO 85
<211> LENGTH: 1068
<212> TYPE: DNA
<213> ORGANISM: Mortierella ramanniana

<400> SEQUENCE: 85
atggccagca aggatcaaca tttacagcag aaggtcaagc atacgctaga agctatccca    60
tcccctcgct atgctccatt gcgagtgcca ttaagacgga gattacaaac attggcagtt   120
ttattatggt gttccatgat gtcaatatgc atgttcatat tcttctttt atgctccatt   180 cctgttctcc tttggttccc cattatcctt tatttgacct ggatcttggt gtgggataag   240
gcgccagaga acggtggaag acctattcgc tggctgcgga atgctgcttg gtggaagctg   300
tttgcagggt attttcccgc acatgtcatc aaggaagccg atttagatcc atccaagaac   360
tacatctttg gttatcaccc ccatggaatc atatccatgg gctcgttctg tacttttagt   420
```

-continued

```
accaatgcta ctggctttga tgacttgttc ccaggcatcc ggccatcgct tttgacatta    480
acatctaatt ttaatatccc actttatcgt gattatttga tggcgtgcgg actttgctcc    540
gtctccaaaa catcctgtca aaatatttta accaaaggtg gtccgggccg ttccattgcc    600
attgtcgtgg gaggtgcttc cgagtctctc aatgctagac cggtgtcat ggaccttgtg     660
ttgaagagac gctttggttt tatcaagatt gctgttcaaa ccggtgcaag tctagtgccc    720
actatcagtt ttggtgaaaa tgagctgtac gaacagattg aaagcaatga aaactcaaag    780
ttgcatagat ggcaaaagaa gattcaacat gcccttggtt ttactatgcc gctctttcat    840
ggacgcggtg tattcaatta tgactttggt ttgctccccc atcgccatcc tatctacacg    900
attgttggaa agcccatccc cgtccctagc atcaagtatg gacagacaaa ggatgagatt    960
ataagagaac tacatgactc gtacatgcat gccgtgcagg atctctatga tcgttacaag    1020
gatatctatg caaaggatcg ggtaaaagaa ctagaattcg tcgaatag                 1068
```

<210> SEQ ID NO 86
<211> LENGTH: 355
<212> TYPE: PRT
<213> ORGANISM: Mortierella ramanianna

<400> SEQUENCE: 86

```
Met Ala Ser Lys Asp Gln His Leu Gln Gln Lys Val Lys His Thr Leu
1               5                   10                  15

Glu Ala Ile Pro Ser Pro Arg Tyr Ala Pro Leu Arg Val Pro Leu Arg
            20                  25                  30

Arg Arg Leu Gln Thr Leu Ala Val Leu Leu Trp Cys Ser Met Met Ser
        35                  40                  45

Ile Cys Met Phe Ile Phe Phe Leu Cys Ser Ile Pro Val Leu Leu
    50                  55                  60

Trp Phe Pro Ile Ile Leu Tyr Leu Thr Trp Ile Leu Val Trp Asp Lys
65                  70                  75                  80

Ala Pro Glu Asn Gly Gly Arg Pro Ile Arg Trp Leu Arg Asn Ala Ala
                85                  90                  95

Trp Trp Lys Leu Phe Ala Gly Tyr Phe Pro Ala His Val Ile Lys Glu
            100                 105                 110

Ala Asp Leu Asp Pro Ser Lys Asn Tyr Ile Phe Gly Tyr His Pro His
        115                 120                 125

Gly Ile Ile Ser Met Gly Ser Phe Cys Thr Phe Ser Thr Asn Ala Thr
    130                 135                 140

Gly Phe Asp Asp Leu Phe Pro Gly Ile Arg Pro Ser Leu Leu Thr Leu
145                 150                 155                 160

Thr Ser Asn Phe Asn Ile Pro Leu Tyr Arg Asp Tyr Leu Met Ala Cys
                165                 170                 175

Gly Leu Cys Ser Val Ser Lys Thr Ser Cys Gln Asn Ile Leu Thr Lys
            180                 185                 190

Gly Gly Pro Gly Arg Ser Ile Ala Ile Val Val Gly Gly Ala Ser Glu
        195                 200                 205

Ser Leu Asn Ala Arg Pro Gly Val Met Asp Leu Val Leu Lys Arg Arg
    210                 215                 220

Phe Gly Phe Ile Lys Ile Ala Val Gln Thr Gly Ala Ser Leu Val Pro
225                 230                 235                 240

Thr Ile Ser Phe Gly Glu Asn Glu Leu Tyr Glu Gln Ile Glu Ser Asn
                245                 250                 255

Glu Asn Ser Lys Leu His Arg Trp Gln Lys Lys Ile Gln His Ala Leu
```

```
                260              265              270
Gly Phe Thr Met Pro Leu Phe His Gly Arg Gly Val Phe Asn Tyr Asp
            275              280              285

Phe Gly Leu Leu Pro His Arg His Pro Ile Tyr Thr Ile Val Gly Lys
        290              295              300

Pro Ile Pro Val Pro Ser Ile Lys Tyr Gly Gln Thr Lys Asp Glu Ile
305              310              315              320

Ile Arg Glu Leu His Asp Ser Tyr Met His Ala Val Gln Asp Leu Tyr
                325              330              335

Asp Arg Tyr Lys Asp Ile Tyr Ala Lys Asp Arg Val Lys Glu Leu Glu
            340              345              350

Phe Val Glu
        355

<210> SEQ ID NO 87
<211> LENGTH: 1050
<212> TYPE: DNA
<213> ORGANISM: Mortierella ramanianna

<400> SEQUENCE: 87
atggaacaag tccaagtcac tgcattgctc gaccacattc ccaaagtcca ttgggcaccg      60
ctccgtggga tccctttgaa gcgtcgctta caaacgtcgg ctatcgtcac atggctggct     120
ttgcttccta tctgtctcat tatatacctg tacctattca ccattccctt attatggccc     180
atcctcatta tgtatacgat atggctgttt ttcgacaaag cccctgaaaa cggaggcaga     240
cgaatttcgc tggtgaggaa attgccgctg tggaagcatt ttgccaatta tttcccagtc     300
actttgatca aggaaggaga cctcgacccc aagggaaaact acatcatgtc atatcatccg     360
catggaataa tatccatggc ggcttttgcc aattttgcga ctgaggcgac tgggttttcc     420
gagcaatatc cgggtattgt tccttcatta ctgacgctag catccaattt tcggttgcca     480
ttgtaccgag atttcatgat gtcactaggc atgtgctcgg tatcgcgaca ctcctgtgaa     540
gctatccttc gttcggggcc cggtcgatcc attgtgattg ttacaggcgg agcttcagaa     600
tcccttagcg cacgaccagg caccaacgac ctcaccctca gaaacgatt gggtttcatc     660 cgactagcca ttcgaaatgg tgccagttta gtgcctatct tttcgtttgg agagaacgac     720
atctacgagc aatatgataa caaaaagggc agtttgatat ggcggtacca aaaatggttc     780
caaaaaatta caggattcac ggttccttg gctcatgccc gtggcatttt caactacaat     840
gctgggttta taccattccg acatccgata gtgacagttg ttggcaaacc tattgctgtc     900
cccctcttgg ctgaaggcga aaccgaacct agcgaggagc aaatgcatca agttcaagca     960
cagtacattg aaagtttgca ggctatttat gataaataca agatattta tgctaaggat    1020 agaataaaag atatgaccat gattgcataa                                      1050

<210> SEQ ID NO 88
<211> LENGTH: 349
<212> TYPE: PRT
<213> ORGANISM: Mortierella ramanianna

<400> SEQUENCE: 88

Met Glu Gln Val Gln Val Thr Ala Leu Leu Asp His Ile Pro Lys Val
1               5                  10                  15

His Trp Ala Pro Leu Arg Gly Ile Pro Leu Lys Arg Arg Leu Gln Thr
            20                  25                  30

Ser Ala Ile Val Thr Trp Leu Ala Leu Leu Pro Ile Cys Leu Ile Ile
```

-continued

```
                35                  40                  45
Tyr Leu Tyr Leu Phe Thr Ile Pro Leu Leu Trp Pro Ile Leu Ile Met
 50                  55                  60

Tyr Thr Ile Trp Leu Phe Phe Asp Lys Ala Pro Glu Asn Gly Gly Arg
 65                  70                  75                  80

Arg Ile Ser Leu Val Arg Lys Leu Pro Leu Trp Lys His Phe Ala Asn
                 85                  90                  95

Tyr Phe Pro Val Thr Leu Ile Lys Glu Gly Asp Leu Asp Pro Lys Gly
                100                 105                 110

Asn Tyr Ile Met Ser Tyr His Pro His Gly Ile Ile Ser Met Ala Ala
                115                 120                 125

Phe Ala Asn Phe Ala Thr Glu Ala Thr Gly Phe Ser Glu Gln Tyr Pro
130                 135                 140

Gly Ile Val Pro Ser Leu Leu Thr Leu Ala Ser Asn Phe Arg Leu Pro
145                 150                 155                 160

Leu Tyr Arg Asp Phe Met Met Ser Leu Gly Met Cys Ser Val Ser Arg
                165                 170                 175

His Ser Cys Glu Ala Ile Leu Arg Ser Gly Pro Gly Arg Ser Ile Val
                180                 185                 190

Ile Val Thr Gly Gly Ala Ser Glu Ser Leu Ser Ala Arg Pro Gly Thr
                195                 200                 205

Asn Asp Leu Thr Leu Lys Lys Arg Leu Gly Phe Ile Arg Leu Ala Ile
210                 215                 220

Arg Asn Gly Ala Ser Leu Val Pro Ile Phe Ser Phe Gly Glu Asn Asp
225                 230                 235                 240

Ile Tyr Glu Gln Tyr Asp Asn Lys Lys Gly Ser Leu Ile Trp Arg Tyr
                245                 250                 255

Gln Lys Trp Phe Gln Lys Ile Thr Gly Phe Thr Val Pro Leu Ala His
                260                 265                 270

Ala Arg Gly Ile Phe Asn Tyr Asn Ala Gly Phe Ile Pro Phe Arg His
                275                 280                 285

Pro Ile Val Thr Val Val Gly Lys Pro Ile Ala Val Pro Leu Leu Ala
290                 295                 300

Glu Gly Glu Thr Glu Pro Ser Glu Gln Met His Gln Val Gln Ala
305                 310                 315                 320

Gln Tyr Ile Glu Ser Leu Gln Ala Ile Tyr Asp Lys Tyr Lys Asp Ile
                325                 330                 335

Tyr Ala Lys Asp Arg Ile Lys Asp Met Thr Met Ile Ala
                340                 345
```

<210> SEQ ID NO 89
<211> LENGTH: 418
<212> TYPE: PRT
<213> ORGANISM: Saccharomyces cerevisiae

<400> SEQUENCE: 89

```
Met Ser Gly Thr Phe Asn Asp Ile Arg Arg Lys Lys Glu Glu Gly
 1               5                  10                  15

Ser Pro Thr Ala Gly Ile Thr Glu Arg His Glu Asn Lys Ser Leu Ser
                 20                  25                  30

Ser Ile Asp Lys Arg Glu Gln Thr Leu Lys Pro Gln Leu Glu Ser Cys
                 35                  40                  45

Cys Pro Leu Ala Thr Pro Phe Glu Arg Arg Leu Gln Thr Leu Ala Val
 50                  55                  60
```

```
Ala Trp His Thr Ser Ser Phe Val Leu Phe Ser Ile Phe Thr Leu Phe
 65                  70                  75                  80

Ala Ile Ser Thr Pro Ala Leu Trp Val Leu Ala Ile Pro Tyr Met Ile
                 85                  90                  95

Tyr Phe Phe Phe Asp Arg Ser Pro Ala Thr Gly Glu Val Val Asn Arg
            100                 105                 110

Tyr Ser Leu Arg Phe Arg Ser Leu Pro Ile Trp Lys Trp Tyr Cys Asp
        115                 120                 125

Tyr Phe Pro Ile Ser Leu Ile Lys Thr Val Asn Leu Lys Pro Thr Phe
    130                 135                 140

Thr Leu Ser Lys Asn Lys Arg Val Asn Glu Lys Asn Tyr Lys Ile Arg
145                 150                 155                 160

Leu Trp Pro Thr Lys Tyr Ser Ile Asn Leu Lys Ser Asn Ser Thr Ile
                165                 170                 175

Asp Tyr Arg Asn Gln Glu Cys Thr Gly Pro Thr Tyr Leu Phe Gly Tyr
            180                 185                 190

His Pro His Gly Ile Gly Ala Leu Gly Ala Phe Gly Ala Phe Ala Thr
        195                 200                 205

Glu Gly Cys Asn Tyr Ser Lys Ile Phe Pro Gly Ile Pro Ile Ser Leu
    210                 215                 220

Met Thr Leu Val Thr Gln Phe His Ile Pro Leu Tyr Arg Asp Tyr Leu
225                 230                 235                 240

Leu Ala Leu Gly Ile Ser Ser Val Ser Arg Lys Asn Ala Leu Arg Thr
                245                 250                 255

Leu Ser Lys Asn Gln Ser Ile Cys Ile Val Val Gly Ala Arg Glu
            260                 265                 270

Ser Leu Leu Ser Ser Thr Asn Gly Thr Gln Leu Ile Leu Asn Lys Arg
        275                 280                 285

Lys Gly Phe Ile Lys Leu Ala Ile Gln Thr Gly Asn Ile Asn Leu Val
    290                 295                 300

Pro Val Phe Ala Phe Gly Glu Val Asp Cys Tyr Asn Val Leu Ser Thr
305                 310                 315                 320

Lys Lys Asp Ser Val Leu Gly Lys Met Gln Leu Trp Phe Lys Glu Asn
                325                 330                 335

Phe Gly Phe Thr Ile Pro Ile Phe Tyr Ala Arg Gly Leu Phe Asn Tyr
            340                 345                 350

Asp Phe Gly Leu Leu Pro Phe Arg Ala Pro Ile Asn Val Val Gly
        355                 360                 365

Arg Pro Ile Tyr Val Glu Lys Lys Ile Thr Asn Pro Pro Asp Asp Val
    370                 375                 380

Val Asn His Phe His Asp Leu Tyr Ile Ala Glu Leu Lys Arg Leu Tyr
385                 390                 395                 400

Tyr Glu Asn Arg Glu Lys Tyr Gly Val Pro Asp Ala Glu Leu Lys Ile
                405                 410                 415

Val Gly

<210> SEQ ID NO 90
<211> LENGTH: 345
<212> TYPE: PRT
<213> ORGANISM: Caenorhabditis elegans

<400> SEQUENCE: 90

Met Leu Asn Tyr Gln Ile His Lys Lys Leu Thr Asp Ile Lys Trp Val
1               5                   10                  15
```

```
Asn Ile Phe Ser Pro Trp Asp Arg Gln Arg Ala Tyr Phe Ala Leu Val
             20                  25                  30

Val Trp Phe Gly Leu Ile Tyr Pro Phe Cys Cys Leu Cys Gln Val Ala
         35                  40                  45

Pro Phe Val Leu Phe Phe Thr Gly Gln Trp Ile Ile Leu Gly Leu Tyr
 50                  55                  60

Ala Val Trp Tyr Leu Tyr Asp Arg Glu Ser Pro Arg Arg Gly Gly Tyr
 65                  70                  75                  80

Arg Asp Asn Trp Phe Arg Asn Leu Ser Leu His Lys Trp Phe Ala Glu
             85                  90                  95

Tyr Phe Pro Val Lys Leu His Lys Thr Ala Glu Leu Asp Pro Asn Gln
            100                 105                 110

Asn Tyr Leu Phe Gly Tyr His Pro His Gly Ile Leu Gly Val Gly Ala
            115                 120                 125

Trp Ser Cys Phe Gly Phe Asp Ala Cys Asn Val Lys Gln Val Phe Lys
130                 135                 140

Gly Ile Arg Phe Asn Ile Cys Thr Leu Pro Gly Asn Phe Thr Ala Met
145                 150                 155                 160

Phe Arg Arg Glu Ile Leu Leu Ser Ile Gly Met Ile Glu Ser Ser Lys
                165                 170                 175

Glu Ser Ile Glu His Val Leu Asn Ser Glu Glu Lys Gly Arg Ala Val
            180                 185                 190

Val Ile Val Val Gly Gly Ala Ala Glu Ala Leu Glu Ala His Pro Gly
            195                 200                 205

Lys His Thr Leu Thr Leu Ala Asn Arg Lys Gly Phe Val Arg Glu Ala
            210                 215                 220

Val Lys Thr Gly Ala His Leu Val Pro Val Tyr Ala Phe Gly Glu Asn
225                 230                 235                 240

Asp Ile Tyr Lys Gln Ile Asp Asn Pro Glu Gly Ser Lys Leu Arg Lys
                245                 250                 255

Ile Gln Glu Trp Gly Lys Lys Met Gly Ile Ser Leu Pro Leu Ile
                260                 265                 270

Tyr Gly Arg Gly Tyr Phe Gln Met Ala Leu Gly Leu Leu Pro Met Ser
                275                 280                 285

Arg Ala Val Asn Val Val Gly Ala Pro Ile Gln Val Glu Lys Glu
290                 295                 300

Leu Asp Pro Ser Lys Glu Val Ile Asp Glu Ile His Gly Val Tyr Met
305                 310                 315                 320

Glu Lys Leu Ala Glu Leu Phe Glu Glu His Lys Ala Lys Phe Gly Val
                325                 330                 335

Ser Lys Asp Thr Arg Leu Val Phe Gln
                340                 345

<210> SEQ ID NO 91
<211> LENGTH: 359
<212> TYPE: PRT
<213> ORGANISM: Caenorhabditis elegans

<400> SEQUENCE: 91

Met Arg Leu Arg Leu Ser Ser Ile Ser Gly Lys Ala Lys Leu Pro Asp
1               5                   10                  15

Lys Glu Ile Cys Ser Ser Val Ser Arg Ile Leu Ala Pro Leu Leu Val
            20                  25                  30

Pro Trp Lys Arg Arg Leu Glu Thr Leu Ala Val Met Gly Phe Ile Phe
         35                  40                  45
```

```
Met Trp Val Ile Leu Pro Ile Met Asp Leu Trp Val Pro Phe His Val
     50                  55                  60

Leu Phe Asn Thr Arg Trp Trp Phe Leu Val Pro Leu Tyr Ala Val Trp
 65                  70                  75                  80

Phe Tyr Tyr Asp Phe Asp Thr Pro Lys Lys Ala Ser Arg Arg Trp Asn
                 85                  90                  95

Trp Ala Arg Arg His Val Ala Trp Lys Tyr Phe Ala Ser Tyr Phe Pro
            100                 105                 110

Leu Arg Leu Ile Lys Thr Ala Asp Leu Pro Ala Asp Arg Asn Tyr Ile
        115                 120                 125

Ile Gly Ser His Pro His Gly Met Phe Ser Val Gly Phe Thr Ala
    130                 135                 140

Met Ser Thr Asn Ala Thr Gly Phe Glu Asp Lys Phe Pro Gly Ile Lys
145                 150                 155                 160

Ser His Ile Met Thr Leu Asn Gly Gln Phe Tyr Phe Pro Phe Arg Arg
                165                 170                 175

Glu Phe Gly Ile Met Leu Gly Gly Ile Glu Val Ser Lys Glu Ser Leu
            180                 185                 190

Glu Tyr Thr Leu Thr Lys Cys Gly Lys Gly Arg Ala Cys Ala Ile Val
        195                 200                 205

Ile Gly Gly Ala Ser Glu Ala Leu Glu Ala His Pro Asn Lys Asn Thr
    210                 215                 220

Leu Thr Leu Ile Asn Arg Arg Gly Phe Cys Lys Tyr Ala Leu Lys Phe
225                 230                 235                 240

Gly Ala Asp Leu Val Pro Met Tyr Asn Phe Gly Glu Asn Asp Leu Tyr
                245                 250                 255

Glu Gln Tyr Glu Asn Pro Lys Gly Ser Arg Leu Arg Glu Val Gln Glu
            260                 265                 270

Lys Ile Lys Asp Met Phe Gly Leu Cys Pro Pro Leu Leu Arg Gly Arg
        275                 280                 285

Ser Leu Phe Asn Gln Tyr Leu Ile Gly Leu Leu Pro Phe Arg Lys Pro
290                 295                 300

Val Thr Thr Val Met Gly Arg Pro Ile Arg Val Thr Gln Thr Asp Glu
305                 310                 315                 320

Pro Thr Val Glu Gln Ile Asp Glu Leu His Ala Lys Tyr Cys Asp Ala
                325                 330                 335

Leu Tyr Asn Leu Phe Glu Glu Tyr Lys His Leu His Ser Ile Pro Pro
            340                 345                 350

Asp Thr His Leu Ile Phe Gln
        355

<210> SEQ ID NO 92
<211> LENGTH: 339
<212> TYPE: PRT
<213> ORGANISM: Caenorhabditis elegans

<400> SEQUENCE: 92

Met Pro His Leu Leu Gly Val Glu Trp Ala Pro Leu Asn Ile Pro Leu
 1               5                  10                  15

Ala Arg Arg Leu Gln Thr Leu Gly Ala Leu His Phe Phe Ile Thr
             20                  25                  30

Leu Phe Thr Pro Val Leu Val Leu Thr Val Pro Phe Tyr Met Leu Tyr
         35                  40                  45

Thr Val Leu Trp Pro Leu Ile Phe Leu Tyr Gly Leu Trp Met Ile Tyr
```

```
                    50                  55                  60
Asp Trp Asn Ser Pro Lys Lys Gly Ala Tyr Met Ser Asn Trp Phe Gln
 65                  70                  75                  80

Arg Gln Arg Ile His Ser Trp Tyr Ala Asn Tyr Phe Pro Val Lys Leu
                     85                  90                  95

His Thr Thr Ser Asp Met Pro Glu Glu His Asn Tyr Leu Ile Gly Tyr
                    100                 105                 110

His Pro His Gly Ile Ile Ser Met Ala Ala Phe Ile Asn Phe Ala Thr
                115                 120                 125

Asn Gly Thr Gly Ile Leu Asp Thr Leu Pro Arg Ile Arg Phe His Leu
130                 135                 140

Cys Thr Leu Val Gly Gln Phe Trp Thr Pro Trp Arg Arg Glu Trp Gly
145                 150                 155                 160

Leu Leu His Gly Met Ile Asp Cys Ser Arg Glu Ser Ile Lys His Val
                165                 170                 175

Leu Glu His Glu Lys Lys Gly Lys Ala Val Val Leu Val Val Gly Gly
                180                 185                 190

Ala Glu Glu Ala Leu Asp Ala His Pro Gly Cys His Ile Leu Thr Leu
                195                 200                 205

Lys Lys Arg Lys Gly Phe Val Lys Ile Ala Leu Gln Thr Gly Ala Gln
210                 215                 220

Leu Val Pro Cys Tyr Ser Phe Gly Glu Asn Asp Ile Phe Asn Gln Ala
225                 230                 235                 240

Glu Asn Pro Lys Gly Ser Thr Ile Arg Gln Phe Gln Thr Ile Met Lys
                245                 250                 255

Arg Val Leu Gly Phe Ser Pro Pro Ala Phe Tyr Gly Arg Gly Val Phe
                260                 265                 270

Asn Tyr Thr Phe Gly Leu Leu Pro Phe Arg Lys Pro Ile Asn Thr Val
                275                 280                 285

Leu Gly Ala Pro Ile Ser Val Thr Lys Thr Val Asn Pro Thr Gln Glu
                290                 295                 300

Gln Ile Asp Thr Leu His Gln Thr Tyr Met Asp Arg Leu His Glu Leu
305                 310                 315                 320

Phe Glu Glu His Lys Thr Lys Tyr Asp Val Ser Pro Thr Thr Gln Leu
                325                 330                 335

Val Ile Asn

<210> SEQ ID NO 93
<211> LENGTH: 1023
<212> TYPE: DNA
<213> ORGANISM: Caenorhabditis elegans

<400> SEQUENCE: 93
atgccgcaat tctcggaat  agaatgggtg gatctattct catcaattca acgtaaaaag    60
acatacttgg gagttgtcta tcactttatg ctcacttacc cacttgcact tttcgtcacc   120
attttgccat ttttcttgct tttcactttc caatggcaca ttttggctct ctacgcttgc   180
tggtacttct acgatatgga ttctccgagg agaggtggat attccagtga ttgggtcaga   240
aaatggcgtg tcaacgactg gttcgcccaa tacttcccaa tcaacttgca caaaactgcc   300
gaactctcca cggacaagaa ctatctggtt ggaatccatc tcatgggtat catctccatg   360
gctgcatggt ctaattttgc caccaatgga acgggaatct atgagaaatt ccctggaatt   420
cgctggaatt tgtgcacttt agcacttcag ttcagaatgg ccatccgtcg tgagcttctc   480
```

```
cttctcaccg gcctaatcga ctgctccaga gaatccattg aatatgtgct tgacaaatgt      540
ggccagaagg gacgtgcagt ggtattggtg attggaggag ccgaagaagc tttagatgct      600
catccaggct accacacact cactttggca tcaagaaagg gatttgttcg ggaggctttg      660
attactggtg cctacttggt cccggtgtat tcttttggag agaatgacgt ttttgaacag      720
atggagaatc cagttggctc acggctccgc aacttccaag aatggtgcaa aagcattttc      780
ggcatctcat atccaatttt ccatggtcgt ggcttcttcc aactaacttt cggatatctt      840
ccattccgta aaccaatcga taccgtagtc ggagccccaa ttcccgttga aaaagtggaa      900
aatccgacga aagagcaaat cgacgagctt cacaccattt attgtcaaaa gttgacggag      960
ctgttcgatg agcacaagga aaaatatgga gtggagaagg acgtgccgtt ggtgctccgg     1020
tag                                                                   1023

<210> SEQ ID NO 94
<211> LENGTH: 340
<212> TYPE: PRT
<213> ORGANISM: Caenorhabditis elegans

<400> SEQUENCE: 94

Met Pro Gln Phe Leu Gly Ile Glu Trp Val Asp Leu Phe Ser Ser Ile
1               5                   10                  15

Gln Arg Lys Lys Thr Tyr Leu Gly Val Val Tyr His Phe Met Leu Thr
            20                  25                  30

Tyr Pro Leu Ala Leu Phe Val Thr Ile Leu Pro Phe Phe Leu Leu Phe
        35                  40                  45

Thr Phe Gln Trp His Ile Leu Ala Leu Tyr Ala Cys Trp Tyr Phe Tyr
    50                  55                  60

Asp Met Asp Ser Pro Arg Gly Gly Tyr Ser Ser Asp Trp Val Arg
65                  70                  75                  80

Lys Trp Arg Val Asn Asp Trp Phe Ala Gln Tyr Phe Pro Ile Asn Leu
                85                  90                  95

His Lys Thr Ala Glu Leu Ser Thr Asp Lys Asn Tyr Leu Val Gly Ile
            100                 105                 110

His Pro His Gly Ile Ile Ser Met Ala Ala Trp Ser Asn Phe Ala Thr
        115                 120                 125

Asn Gly Thr Gly Ile Tyr Glu Lys Phe Pro Gly Ile Arg Trp Asn Leu
    130                 135                 140

Cys Thr Leu Ala Leu Gln Phe Arg Met Ala Ile Arg Arg Glu Leu Leu
145                 150                 155                 160

Leu Leu Thr Gly Leu Ile Asp Cys Ser Arg Glu Ser Ile Glu Tyr Val
                165                 170                 175

Leu Asp Lys Cys Gly Gln Lys Gly Arg Ala Val Val Leu Val Ile Gly
            180                 185                 190

Gly Ala Glu Glu Ala Leu Asp Ala His Pro Gly Tyr His Thr Leu Thr
        195                 200                 205

Leu Ala Ser Arg Lys Gly Phe Val Arg Glu Ala Leu Ile Thr Gly Ala
    210                 215                 220

Tyr Leu Val Pro Val Tyr Ser Phe Gly Glu Asn Asp Val Phe Glu Gln
225                 230                 235                 240

Met Glu Asn Pro Val Gly Ser Arg Leu Arg Asn Phe Gln Glu Trp Cys
                245                 250                 255

Lys Ser Ile Phe Gly Ile Ser Tyr Pro Ile Phe His Gly Arg Gly Phe
            260                 265                 270
```

```
Phe Gln Leu Thr Phe Gly Tyr Leu Pro Phe Arg Lys Pro Ile Asp Thr
            275                 280                 285

Val Val Gly Ala Pro Ile Pro Val Glu Lys Val Glu Asn Pro Thr Lys
            290                 295                 300

Glu Gln Ile Asp Glu Leu His Thr Ile Tyr Cys Gln Lys Leu Thr Glu
305                 310                 315                 320

Leu Phe Asp Glu His Lys Glu Lys Tyr Gly Val Glu Lys Asp Val Pro
                325                 330                 335

Leu Val Leu Arg
            340

<210> SEQ ID NO 95
<211> LENGTH: 945
<212> TYPE: DNA
<213> ORGANISM: Arabidopsis thaliana

<400> SEQUENCE: 95
atgggtggtt ccagagagtt ccgagctgag gaacattcaa atcaattcca ctctatcatc      60
gccatggcca tctggcttgg cgccattcac ttcaacgtcg ctcttgttct ctgttctctc     120
attttccttc ctccttctct atctctcatg gtcttgggct tgctctctct gtttatcttt     180
atcccaatcg atcatcgtag caaatatggt cgtaagctcg ctaggtacat atgcaagcac     240
gcgtgtaatt atttccccgt ctctctgtac gtcgaggatt acgaagcttt ccagcctaat     300
cgtgcctatg tctttggtta tgaaccacat tcggtgctac cgattggagt tgttgctctt     360
tgtgatctca cagggtttat gcctattcct aacattaaag ttcttgcaag tagtgctata     420
ttctacactc cctttctaag gcatatatgg acatggttag ggctcaccgc tgcttctagg     480
aagaatttca cttccctttt ggattctggc tacagttgtg ttcttgtacc tggtggtgtg     540
caggagactt tcatatgca acatgatgct gagaatgtct ccctttcaag gagaagagga     600
tttgtgcgca tagccatgga acaggggagc cctctggttc cagtattctg ctttggtcag     660
gcacgcgtgt acaaatggtg gaagccggat tgtgatctct atcttaaact atctagagca     720
atcagattca ccccgatctg cttctgggga gtttttggat caccattacc gtgtcgacag     780
cctatgcatg tggtcgttgg taaaccaata gaagtcacaa aaactctgaa gccaactgac     840
gaagagattg ctaagtttca tggccagtat gtggaagcgc ttagggatct gtttgagagg     900
cacaagtccc gagtcggcta tgatcttgag ctgaaaattc tttga                     945

<210> SEQ ID NO 96
<211> LENGTH: 314
<212> TYPE: PRT
<213> ORGANISM: Arabidopsis thaliana

<400> SEQUENCE: 96

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65                  70                  75                  80

Ala Cys Asn Tyr Phe Pro Val Ser Leu Tyr Val Glu Asp Tyr Glu Ala
```

```
                85                  90                  95
Phe Gln Pro Asn Arg Ala Tyr Val Phe Gly Tyr Glu Pro His Ser Val
            100                 105                 110
Leu Pro Ile Gly Val Val Ala Leu Cys Asp Leu Thr Gly Phe Met Pro
            115                 120                 125
Ile Pro Asn Ile Lys Val Leu Ala Ser Ser Ala Ile Phe Tyr Thr Pro
            130                 135                 140
Phe Leu Arg His Ile Trp Thr Trp Leu Gly Leu Thr Ala Ala Ser Arg
145                 150                 155                 160
Lys Asn Phe Thr Ser Leu Leu Asp Ser Gly Tyr Ser Cys Val Leu Val
                165                 170                 175
Pro Gly Gly Val Gln Glu Thr Phe His Met Gln His Asp Ala Glu Asn
            180                 185                 190
Val Phe Leu Ser Arg Arg Gly Phe Val Arg Ile Ala Met Glu Gln
            195                 200                 205
Gly Ser Pro Leu Val Pro Val Phe Cys Phe Gly Gln Ala Arg Val Tyr
            210                 215                 220
Lys Trp Trp Lys Pro Asp Cys Asp Leu Tyr Leu Lys Leu Ser Arg Ala
225                 230                 235                 240
Ile Arg Phe Thr Pro Ile Cys Phe Trp Gly Val Phe Gly Ser Pro Leu
                245                 250                 255
Pro Cys Arg Gln Pro Met His Val Val Gly Lys Pro Ile Glu Val
            260                 265                 270
Thr Lys Thr Leu Lys Pro Thr Asp Glu Glu Ile Ala Lys Phe His Gly
            275                 280                 285
Gln Tyr Val Glu Ala Leu Arg Asp Leu Phe Glu Arg His Lys Ser Arg
            290                 295                 300
Val Gly Tyr Asp Leu Glu Leu Lys Ile Leu
305                 310
```

<210> SEQ ID NO 97
<211> LENGTH: 1167
<212> TYPE: DNA
<213> ORGANISM: Murinae gen. sp.

<400> SEQUENCE: 97

```
atgaagaccc tcatcgccgc ctactccggg gtcctgcggg gtgagcgtcg ggcggaagct      60
gcccgcagcg aaaacaagaa taaggatct gccctgtcac gcgaggggtc tgggcgatgg     120
ggcactggct ccagcatcct ctcagccctc aagacatct tctctgtcac ctggctcaac     180
agatctaagg tggaaaaaca gctgcaggtc atctcagtac tacaatgggt cctatccttc    240
ctggtgctag gagtggcctg cagtgtcatc ctcatgtaca ccttctgcac agactgctgg    300
ctgatagctg tgctctactt cacctggctg gcatttgact ggaacacgcc caagaaaggt    360
ggcaggagat cgcagtgggt gcgaaactgg gccgtgtggc gctacttccg agactacttt    420
cccatccagc tggtgaagac acacaacctg ctgaccacca ggaactatat ctttggatac    480
cacccccatg gcatcatggg cctgggtgcc ttctgtaact tcagcacaga ggctactgaa    540
gtcagcaaga agtttcctgg cataaggccc tatttggcta cgttggctgg taacttccgg    600
atgcctgtgc ttcgcgagta cctgatgtct ggaggcatct gccctgtcaa ccagacacc     660
atagactact tgctctccaa gaatgggagt ggcaatgcta tcatcatcgt ggtgggaggt    720
gcagctgagt ccctgagctc catgcctggc aagaacgcag tcaccctgaa gaaccgcaaa    780
ggctttgtga agctggccct gcgccatgga gctgatctgg ttcccactta ttcctttgga    840
```

```
gagaatgagg tatacaagca ggtgatcttt gaggagggtt cctggggccg atgggtccag    900
aagaagttcc agaagtatat tggtttcgcc ccctgcatct tccatggccg aggcctcttc    960
tcctctgaca cctgggggct ggtgccctac tccaagccca tcaccaccgt cgtgggggag   1020
cccatcactg tccccaagct ggagcacccg acccagaaag acatcgacct gtaccatgcc   1080
atgtacatgg aggccctggt gaagctcttt gacaatcaca agaccaaatt tggccttcca   1140
gagactgagg tgctggaggt gaactga                                      1167
```

<210> SEQ ID NO 98
<211> LENGTH: 388
<212> TYPE: PRT
<213> ORGANISM: Murinae gen. sp.

<400> SEQUENCE: 98

```
Met Lys Thr Leu Ile Ala Ala Tyr Ser Gly Val Leu Arg Gly Glu Arg
1               5                   10                  15

Arg Ala Glu Ala Ala Arg Ser Glu Asn Lys Asn Lys Gly Ser Ala Leu
            20                  25                  30

Ser Arg Glu Gly Ser Gly Arg Trp Gly Thr Gly Ser Ser Ile Leu Ser
        35                  40                  45

Ala Leu Gln Asp Ile Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Asn Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255

Lys Asn Arg Lys Gly Phe Val Lys Leu Ala Leu Arg His Gly Ala Asp
            260                 265                 270

Leu Val Pro Thr Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
```

```
            305                 310                 315                 320
Ser Ser Asp Thr Trp Gly Leu Val Pro Tyr Ser Lys Pro Ile Thr Thr
                    325                 330                 335

Val Val Gly Glu Pro Ile Thr Val Pro Lys Leu Glu His Pro Thr Gln
            340                 345                 350

Lys Asp Ile Asp Leu Tyr His Ala Met Tyr Met Glu Ala Leu Val Lys
        355                 360                 365

Leu Phe Asp Asn His Lys Thr Lys Phe Gly Leu Pro Glu Thr Glu Val
    370                 375                 380

Leu Glu Val Asn
385

<210> SEQ ID NO 99
<211> LENGTH: 1068
<212> TYPE: DNA
<213> ORGANISM: Artificial Sequence
<220> FEATURE:
<223> OTHER INFORMATION: Resynthesized Mr-1R sequence from operon
      pCGN8848 bases (127-1194)

<400> SEQUENCE: 99
atggctagca aggaccagca cctccaacag aaggtgaagc acacccttga ggccatccca      60
tcccctaggt atgctccact cagggtccca cttaggagaa ggctccaaac ccttgctgtt     120
ctcctctggt gctccatgat gagcatctgc atgttcatct tcttcttcct ctgcagcatc     180
cctgtgctcc tttggttccc aattatcctc tacttgacct ggattttggt gtgggataag     240
gcccctgaga acggaggcag acctatcagg tggctcagga acgcagcttg gtggaagctc     300
tttgctggat acttcccagc tcatgttatc aaggaggctg accttgaccc atccaagaac     360
tacatctttg gttaccaccc acatggtatc atcagcatgg gtagcttctg caccttctcc     420
accaacgcta ctggtttcga tgacctcttc ccaggaatca ggccttcctt gctcaccctc     480
accagcaact tcaacatccc actctacagg gattacctca tggcctgtgg actctgctca     540
gtgtctaaga cctcctgcca gaacatcctc accaagggtg tccaggaag tccattgct      600 attgtggtgg gaggtgcctc tgagtccttg aacgccagac caggagtgat ggaccttgtg     660
ttgaagagga ggtttggttt catcaagatt gctgtgcaga ctggtgctag ccttgtccct     720
accatctcct ttggtgagaa tgagctttat gagcagattg agagcaatga gaactctaag     780
cttcacaggt ggcagaagaa gatccagcat gctcttggtt tcaccatgcc actcttccat     840 ggaagggtg tgttcaacta cgactttggt ctcctcccac acaggcaccc aatttacacc      900
attgtgggta agccaatccc agtcccatct atcaagtacg gtcagaccaa ggatgagatc     960
atcagggagc tccatgactc ttacatgcac gctgtgcagg acctctatga caggtacaag    1020
gacatctacg ccaaggacag ggtcaaggag cttgagtttg tcgagtga                 1068

<210> SEQ ID NO 100
<211> LENGTH: 1173
<212> TYPE: DNA
<213> ORGANISM: Zea mays

<400> SEQUENCE: 100
gtcggctctt gctgatcttg ttggctttct gcctctcact aagatcaagg tccttgcgag      60
cagtgcggta agtcagctaa atgccttgac gccaaatgcc acaggattca gggactcccc     120
tcatgatggt taatttcgaa ttggggccag gtgttctaca ccccgttctt gagacagatt     180
tggacatggc ttggcttggt acctgcgaca aggaagaatt tctactgcta ccttggagct     240
```

```
ggttatagtt gtatcgtagt ccctggtggc acgagggtgt acgggaaatg cttcatatga    300
acaatgattc agaggttgct tttcttaaat caagaaaagg ttttgtcaag atagctatac    360
agtctggatg tcctttagtc ccagtttttct gctttgggca gagctatgca tacaagtggt   420
ggaggcctgg tggtaaattg tttatcaaga tcgctagagc agttaaattt actcctatta    480
tcttctgggg tagatttggc acaccattcc ccttcccaaa acccatgcat gtggtcgtgg    540
gtaaacctat tgaagtcaat aagattcccc atcctacaat tgacgagatt aatgaagtcc    600
atgaacagtt catcattgcc atgcgggacc tctttgagaa gtacaaggcg aaagctggat    660
atcctggcct tcatctaaga gtcctatgac attccacaac cagactcaaa gttagaattc    720
agcaataaca tggctctatt actcttccct caactggggt gtcaaactgc acctcgcagg    780
cactcgggcg gtagttgttg cattatggtg atgataataa ggctccagca ccgatgccaa    840
aacatgcacg agttggtcac gagtcagagc cttttgttgc tggcttaact tttttaatag    900
atatatgccc gtgcgttgct acagaatcat ggttatgtga tgttgcatat gatatgagaa    960
tatgcgtgtt tggtttggat cttggcttcg gcttttgccc cctaaaagcc attgccaaac   1020
caaagggctg aatctggaaa gcagcttttct ctaaaagccg actttttttgg agtgcaaaac   1080 taaaagcacc tctggacctg cttttagcag cttttaggtg aaactgtgaa aatatatatg   1140
gaataatttt tatcaaaaaa aaaaaaaaaa ggg                                 1173

<210> SEQ ID NO 101
<211> LENGTH: 430
<212> TYPE: DNA
<213> ORGANISM: Zea mays

<400> SEQUENCE: 101
ccacgcgtcc gcgagcttat gtttttgctt atgaaccgca ttcggtgctg cctattggcg     60
tttgtgcgct tgcggatcat acaggttttt tgcccctgcc gaagattaag gctcttgcga    120
gtaccgcggt tttctatgtg ccgtttgtga ggcagatatg gacatggttg gggcttgtcc    180
ctgcgtcgag aaggaatttt tacgagtact tggcggctgg gtatagttgc atcatagtgc    240
cgggtggtgt gcaggagttg ttgtatatgg aatgtgattc ggaggttgct tttcttaaat    300
caaggaaagg atttgtaaag atagccatgg agatgggtca acctcttgta cctgtattct    360
gctttggtca gagttaagcg tacaagtggt ggaagccaag tgggaaatta tatttacgta    420
tttccagagc                                                           430

<210> SEQ ID NO 102
<211> LENGTH: 477
<212> TYPE: DNA
<213> ORGANISM: Brassica napus
<220> FEATURE:
<221> NAME/KEY: misc_feature
<222> LOCATION: (1)..(477)
<223> OTHER INFORMATION: unsure at all n locations

<400> SEQUENCE: 102
aacnttactt gccaggcacc ggtcaagaan tcccgggtcg acccacgcgt ccgcaaatac     60
ggtcgaatgc tcgctaggta catatgtaaa cacgcgtgta gttatttccc cgttactctc    120
catgtcgagg attacgaagc tttccagcct actcgtgcct atgttttttgg ttatgaacca    180 cattcggtgt ggcctattgg agctgttgca cttgctgatc ttacgggggtt catgcctctt    240 cctaacatca aagttcttgc tagtactgct gttttctaca cacccttttct gaggcaaata    300
```

```
tggacgtggt tagggctcgc ccctgcttct aggaagaatt tcgcttccta tttggactct    360
ggctatagtt gtatcctcgt acctggtggt gtccaggaga catttcacat gaaacatgat    420
gttgagaact tattcctttc atccgagaan ggggtttgtg cgcatcgcca tgggagc       477
```

<210> SEQ ID NO 103
<211> LENGTH: 990
<212> TYPE: DNA
<213> ORGANISM: Glycine max

<400> SEQUENCE: 103

```
atggcggcgg aaccggtgag tgacggcgga gccgcggcgg agaaattgat cagcgggaga     60
gaagaatttg gtgattcgtc caacttgttc agcgcgattc tagcaatggt gctgtggctg    120
ggagctattc atttcaacat cgccctgatc ctcctcgccg tgttcttcct tcctctctcc    180
aaatcgctct tggttttcgg ttttctcttt gggtttatgg tgcttcctat caacgagaag    240
agcagatttg gccgaagatt gtcgaggttc atatgcaagc acgcttgcaa ttactttccg    300
atcacgcttc acgtagagga tatgaaagcc tttgatccta accgtgctta tgttttgggg    360
tatgaaccac attcagtttt gccaattggc attgttgcat ggctgaccca cacaggtttc    420
atgcctcttc caaaagttaa agttcttgct agcagcacgg tgttctacac accatttttg    480
agacacttat ggacatggtt gggtcttaca ccagcaacaa agaaaaattt tatctccctg    540
ttagcatctg gccatagttg catttttaata cctggtggag tgcaagaagc atttcacatg    600
cagcatggca ctgagattgc tttccttaag gcaagaagag gatttgtccg cgtagcaatg    660
gtgaaaggca aacctttggt tccagtcttc tgctttggtc agtcaaatgt ctataagtgg    720
tggaaaccag gtgggaagtt atttctgaaa tttgcaaggg ctatcaagtt caccccaata    780
tgttttgggg gaattttttgg gtctccatta ccgttcagac atccaatgca tgtggttgtg    840
ggtagaccaa ttgaggttga caaaaaccga gaaccaacca ccgaggaggt tgccaagata    900
catgggctat ttgtggaagc acttcaagat ctctttgaac ggcacaaagc tcgggctggc    960
tatccaaacc ttgagttaag aatagtttga                                     990
```

<210> SEQ ID NO 104
<211> LENGTH: 329
<212> TYPE: PRT
<213> ORGANISM: Glycine max

<400> SEQUENCE: 104

```
Met Ala Ala Glu Pro Val Ser Asp Gly Gly Ala Ala Glu Lys Leu
1               5                   10                  15

Ile Ser Gly Arg Glu Glu Phe Gly Asp Ser Ser Asn Leu Phe Ser Ala
            20                  25                  30

Ile Leu Ala Met Val Leu Trp Leu Gly Ala Ile His Phe Asn Ile Ala
        35                  40                  45

Leu Ile Leu Leu Ala Val Phe Phe Pro Leu Ser Lys Ser Leu Leu
    50                  55                  60

Val Phe Gly Phe Leu Phe Gly Phe Met Val Leu Pro Ile Asn Glu Lys
65                  70                  75                  80

Ser Arg Phe Gly Arg Arg Leu Ser Arg Phe Ile Cys Lys His Ala Cys
                85                  90                  95

Asn Tyr Phe Pro Ile Thr Leu His Val Glu Asp Met Lys Ala Phe Asp
            100                 105                 110

Pro Asn Arg Ala Tyr Val Phe Gly Tyr Glu Pro His Ser Val Leu Pro
        115                 120                 125
```

Ile Gly Ile Val Ala Leu Ala Asp His Thr Gly Phe Met Pro Leu Pro
            130                 135                 140

Lys Val Lys Val Leu Ala Ser Ser Thr Val Phe Tyr Thr Pro Phe Leu
145                 150                 155                 160

Arg His Leu Trp Thr Trp Leu Gly Leu Thr Pro Ala Thr Lys Lys Asn
                165                 170                 175

Phe Ile Ser Leu Leu Ala Ser Gly His Ser Cys Ile Leu Ile Pro Gly
            180                 185                 190

Gly Val Gln Glu Ala Phe His Met Gln His Gly Thr Glu Ile Ala Phe
        195                 200                 205

Leu Lys Ala Arg Arg Gly Phe Val Arg Val Ala Met Val Lys Gly Lys
    210                 215                 220

Pro Leu Val Pro Val Phe Cys Phe Gly Gln Ser Asn Val Tyr Lys Trp
225                 230                 235                 240

Trp Lys Pro Gly Gly Lys Leu Phe Leu Lys Phe Ala Arg Ala Ile Lys
                245                 250                 255

Phe Thr Pro Ile Cys Phe Trp Gly Ile Phe Gly Ser Pro Leu Pro Phe
            260                 265                 270

Arg His Pro Met His Val Val Gly Arg Pro Ile Glu Val Asp Lys
        275                 280                 285

Asn Arg Glu Pro Thr Thr Glu Glu Val Ala Lys Ile His Gly Leu Phe
    290                 295                 300

Val Glu Ala Leu Gln Asp Leu Phe Glu Arg His Lys Ala Arg Ala Gly
305                 310                 315                 320

Tyr Pro Asn Leu Glu Leu Arg Ile Val
                325

<210> SEQ ID NO 105
<211> LENGTH: 577
<212> TYPE: DNA
<213> ORGANISM: Arabidopsis thaliana

<400> SEQUENCE: 105
tgtacgtcga ggattacgaa gctttccagc ctaatcgtgc ctatgtcttt ggttatgaac      60
cacattcggt gctaccgatt ggagttgttg ctctttgtga tctcacaggg tttatgccta     120
ttcctaacat taaagttctt gcaagtagtg ctatattcta cactcccttt ctaaggcata     180
tatggacatg gttagggctc accgctgctt ctaggaagaa tttcactttc cttttggatt     240
ctggctacag ttgtgttctt gtacctggtg gtgtgcagga gacttttcat atgcaacatg     300
atgctgagaa tgtcttcctt tcaaggagaa gaggatttgt gcgcatagcc atggaacagg     360
ggagccctct ggttccagta ttctgctttg gtcaggcacg cgtgtacaaa tggtggaagc     420
cggattgtga tctctatctt aaactatcta gagcaatcag attcaccccg atctgcttct     480
ggagagtttt tggatcacca ttaccgtgtc gacagcctat gcatgtggtc gttggtaaac     540
caatagaagt cacacaaact cttgagccaa ctgacga                              577

<210> SEQ ID NO 106
<211> LENGTH: 559
<212> TYPE: DNA
<213> ORGANISM: Arabidopsis thaliana

<400> SEQUENCE: 106
agacgaagat ggtggaatct tcgtggttca tgggtgcatg atgagctttc cgcatattgg      60
tatatgaata tcattcgcga gcgagagttg aaccctcgag agaagcacat ttttgggtac     120

```
gcaccacatg gtatgttccc gatgggcgcc tcttatctcc acaacacctc gatgtggatg    180
gaactcttcc caaacattgt gccttataca cttacagcga cggtgactca tctggttccg    240
tttctaagag aagtgactca gtataacgga ggtgttgaag tcagtcaaag tagttttgca    300
aacgcgttga tgaaattcaa aaacgttttg ctggtccccg gaggacaaca tgaaatgtta    360
ctcatcagcg acgaccataa cgaagtgctt ttatccgcca aacacaaggg attcattcga    420
ttagccttgc aatcggcagc agaaaaccca gatgaagtca tcaacctcgt cccggtgtac    480
gcttttggag aaaaagacaa aatgtataac gcattccctg cgagtctctc tctgcagcga    540
tatctggtgg ccaagctgc                                                 559

<210> SEQ ID NO 107
<211> LENGTH: 786
<212> TYPE: DNA
<213> ORGANISM: Homo sapiens

<400> SEQUENCE: 107
cggtgtcttg ccttccatcc tcccttcatc ctgctcaaca ccccgaagct ggtgaaaaca     60
gcagagctgc ccccggatcg gaactacgtg ctgggcgccc accctcatgg gatcatgtgt    120
acaggcttcc tctgtaattt ctccaccgag agcaatggct ctcccagct cttcccgggg     180 ctccggccct ggttagccgt gctggctggc ctcttctacc tcccggtcta tcgcgactac    240
atcatgtcct ttggactctg tccggtgagc cgccagagcc tggacttcat cctgtcccag    300
ccccagctcg ggcaggccgt ggtcatcatg gtggggggtg cgcacgaggc cctgtattca    360
gtccccgggg agcactgcct tacgctccag aagcgcaaag gcttcgtgcg cctggcgctg    420
aggcacgggg cgtccctggt gcccgtgtac tcctttgggg agaatgacat ctttagactt    480
aaggcttttg ccacaggctc ctggcagcat tggtgccagc tcaccttcaa gaagctcatg    540
ggcttctctc cttgcatctt ctggggtcgc ggtctcttct cagccacctc ctggggcctg    600
ctgccctttg ctgtgcccat caccactgtg gtgggccgcc ccatcccgt ccccagcgc     660 ctccacccca ccgaggagga agtcaatcac tatcacgccc tctacatgac ggccctggag    720
cagctcttcg aggagcacaa ggaaagctgt ggggtcccccg cttccacctg cctcaccttc    780
atctag                                                              786

<210> SEQ ID NO 108
<211> LENGTH: 786
<212> TYPE: DNA
<213> ORGANISM: Mortierella ramanianna

<400> SEQUENCE: 108
cggtgtcttg ccttccatcc tcccttcatc ctgctcaaca ccccgaagct ggtgaaaaca     60
gcagagctgc ccccggatcg gaactacgtg ctgggcgccc accctcatgg gatcatgtgt    120
acaggcttcc tctgtaattt ctccaccgag agcaatggct ctcccagct cttcccgggg     180 ctccggccct ggttagccgt gctggctggc ctcttctacc tcccggtcta tcgcgactac    240
atcatgtcct ttggactctg tccggtgagc cgccagagcc tggacttcat cctgtcccag    300
ccccagctcg ggcaggccgt ggtcatcatg gtggggggtg cgcacgaggc cctgtattca    360
gtccccgggg agcactgcct tacgctccag aagcgcaaag gcttcgtgcg cctggcgctg    420
aggcacgggg cgtccctggt gcccgtgtac tcctttgggg agaatgacat ctttagactt    480
aaggcttttg ccacaggctc ctggcagcat tggtgccagc tcaccttcaa gaagctcatg    540
```

```
ggcttctctc cttgcatctt ctggggtcgc ggtctcttct cagccacctc ctggggcctg      600
ctgccctttg ctgtgcccat caccactgtg gtgggccgcc ccatcccgt ccccagcgc       660 ctccacccca ccgaggagga agtcaatcac tatcacgccc tctacatgac ggccctggag     720
cagctcttcg aggagcacaa ggaaagctgt ggggtccccg cttccacctg cctcaccttc    780
atctag                                                                786
```

<210> SEQ ID NO 109
<211> LENGTH: 855
<212> TYPE: DNA
<213> ORGANISM: Homo sapiens

<400> SEQUENCE: 109

```
atggtagagt tcgcgccctt gtttatgccg tgggagcgca ggctgcagac acttgctgtc     60
ctacagtttg tcttctcctt cttggcactg gccgagatct gcactgtggg cttcatagcc    120
ctcctgttta caagattctg gctcctcact gtcctgtatg cggcctggtg gtatctggac    180
cgagacaagc cacggcaggg gggccggcac atccaggcca tcaggtgctg gactatatgg    240
aagtacatga aggactattt ccccatctcg ctggtcaaga ctgctgagct ggaccctct     300 cggaactaca ttgcgggctt ccaccccat ggagtcctgg cagtcggagc ctttgccaac    360
ctgtgcactg agagcacagg cttctcttcg atcttcccg gtatccgccc ccatctgatg    420
atgccgacct tgtggttccg ggcccccttc ttcagagatt acatcatgtc tgcagggttg    480
gtcacatcag aaaaggagag tgctgctcac attctgaaca ggaagggtgg cggaaacttg    540
ctgggcatca ttgtaggggg tgcccaggag gccctggatg ccaggcctgg atccttcacg    600
ctgttactgc ggaaccgaaa gggcttcgtc aggctcgccc tgacacacgg gtatcaagcc    660
tctgggaaga gcactctggg ttcagttggc aattggcaag atttttattt tggtgggaag    720
atggcagaga cgaatgcaga ttctattttg gtagagattt tcagtccatt cacaattaag    780
attatatttt ggtgtcttat gcccaaatac ctagaaaagt ttccacaacg gagactcagt    840
gatctaagaa actag                                                     855
```

<210> SEQ ID NO 110
<211> LENGTH: 284
<212> TYPE: PRT
<213> ORGANISM: Homo sapiens

<400> SEQUENCE: 110

```
Met Val Glu Phe Ala Pro Leu Phe Met Pro Trp Glu Arg Arg Leu Gln
1               5                   10                  15

Thr Leu Ala Val Leu Gln Phe Val Phe Ser Phe Leu Ala Leu Ala Glu
                20                  25                  30

Ile Cys Thr Val Gly Phe Ile Ala Leu Leu Phe Thr Arg Phe Trp Leu
            35                  40                  45

Leu Thr Val Leu Tyr Ala Ala Trp Trp Tyr Leu Asp Arg Asp Lys Pro
        50                  55                  60

Arg Gln Gly Gly Arg His Ile Gln Ala Ile Arg Cys Trp Thr Ile Trp
65                  70                  75                  80

Lys Tyr Met Lys Asp Tyr Phe Pro Ile Ser Leu Val Lys Thr Ala Glu
                85                  90                  95

Leu Asp Pro Ser Arg Asn Tyr Ile Ala Gly Phe His Pro His Gly Val
                100                 105                 110

Leu Ala Val Gly Ala Phe Ala Asn Leu Cys Thr Glu Ser Thr Gly Phe
            115                 120                 125
```

```
Ser Ser Ile Phe Pro Gly Ile Arg Pro His Leu Met Met Pro Thr Leu
        130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Arg Asn Arg Lys Gly
        195                 200                 205

Phe Val Arg Leu Ala Leu Thr His Gly Tyr Gln Ala Ser Gly Lys Ser
    210                 215                 220

Thr Leu Gly Ser Val Gly Asn Trp Gln Gly Phe Tyr Gly Gly Lys
225                 230                 235                 240

Met Ala Glu Thr Asn Ala Asp Ser Ile Leu Val Glu Ile Phe Ser Pro
                245                 250                 255

Phe Thr Ile Lys Ile Ile Phe Trp Cys Leu Met Pro Lys Tyr Leu Glu
            260                 265                 270

Lys Phe Pro Gln Arg Arg Leu Ser Asp Leu Arg Asn
        275                 280

<210> SEQ ID NO 111
<211> LENGTH: 1167
<212> TYPE: DNA
<213> ORGANISM: Homo sapiens

<400> SEQUENCE: 111
atgaagaccc tcatagccgc ctactccggg gtcctgcgcg cgagcgtca ggccgaggct      60 gaccggagcc agcgctctca cggaggacct gcgctgtcgc gcgaggggtc tgggagatgg    120
ggcactggat ccagcatcct ctccgccctc caggacctct tctctgtcac ctggctcaat    180
aggtccaagg tggaaaagca gctacaggtc atctcagtgc tccagtgggt cctgtccttc    240
cttgtactgg gagtggcctg cagtgccatc ctcatgtaca tattctgcac tgattgctgg    300
ctcatcgctg tgctctactt cacttggctg gtgtttgact ggaacacacc caagaaaggt    360
ggcaggaggt cacagtgggt ccgaaactgg ctgtgtggc gctactttcg agactacttt    420
cccatccagc tggtgaagac acacaacctg ctgaccacca ggaactatat ctttggatac    480 caccccatg gtatcatggg cctgggtgcc ttctgcaact tcagcacaga ggccacagaa    540
gtgagcaaga agttcccagg catacggcct acctggcta cactggcagg caacttccga    600
atgcctgtgt tgagggagta cctgatgtct ggaggtatct gccctgtcag ccgggacacc    660
atagactatt tgctttcaaa gaatgggagt ggcaatgcta tcatcatcgt ggtcgggggt    720
gcggctgagt ctctgagctc catgcctggc aagaatgcag tcaccctgcg gaaccgcaag    780
ggctttgtga aactggccct gcgtcatgga gctgacctgg ttccatctca ctcctttgga    840
gagaatgaag tgtacaagca ggtgatcttc gaggagggct cctggggccg atgggtccag    900
aagaagttcc agaaatacat tggtttcgcc ccatgcatct tccatggtcg aggcctcttc    960
tcctccgaca cctggggggct ggtgccctac tccaagccca tcaccactgt tgtgggagag   1020
cccatcacca tccccaagct ggagcaccca acccagcaag acatcgacct gtaccacacc   1080
atgtacatgg aggccctggt gaagctcttc gacaagcaca gaccaagtt cggcctcccg    1140 gagactgagg tcctggaggt gaactga                                       1167
```

<210> SEQ ID NO 112
<211> LENGTH: 388
<212> TYPE: PRT
<213> ORGANISM: Homo sapiens

<400> SEQUENCE: 112

```
Met Lys Thr Leu Ile Ala Ala Tyr Ser Gly Val Leu Arg Gly Glu Arg
1               5                   10                  15

Gln Ala Glu Ala Asp Arg Ser Gln Arg Ser His Gly Gly Pro Ala Leu
            20                  25                  30

Ser Arg Glu Gly Ser Gly Arg Trp Gly Thr Gly Ser Ser Ile Leu Ser
        35                  40                  45

Ala Leu Gln Asp Leu Phe Ser Val Thr Trp Leu Asn Arg Ser Lys Val
50                  55                  60

Glu Lys Gln Leu Gln Val Ile Ser Val Leu Gln Trp Val Leu Ser Phe
65                  70                  75                  80

Leu Val Leu Gly Val Ala Cys Ser Ala Ile Leu Met Tyr Ile Phe Cys
                85                  90                  95

Thr Asp Cys Trp Leu Ile Ala Val Leu Tyr Phe Thr Trp Leu Val Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Ser Arg Asp Thr Ile Asp Tyr Leu
210                 215                 220

Leu Ser Lys Asn Gly Ser Gly Asn Ala Ile Ile Ile Val Val Gly Gly
225                 230                 235                 240

Ala Ala Glu Ser Leu Ser Ser Met Pro Gly Lys Asn Ala Val Thr Leu
                245                 250                 255

Arg Asn Arg Lys Gly Phe Val Lys Leu Ala Leu Arg His Gly Ala Asp
            260                 265                 270

Leu Val Pro Ile Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Ile Pro Lys Leu Glu His Pro Thr Gln
            340                 345                 350

Gln Asp Ile Asp Leu Tyr His Thr Met Tyr Met Glu Ala Leu Val Lys
        355                 360                 365

Leu Phe Asp Lys His Lys Thr Lys Phe Gly Leu Pro Glu Thr Glu Val
370                 375                 380
```

Leu Glu Val Asn
385

<210> SEQ ID NO 113
<211> LENGTH: 603
<212> TYPE: DNA
<213> ORGANISM: Homo sapiens

<400> SEQUENCE: 113

```
ggccgccggt ttacctgtgt gaggcactgg cgcctgtgga acactacag cgattatttc    60
cctctcaagc ttctgaagac tcatgacatc tgccccagcc gcaactacat cctcgtctgc   120
caccctcatg ggctctttgc ccatggatgg tttggccact tgccacaga ggcctcaggc   180
ttctccaaga tatttcctgg catcacccct tacatactca cactgggagc cttttctgg   240
atgcctttcc tcagagaata tgtaatgtct acaggggcct gctctgtgag tcgatcctcc   300
attgactttc tgctgactca taaaggcaca ggcaacatgg tcattgtggt gattggtgga   360
ctggctgagt gcagatacag cctgccaggt tcttctaccc tggtgttgaa gaaccggtct   420
ggctttgtgc gcatggccct tcagcatggg taaggacagc tccagtccag gctggcggaa   480
gggatccaaa agtgttgcag ggaaagaaga gggggttttg atgaaaggac atccacagag   540
agaggaggaa gtatacaata cattcttacg aactatggtc atcagaaaga taagttttat   600
ttg                                                                  603
```

<210> SEQ ID NO 114
<211> LENGTH: 1008
<212> TYPE: DNA
<213> ORGANISM: Murinae gen. sp.

<400> SEQUENCE: 114

```
atgatggtcg agttcgcgcc actcaacacc ccgctggcac ggtgcctaca gaccgctgcg    60
gtgctgcagt gggtcctgtc cttcctcctg ctcgtgcagg tgtgcattgg aattatggtg   120
atgctggtcc tgtacaacta ttggttcctt tacatcccat atctggtctg gttttactat   180
gactggagaa ccccagagca aggaggcaga agatggaact gggtccaaag ctggcctgtg   240
tggaagtatt ttaaggagta ttttccaatc tgtcttgtca aaacgcagga tttggatccg   300
ggtcacaatt atatatttgg gtttcaccct catggaatat tcgtgcctgg agcctttgga   360
aatttttgta caaatactc ggacttcaag aagctatttc ctggctttac atcgtatctc   420
cacgtggcca agatctggtt ctgtttcccg ttgttccgag aatatctgat gagtaacggg   480
ccggtttcag tgtctaagga gagtttgtct catgtgctga gcaaggatgg aggtggcaat   540
gtctcaatca ttgtcctcgg aggtgcaaag gaggcgctgg aggctcaccc aggaacattc   600
accctgtgca tccgccagcg caaagggttt gttaagatgg ccttgaccca tggtgccagt   660
ttggttccag tattttcttt tggtgaaaat gatctatata agcaaattaa caaccccaaa   720
ggctcctggc tacgaactat acaagacgca atgtatgatt caatgggagt agccttgcca   780
ctgatatatg ccagaggaat tttccagcac tactttggca taatgcccta tcggaagctg   840
atctacactg ttgttggccg ccctatcccct gttcagcaga ttctgaaccc gacctcagag   900
cagattgaag agctgcatca gacataccta gaggagctaa agaaactatt caatgaacac   960
aaagggaaat atgggattcc ggagcacgaa actctggtat ttaaataa             1008
```

<210> SEQ ID NO 115
<211> LENGTH: 335

```
<212> TYPE: PRT
<213> ORGANISM: Murinae gen. sp.

<400> SEQUENCE: 115

Met Met Val Glu Phe Ala Pro Leu Asn Thr Pro Leu Ala Arg Cys Leu
1               5                   10                  15

Gln Thr Ala Ala Val Leu Gln Trp Val Leu Ser Phe Leu Leu Leu Val
            20                  25                  30

Gln Val Cys Ile Gly Ile Met Val Met Leu Val Leu Tyr Asn Tyr Trp
        35                  40                  45

Phe Leu Tyr Ile Pro Tyr Leu Val Trp Phe Tyr Tyr Asp Trp Arg Thr
50                  55                  60

Pro Glu Gln Gly Gly Arg Arg Trp Asn Trp Val Gln Ser Trp Pro Val
65                  70                  75                  80

Trp Lys Tyr Phe Lys Glu Tyr Phe Pro Ile Cys Leu Val Lys Thr Gln
                85                  90                  95

Asp Leu Asp Pro Gly His Asn Tyr Ile Phe Gly Phe His Pro His Gly
            100                 105                 110

Ile Phe Val Pro Gly Ala Phe Gly Asn Phe Cys Thr Lys Tyr Ser Asp
        115                 120                 125

Phe Lys Lys Leu Phe Pro Gly Phe Thr Ser Tyr Leu His Val Ala Lys
130                 135                 140

Ile Trp Phe Cys Phe Pro Leu Phe Arg Glu Tyr Leu Met Ser Asn Gly
145                 150                 155                 160

Pro Val Ser Val Ser Lys Glu Ser Leu Ser His Val Leu Ser Lys Asp
                165                 170                 175

Gly Gly Gly Asn Val Ser Ile Ile Val Leu Gly Gly Ala Lys Glu Ala
            180                 185                 190

Leu Glu Ala His Pro Gly Thr Phe Thr Leu Cys Ile Arg Gln Arg Lys
        195                 200                 205

Gly Phe Val Lys Met Ala Leu Thr His Gly Ala Ser Leu Val Pro Val
210                 215                 220

Phe Ser Phe Gly Glu Asn Asp Leu Tyr Lys Gln Ile Asn Asn Pro Lys
225                 230                 235                 240

Gly Ser Trp Leu Arg Thr Ile Gln Asp Ala Met Tyr Asp Ser Met Gly
                245                 250                 255

Val Ala Leu Pro Leu Ile Tyr Ala Arg Gly Ile Phe Gln His Tyr Phe
            260                 265                 270

Gly Ile Met Pro Tyr Arg Lys Leu Ile Tyr Thr Val Val Gly Arg Pro
        275                 280                 285

Ile Pro Val Gln Gln Ile Leu Asn Pro Thr Ser Glu Gln Ile Glu Glu
290                 295                 300

Leu His Gln Thr Tyr Leu Glu Glu Leu Lys Lys Leu Phe Asn Glu His
305                 310                 315                 320

Lys Gly Lys Tyr Gly Ile Pro Glu His Glu Thr Leu Val Phe Lys
                325                 330                 335

<210> SEQ ID NO 116
<211> LENGTH: 435
<212> TYPE: DNA
<213> ORGANISM: Murinae gen. sp.
<220> FEATURE:
<221> NAME/KEY: misc_feature
<222> LOCATION: (1)..(435)
<223> OTHER INFORMATION: unsure at all n locations

<400> SEQUENCE: 116
```

-continued

```
ttacctccct cagggtcctg gcatcatgt cttgctctat gaagactgaa cacttacaga    60
gtctgagcct tctgcagtgg cccttgagct acgttgccat gttttggatt gtgcagccat  120
tgttaatttg cctattgttc acacccttgt ggccgctacc aacagtttac tttgtctggt  180
tacttctcga ctggaagact ccagataaag gtggcaggcg ttcagactgg gtacggaact  240
ggaatgtctg gaaccacatc agggactatt tccccattac aatcctgaag actaaggacc  300
tgtcaccttc agagaactac atcatggggg tccacccat nggtcctg accttcggtg    360 ccttctgcaa cttctgcact gaggccacag gcttctcgaa gaccttccca ggcatcactc  420
ctcacttggc cacac                                                    435
```

<210> SEQ ID NO 117
<211> LENGTH: 790
<212> TYPE: DNA
<213> ORGANISM: Aspergillus fumigatus

<400> SEQUENCE: 117

```
gagacatcaa agaaccctc gtcgtgacta cactatgcaa tgcctggttt ctcttcccac    60
tactcggata ctcccttcta ctcgtcccga cgatgcgtct ctctgtcctc ctctacatcc  120
tctacgtcaa atatctcgcc aaagcacaca aaaccggcac tttagctctc cgcaacgacc  180
gcctccgcac gtcctggatc tggaaagcct acgcctccta cttccccatc cgcctctacc  240
gctcggtgcc catctccccc cgcaaaaagt acatcttcgg ctaccatccc acggcatcg   300 ccctccgagg agcactcggg accctagccg ccgacgctgc cgcattctcc gatctcttcc  360
ccggcgttac gaacacgctc ctgatgaaag acgaggcgtt ctaccagcct atatataggg  420
agtaccttct ctctacgggg gtgagcggcg tgtcccactc gtcgtgtatc cgacacctga  480
cccgcgcagg acatgatggg cagggtatgg gccgggcgat taccatcacc gttggcggaa  540
gtcgcgagta taacattgcg cggccgggga cgatgtgtgt ggtcgtccgc atccgcaagg  600
gctttgtgcg ggtggcggtt gagacggggg cggatctcgt tcctgttatt gccttcgggg  660
agaatgagct ctttgattgt gtgaatgtgt cctcgtcgac tgtgctgggg gttgtggcca  720
gggtatggga gtgggctgtt ggccacaagg tggcgttttc gactggtcgg ttcaacatct  780
tctgtccgta                                                          790
```

<210> SEQ ID NO 118
<211> LENGTH: 1720
<212> TYPE: DNA
<213> ORGANISM: Aspergillus fumigatus

<400> SEQUENCE: 118

```
gctgcatttg ctactgaagc actcggattt tcgaggttgt ttccgggaat tacaaacact    60
ttacttaccc ttgattcgaa ttttcgaatt ccgttctaca gagaatatgc tcttgccatg   120
ggactcgcca gtgtttcccg ggagtcctgt gaaaacctgc tatctaaagg tggtgctgat  180
ggggaaggca tggccgcgc gattacaatt gtcattggtg gggctcgtga gtccctgcat   240
gctttacctc actctctgcg ccttgtttta aaatgccgca aaggattcat aaggctagca  300
attcgcaccg gtgctgatct tgtgccagta cttgctttcg gcgaaaacga tctctatgag  360
caggtgcgat cagatcagca tcccattata cacaagcttc aaatgctcat taagcgtacg  420 atgggggttca cagttccgct cttttcatgct cgtggggttt tcaattatga cgtgggactg  480
atgccttatc gacgtccgtt gaatattgtc gttggcagac ctatacaagt cgttcaacag  540
```

```
cgtgacagag acaagattga cgaaacgtac attgatgacc ttcatgccaa gtatatacaa    600
gaacttcgac gcttgtggga gcaatacaaa gatgtctttg cgaaggaccg aatctctgaa    660
ttgagatagt tgcgtgaaac ggccctgctt tcgctgtcat cttttgatgc actcctcctg    720
taattgaaca agggacaaat aattcggcaa gaaaaatgag agagcttccc ggcaagcctg    780
aatgatattc caccgctgat caaatcatca atcacaagcg ggcatcctcg aggtgatcct    840
caggaagggg cctgtgaggt catacgggtt gagaccatcg atcgattacc ttcgacctaa    900
tgacttgaca cttcaggcca ggaatcagct ttagaggttt tgagaacatg tcgtgatatt    960
atgtatgcct acgaacttcg tctgggataa cacttggaca atgcatgctt cctatcaatt    1020
taggaatccc tcatagtgac attgttcctg ctcgcaatcc gggtgtctcc atcgccgcaa    1080
gtaattccaa ttccaaagta aggtgggcgg tgctctgaaa gtccagaaat gctagatcaa    1140
aatctttaga aattctctac ctatgttctg gttcacagac aatcctcatg ctaagatgcc    1200
tggttgcctc tgatgaacgg gtgtttgaac agcagccaat aatcatatgc caggactgat    1260
ctccacattc taccatcatg ttctttattt ctccatacac tatgtatgct ctttagttac    1320
aattcagctt ttaaattaaa taggaggttt gactactgtc ttaacttgca aagcgaactc    1380
acattagttt attcaattta aacatggcta tctcaacaag tcgggttcaa ggggaaaaaa    1440
aaatcatgca tgggtatcta aatatgcagc gaaatcatga ctacactctc agcagatgg    1500 tagcctcctg attccatcaa gaccacctt gaaataccaa gggcataagg caagactggc    1560
agctcacacc cgtagtcatg accacaaaca aaataggagg aaaggactca gtatgaaggt    1620
taacttcgga ttattcgggg gaatttccga atccaggaaa atatgaaatt tggcctgagc    1680
caaggggaac acagttggga cagaaggacg acttaggact                         1720
```

<210> SEQ ID NO 119
<211> LENGTH: 435
<212> TYPE: DNA
<213> ORGANISM: Aspergillus ochraceus

<400> SEQUENCE: 119

```
atcaccatgc tcattacgtc ttgcttgaag cgacgtatgg ggttcataaa gctagccatc    60
cgcactggtg ctgaccttgt accagtcttg gcttttggag aaaatgatct atacgaacag    120
gtccgttcag atagccatcc ccttattcac aagttccaaa tgttggtgaa acagacactg    180
ggattcacca ttccgctgtt tcatgcacgc ggtgttttca attacgatgt tggcttgatg    240
ccgtaccgcc gcccgctgaa tattgttgtc ggccggccaa ttcatgtggt tcagcaacag    300
gacagaaaca aaatcaatga cgactatatt gatcaactcc attcagagta cgtgagagaa    360
cttgagaggc tgtgggaaga gtggaaggac gtctacgcca aagaccgggt ttctgaaatt    420
gaaatagtgg cctag                                                    435
```

<210> SEQ ID NO 120
<211> LENGTH: 597
<212> TYPE: DNA
<213> ORGANISM: Candida albicans

<400> SEQUENCE: 120

```
atgaaaaatt tcatcatctg ggattggttt gtcagatatt tccctataaa ggtttataag    60
tctgtcgaat tggaaccaac attcaaagaa gttttggtag aggagactga aagttcagaa    120
gatgatgatg agcaagattt agtgtctgaa cggagcagaa cgttagttga taagagttttc    180 aaatttttttg ggttgaaaaa acgtttgaat gacacttctc tggggaagtc agaaacctac    240
```

```
aagacagtgt ctactggtcc caggtatatt tttggatacc atcctcatgg agttatttca    300
atgggtgggg ttggtttatt tgctactaat tcattacgta acgagccata tacgccattt    360
ctaaaatttt tgaaaccatt cttccatgac agttccaaag gtgaacgttt atttcctggt    420
cttggaaata ttttcttgtt gacaattacc acacaatttg ccataccatt ttatcgtgat    480
tatttaatgg gattggggt tactagtgca tcagcaaaga atattagaag tttgattagc     540
aacggtgata attctgtctg tattgtagtt ggtggggcag aagagtcttt gttaaac       597

<210> SEQ ID NO 121
<211> LENGTH: 362
<212> TYPE: DNA
<213> ORGANISM: Fusarium graminearum

<400> SEQUENCE: 121
atgtctattg ccacattggt ttcggccttt tggttgattt gcgccaaccc acttgcctgg     60
cctattatta tcccttattt aattcatctt gctctatcaa ctgccggtac taatggcaac    120
ttgacatacc gctcagaatg ggttcgaagc ctgaagttgt ggaaactttt cgctggatat    180
ttccccatga agttgcacaa aacgcacgat ctgcctaccg atagaaagta cattttggga    240
taccatcccc acggtatcat ttcccatggt gcctttgccg cttttggtac caatgccctt    300
ggattccgtg agctcttccc tgggatcaca aacacgttac ttactctaga gggggatcca    360
ct                                                                   362

<210> SEQ ID NO 122
<211> LENGTH: 431
<212> TYPE: DNA
<213> ORGANISM: Mortierella alpina
<220> FEATURE:
<221> NAME/KEY: misc_feature
<222> LOCATION: (1)..(431)
<223> OTHER INFORMATION: unknown at all n locations

<400> SEQUENCE: 122
cccctgatca tcatgtacct gctctgggcc ttcatactgg accgaggccc agagcgtggt     60
gcacgcccag tgcagtggta tcgtaactgg atcggatgga acactttgc tcaatacttt     120 cccatgactc ttgtcaagga aggagaactg gatccgtcca agaactacat ctttggctac    180 caccccgcacg gcatcatctc cttgggcgcg ttctgcacct tcgggaccga nggccttcat   240
ttctcaaaac gctttcnagg catcaagccg cagctgttga ccctgcatgc caacttttcan  300 gttccgctct accgcgaaat ggtcatggcc cacggctgtg cttcggtctc tagagcctct   360
tgtgaacaca ttctgcggtc cggtgaagga tgctcggtcg tgatcgtcnt tgggggtgc    420 tcaaganant t                                                         431

<210> SEQ ID NO 123
<211> LENGTH: 285
<212> TYPE: DNA
<213> ORGANISM: Schizochytrium aggregatum
<220> FEATURE:
<221> NAME/KEY: misc_feature
<222> LOCATION: (1)..(285)
<223> OTHER INFORMATION: unknown at all n locations

<400> SEQUENCE: 123
tctatctcan nggcctatct gggaaatccg cgcatcanng gcanacggcg cttgggatcc     60
cggatattcc nttttcgcat tgttgaagac catttcagcc tctcgatggt gcgcacgtct   120
```

-continued

```
gaagagcctt gggacccgga gcacgagtac atttgtggct atcaccctca cggnctcgtg    180
cccttgggng ccgcttacat gaaaatgacc ccacaatggt cggagctcct ccccaatatt    240
gtgcccntta ctctcagcgc angcattncg cntcangtac cnana                    285
```

<210> SEQ ID NO 124
<211> LENGTH: 945
<212> TYPE: DNA
<213> ORGANISM: Arabidopsis thaliana

<400> SEQUENCE: 124

```
atgggtggtt ccagagagtt ccgagctgag gaacattcaa atcaattcca ctctatcatc     60
gccatggcca tctggcttgg cgccattcac ttcaacgtcg ctcttgttct ctgttctctc    120
attttccttc ctccttctct atctctcatg gtcttgggct tgctctctct gtttatcttt    180
atcccaatcg atcatcgtag caaatatggt cgtaagctcg ctaggtacat atgcaagcac    240
gcgtgtaatt atttccccgt ctctctgtac gtcgaggatt acgaagcttt ccagcctaat    300
cgtgcctatg tctttggtta tgaaccacat tcggtgctac cgattggagt tgttgctctt    360
tgtgatctca cagggtttat gcctattcct aacattaaag ttcttgcaag tagtgctata    420
ttctacactc cctttctaag gcatatatgg acatggttag ggctcaccgc tgcttctagg    480
aagaatttca cttcccttt ggattctggc tacagttgtg ttcttgtacc tggtggtgtg    540
caggagactt ttcatatgca acatgatgct gagaatgtct tcctttcaag gagaagagga    600
tttgtgcgca tagccatgga acaggggagc cctctggttc cagtattctg ctttggtcag    660
gcacgcgtgt acaaatggtg gaagccggat tgtgatctct atcttaaact atctagagca    720
atcagattca ccccgatctg cttctgggga gttttttggat caccattacc gtgtcgacag    780
cctatgcatg tggtcgttgg taaaccaata gaagtcacaa aaactctgga gccaactgac    840
gaagagattg ctaagtttca tggccagtat gtggaagcgc ttagggatct gtttgagagg    900
cacaagtccc gagtcggcta tgatcttgag ctgaaaattc tttga                    945
```

<210> SEQ ID NO 125
<211> LENGTH: 314
<212> TYPE: PRT
<213> ORGANISM: Arabidopsis thaliana

<400> SEQUENCE: 125

```
Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65                  70                  75                  80

Ala Cys Asn Tyr Phe Pro Val Ser Leu Tyr Val Glu Asp Tyr Glu Ala
                85                  90                  95

Phe Gln Pro Asn Arg Ala Tyr Val Phe Gly Tyr Glu Pro His Ser Val
            100                 105                 110

Leu Pro Ile Gly Val Val Ala Leu Cys Asp Leu Thr Gly Phe Met Pro
        115                 120                 125

Ile Pro Asn Ile Lys Val Leu Ala Ser Ser Ala Ile Phe Tyr Thr Pro
```

```
                130                 135                 140
Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Arg Gly Phe Val Arg Ile Ala Met Glu Gln
            195                 200                 205

Gly Ser Pro Leu Val Pro Val Phe Cys Phe Gly Gln Ala Arg Val Tyr
210                 215                 220

Lys Trp Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
                245                 250                 255

Pro Cys Arg Gln Pro Met His Val Val Gly Lys Pro Ile Glu Val
            260                 265                 270

Thr Lys Thr Leu Glu Pro Thr Asp Glu Glu Ile Ala Lys Phe His Gly
            275                 280                 285

Gln Tyr Val Glu Ala Leu Arg Asp Leu Phe Glu Arg His Lys Ser Arg
290                 295                 300

Val Gly Tyr Asp Leu Glu Leu Lys Ile Leu
305                 310

<210> SEQ ID NO 126
<211> LENGTH: 1167
<212> TYPE: DNA
<213> ORGANISM: Murinae gen. sp.

<400> SEQUENCE: 126
atgaagaccc tcatcgccgc ctactccggg gtcctgcggg gtgagcgtcg ggcggaagct      60
gcccgcagcg aaaacaagaa taaaggatct gccctgtcac gcgagggggtc tgggcgatgg    120 ggcactggct ccagcatcct ctcagccctc aagacatct tctctgtcac ctggctcaac      180
agatctaagg tggaaaaaca gctgcaggtc atctcagtac tacaatgggt cctatccttc     240
ctggtgctag gagtggcctg cagtgtcatc ctcatgtaca ccttctgcac agactgctgg     300
ctgatagctg tgctctactt cacctggctg gcatttgact ggaacacgcc caagaaaggt     360
ggcaggagat cgcagtgggt gcgaaactgg gccgtgtggc gctacttccg agactacttt     420
cccatccagc tggtgaagac acacaacctg ctgaccacca ggaactatat ctttggatac     480
cacccccatg gcatcatggg cctgggtgcc ttctgtaact tcagcacaga ggctactgaa     540
gtcagcaaga gtttcctgg cataaggccc tatttggcta cgttggctgg taacttccgg      600
atgcctgtgc ttcgcgagta cctgatgtct ggaggcatct gccctgtcaa ccgagacacc     660
atagactact gctctccaa gaatgggagt ggcaatgcta tcatcatcgt ggtgggaggt     720
gcagctgagt ccctgagctc catgcctggc aagaacgcag tcaccctgaa gaaccgcaaa    780
ggctttgtga agctggccct gcgccatgga gctgatctgg ttcccactta ttcctttgga    840
gagaatgagg tatacaagca ggtgatcttt gaggagggtt cctggggccg atgggtccag    900
aagaagttcc agaagtatat tggtttcgcc ccctgcatct ccatggccg aggcctcttc    960 tcctctgaca cctggggct ggtgccctac tccaagccca tcaccacgtc gtggggggag   1020
cccatcactg tccccaagct ggagcacccg acccagaaag acatcgacct gtaccatgcc   1080
```

```
atgtacatgg aggccctggt gaagctcttt gacaatcaca agaccaaatt tggccttcca    1140
gagactgagg tgctggaggt gaactga                                        1167
```

<210> SEQ ID NO 127
<211> LENGTH: 388
<212> TYPE: PRT
<213> ORGANISM: Murinae gen sp.

<400> SEQUENCE: 127

```
Met Lys Thr Leu Ile Ala Ala Tyr Ser Gly Val Leu Arg Gly Glu Arg
1               5                   10                  15

Arg Ala Glu Ala Ala Arg Ser Glu Asn Lys Asn Lys Gly Ser Ala Leu
            20                  25                  30

Ser Arg Glu Gly Ser Gly Arg Trp Gly Thr Gly Ser Ser Ile Leu Ser
        35                  40                  45

Ala Leu Gln Asp Ile Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Asn Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255

Lys Asn Arg Lys Gly Phe Val Lys Leu Ala Leu Arg His Gly Ala Asp
            260                 265                 270

Leu Val Pro Thr Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Val Pro Lys Leu Glu His Pro Thr Gln
            340                 345                 350
```

```
                             -continued
Lys Asp Ile Asp Leu Tyr His Ala Met Tyr Met Glu Ala Leu Val Lys
        355                 360                 365

Leu Phe Asp Asn His Lys Thr Lys Phe Gly Leu Pro Glu Thr Glu Val
    370                 375                 380

Leu Glu Val Asn
385
```

DIACYLGLYCEROL ACYL TRANSFERASE PROTEINS

This application is a continuation of U.S. application Ser. No. 11/528,485, filed Sep. 27, 2006, which is a continuation of U.S. application Ser. No. 10/208,018, filed Jul. 31, 2002, now U.S. Pat. No. 7,135,617, which is a continuation-in-part of U.S. application Ser. No. 10/121,857, filed Apr. 15, 2002, now U.S. Pat. No. 6,822,141, which is a continuation of U.S. application Ser. No. 09/345,461, filed Jun. 30, 1999, now abandoned, which claims the benefit of U.S. Provisional Application No. 60/091,631 filed Jul. 2, 1998, and U.S. Provisional Application No. 60/130,829 filed Apr. 23, 1999; the disclosures of which are each incorporated herein by reference.

TECHNICAL FIELD

The present invention is directed to enzymes, methods to purify, and obtain such enzymes, amino acid and nucleic acid sequences related thereto, and methods of use for such compositions in genetic engineering applications.

BACKGROUND OF THE INVENTION

Triacylglycerol (TAG) is thought to be the most important storage of energy for cells. Diacylglycerol acyl transferase is an enzyme which is believed to regulate TAG structure and direct TAG synthesis. The reaction catalyzed by DAGAT is at a critical branchpoint in glycerolipid biosynthesis. Enzymes at such branchpoints are considered prime candidates for sites of metabolic regulation. There are several enzymes which are common to the synthesis of diacylglycerol, TAG and membrane lipids, however, the DAGAT reaction is specific for oil synthesis.

In plants, TAG is the primary component of vegetable oil that is used by the seed as a stored form of energy to be used during seed germination. Higher plants appear to synthesize oils via a common metabolic pathway. Fatty acids are made in plastids from acetyl-CoA through a series of reactions catalyzed by enzymes known collectively as Fatty Acid Synthetase (FAS). The fatty acids produced in plastids are exported to the cytosolic compartment of the cell, and are esterified to coenzyme A. These acyl-CoAs are the substrates for glycerolipid synthesis in the endoplasmic reticulum (ER). Glycerolipid synthesis itself is a series of reactions leading first to phosphatidic acid (PA) and diacylglycerol (DAG). Either of these metabolic intermediates may be directed to membrane phospholipids such as phosphatidylglycerol (PG), phosphatidylethanolamine (PE) or phosphatidylcholine (PC), or they may be directed on to form neutral triacylglycerol (TAG).

Diacylglycerol (DAG) is synthesized from glycerol-3-phosphate and fatty acyl-CoAs in two steps catalyzed sequentially by glycerol-3-phosphate acyltransferase (G3PAT), and lysophosphatidic acid acyltransferase (LPAAT) to make PA, and then an additional hydrolytic step catalyzed by phosphatidic acid phosphatase (PAP) to make DAG. In most cells, DAG is used to make membrane phospholipids, the first step being the synthesis of PC catalyzed by CTP-phosphocholine cytidylyltransferase. In cells producing storage oils, DAG is acylated with a third fatty acid in a reaction catalyzed by diacylglycerol acyltransferase (DAGAT). Collectively, the reactions make up part of what is commonly referred to as the Kennedy Pathway.

Diacylglycerol acyltransferase (hereinafter referred to as DAGAT or DGAT) is an integral membrane protein that catalyzes the final enzymatic step in the production of triacylglycerols in plants, fungi and mammals. DGAT has generally been described in Harwood, J. Biochem. Biophysics. Acta, 1301:7-56 (1996); Daum G., et al. Yeast 16:1471-1510 (1998); and Coleman, R., et al. Annu. Rev. Nutr. 20:77-103 (2000) (all of which are herein incorporated by reference). This enzyme is responsible for transferring an acyl group from acyl-coenzyme-A to the sn-3 position of 1,2-diacylglycerol (DAG) to form triacylglycerol (TAG). As the final step in TAG biosynthesis via the Kennedy pathway, it is the only step not involved in membrane biosynthesis. In plants and fungi DGAT is associated with the membrane and lipid body fractions, particularly in oilseeds, where it contributes to the storage of carbon used as energy reserves. In animals, the role of DGAT is more complex. Triacylglycerols are synthesized and stored in several cell types including adipocytes and hepatocytes (Bell, R. M., et al. Annu. Rev. Biochem. 49:459-487 (1980) (herein incorporated by reference)) but in addition, DGAT may play a role in lipoprotein assembly and the regulation of plasma triacylglycerol concentration (Bell, R. M., et al.), as well as participate in the regulation of DAG levels (Brindley, D. N. Biochemistry of Lipids, Lipoproteins and Membranes, eds. Vance, D. E. & Vance, J. E. (Elsevier, Amsterdam), 171-203; and Nishizuka, Y. Science 258:607-614 (1992) (both of which are herein incorporated by reference)).

The structure of the TAG, as far as positional specificity of fatty acids, is determined by the specificity of each of the three acyltransferases for the fatty acyl-CoA and the glycerol backbone substrates. Thus, for example, there is a tendency for the acyltransferases from many temperate zone species of seeds to allow either a saturated or an unsaturated fatty acid at the sn-1 or the sn-3 position, but only an unsaturated fatty acid at the sn-2. The absolute specificity for an unsaturated fatty acid at sn-2 is determined by the substrate preference of LPAAT enzyme. In some species such as cocoa, TAG compositions suggest that this tendency is carried further in that there is an apparent preference for acylation of the sn-3 position with a saturated fatty acid, if the sn-1 position is esterified to a saturated fatty acid. Thus, there is a higher percentage of structured TAG of the form SUS (where S=saturated fatty acid and U=unsaturated fatty acid), than would be expected from a random distribution based on the overall fatty acid composition with the sn-2 position fixed with an unsaturated fatty acid. This suggests that DAGAT also plays an important role in the regulation of TAG structure, if not also in the control of TAG synthesis.

Obtaining nucleic acid sequences capable of producing a phenotypic result in the incorporation of fatty acids into a glycerol backbone to produce an oil is subject to various obstacles including but not limited to the identification of metabolic factors of interest, choice and characterization of a protein source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful tissue sources for nucleic acid sequences of such enzyme targets capable of modifying oil structure and quantity are needed. Ideally an enzyme target will be amenable to one or more applications alone or in combination with other nucleic acid sequences relating to increased/decreased oil production, TAG structure, the ratio of saturated to unsaturated fatty acids in the fatty acid pool, and/or to other novel oils compositions as a result of the modifications to the fatty acid pool.

For example, in some instances having an oilseed with a higher ratio of oil to seed meal would be useful to obtain a desired oil at lower cost. This would be typical of a high value oil product. Or such an oilseed might constitute a superior feed for animals. In some instances having an oilseed with a lower ratio of oil to seed meal would be useful to lower caloric content. In other uses, edible plant oils with a higher percentage of unsaturated fatty acids are desired for cardiovascular health reasons. And alternatively, temperate substitutes for high saturate tropical oils such as palm, coconut, or cocoa would also find uses in a variety of industrial and food applications.

In mammals, DAGAT plays an important role in the metabolism of cellular diacylglycerol and is important in processes involving triacylglycerol metabolism including intestinal fat absorption, lipoprotein assembly, adipose tissue formation and lactation. As such, identification and isolation of the DAGAT protein and of polynucleotide and polypeptide sequences is desired.

Several putative isolation procedures have been published for DAGAT. Polokoff and Bell (1980) reported solubilization and partial purification of DAGAT from rat liver microsomes. This preparation was insufficiently pure to identify a specific protein factor responsible for the activity. Kwanyuen and Wilson (1986, 1990) reported purification and characterization of the enzyme from soybean cotyledons. However, the molecular mass (1843 kDa) suggests that this preparation was not extensively solubilized and any DAGAT protein contained therein was part of a large aggregate of many proteins. Little et al (1993) reported solubilization of DAGAT from microspore-derived embryos from rapeseed, but as with Kwanyuen and Wilson, the molecular mass of the material that was associated with activity was so high, that complete solubilization is unlikely. Andersson et al (1994) reported solubilization and a 415-fold purification of DAGAT from rat liver using immunoaffinity chromatography. However, there is no evidence that the antibodies they used recognize DAGAT epitopes, nor that the protein that they purified is truly DAGAT. Indeed, as with Kwanyuen and Wilson, the DAGAT activity in their preparations exhibited a molecular mass typical of aggregated membrane proteins. Finally, Kamisaka et al (1993, 1994, 1996, 1997) report solubilization of DAGAT from *Mortierella rammaniana* and subsequent purification to homogeneity. They suggest that DAGAT solubilized from this fungal species has an apparent molecular mass of 53 kDa by SDS-PAGE. However, as shown in Example 4 below, fractions obtained using the protocol described by Kamisaka et al. did not provide abundant 53-kDa polypeptide which correlated with DAGAT activity.

Cases et al. reported a cloning of a DGAT gene from mouse. Using coding sequences from acyl CoA:cholesterol acyltransferase (ACAT), EST databases were searched and a gene identified that shared 20% identity with the mouse ACAT. After cloning and expression of the gene in insect cells no ACAT activity was reported in isolated membranes. Using [1-$^{14}$C]oleoyl-CoA as substrate a range of acceptors was examined and Cases et al. reported DAG as the acceptor molecule. Hobbs et al. (1999) *FEBS Letters* 452:145-149 (herein incorporated by reference) reported the cloning of an *Arabidopsis* homologue of the mouse DGAT gene and reported the presence of DGAT activity in insect cells expressing the cDNA. Southern analysis indicated a single gene copy was present in *Arabidopsis*. Katavic et al. (1995) *Plant Physiol.* 108:399-409 and Zou et al. (1999) *The Plant Journal* 19:645-653 (both of which are herein incorporated by reference) also reported this gene in seed oil production when an insertional mutation (AS11) in the gene was found to lower seed oil levels and decrease DGAT activity. The locus, at approximately 35 cM on chromosome II, was designated TAG1. Routaboul J. M., et al. (1999) *Plant Physiol. Biochem.* 37:831-840 (herein incorporated by reference) reported similar results identifying an *Arabidopsis* mutant (ABX45) harboring a frame-shift mutation near the 5' end of the TAG1 reading frame. This mutation resulted in a complete change in coding sequence after the first 60 amino acids. With the identification of a single DGAT gene copy in *Arabidopsis* and the detection of DGAT activity even after a frame shift mutation disabled gene translation, Routaboul et al. concluded that another protein must be responsible for the remaining DGAT activity.

SUMMARY OF THE INVENTION

The present invention is directed to diacylglycerol acyl transferase (DAGAT), and in particular to DAGAT polypeptides and polynucleotides. The polypeptides and polynucleotides of the present invention include those derived from plant, mammalian, including human, nematode and fungal sources.

In another aspect, the invention provides DAGAT proteins having molecular weights between approximately 36 kDa and 37 kDa, based on SDS-PAGE analysis, and particularly molecular weights of 36 kDa and 36.5 kDa. The preferred DAGAT proteins of the invention are obtainable from *Mortierella ramanniana*.

In a further aspect the invention relates to oligonucleotides derived from the DAGAT proteins and oligonucleotides which include partial or complete DAGAT encoding sequences.

It is also an aspect of the present invention to provide recombinant DNA constructs which can be used for transcription or transcription and translation (expression) of DAGAT. In particular, constructs are provided which are capable of transcription or transcription and translation in plant and mammalian host cells. Particularly preferred constructs are those capable of transcription or transcription and translation in plant cells.

In another aspect of the present invention, methods are provided for production of DAGAT in a host cell or progeny thereof. In particular, host cells are transformed or transfected with a DNA construct which can be used for transcription or transcription and translation of DAGAT. The recombinant cells which contain DAGAT are also part of the present invention.

In a further aspect, the present invention relates to methods of using polynucleotide and polypeptide sequences to modify the ratios of oils to other constituents, as well as to modify the composition and/or structure of triglyceride molecules, particularly in seed oil of oilseed crops. Plant cells having such a modified triglyceride are also contemplated herein.

The modified plants, seeds and oils obtained by the expression of the plant DAGAT proteins are also considered part of the invention.

In a further aspect, the invention relates to methods for using such polypeptides and polynucleotides in mammals are provided. Such methods include treating or ameliorating diseases associated with DAGAT activity, including diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis. In addition, methods are provided for altering the levels of DAGAT activity.

In another aspect of the present invention, methods for identifying agonists and antagonists/inhibitors of DAGAT, and treating conditions associated with DAGAT activity or altering levels of DAGAT activity with such agonists or antagonists are provided.

It is also an aspect of the present invention to provide diagnostic assays for detecting alterations in the level of DAGAT activity and for diagnosing conditions associated with DAGAT activity.

The present invention provides a class of proteins involved in TAG production. The polynucleotides identified in the present invention include proteins with DGAT activity that are unrelated to the previously identified DGAT gene family (reported in application Ser. No. 09/326,203 (herein incorporated by reference) and referred to as DGAT1), which is related to the ACAT gene family. The present invention identifies a DGAT family of proteins, designated herein as DGAT2.

The present invention further relates to polypeptides and polynucleotides in the DGAT family. Preferably, the present invention relates to polynucleotides encoding a polypeptide having a molecular weight of approximately 36 kD based on SDS-PAGE analysis (DGAT2A), and a polypeptide having a molecular weight of approximately 36.5 kD polypeptide based on SDS-PAGE analysis (referred to hereinafter as DGAT2B). More preferably, the polypeptides and polynucleotides of the present invention are isolated from *M. ramanniana, C. elegans, S. cerevisiae* and *A. thaliana*. Even more preferably, the polynucleotides of the present invention are isolated from *M. ramanniana*.

The present invention includes nucleotide sequences encoding two proteins involved in DGAT activity associated with the DGAT2 gene family and isolated from *M. ramanniana*. A first nucleotide sequence (referred to herein as DGAT2A) encodes a protein having a molecular weight of approximately 36 kD, based on SDS-PAGE analysis. A second nucleotide sequence (referred to herein as DGAT2B) encodes a protein having a molecular weight of approximately 36.5 kD based on SDS-PAGE.

The present invention further relates to polynucleotides derived from the DGAT proteins and polynucleotides which include partial or complete DGAT encoding sequences. Preferably, the present invention relates to polynucleotides derived from the DGAT2 proteins and polynucleotides which include partial or complete DGAT2 encoding sequences.

The polynucleotides of the present invention include those derived from *M. ramanniana, C. elegans, S. cerevisiae* and *A. thaliana*. Even more preferably, the present invention relates to *M. ramanniana* DGAT2 polynucleotide.

The present invention also provides recombinant DNA constructs that can be used for transcription and expression of DGAT, including constructs that are capable of expressing DGAT in plant, insect, and mammalian host cells. The present invention includes constructs that express DGAT2 proteins.

The present invention further provides methods for the production of DGAT proteins in a host cell or progeny thereof. Recombinant cells containing DGAT are also part of the present invention.

The present invention further provides methods of using polynucleotide and polypeptide sequences to modify the ratios of oils to other constituents, as well as to modify the composition and/or structure of triglyceride molecules, particularly in seed oil of oilseed crops. Plant cells having such a modified triglyceride are also provided by the present invention.

The present invention includes and provides a transformed plant having an introduced nucleic acid molecule comprising a nucleic acid sequence selected from the group consisting of SEQ ID NOs: 85, 87, 93, 95, 97, 99, 100, 101, 102, 103, 105, 106, 107, 108, 109, 111, 113, 114, 116, 117, 118, 119, 120, 121, 122, 123, 124, 126, and complements thereof.

The present invention includes and provides a transformed plant having an introduced nucleic acid molecule comprising a nucleic acid sequence encoding a polypeptide having an amino acid selected from the group consisting of SEQ ID NOs: 86, 88, 89, 90, 91, 92, 94, 96, 98, 104, 110, 112, 115, 125, and 127.

The present invention includes and provides a transformed plant having an introduced first nucleic acid molecule comprising a nucleic acid sequence selected from the group consisting of SEQ ID NOs: 85, 87, 93, 95, 97, 99, 100, 101, 102, 103, 105, 106, 107, 108, 109, 111, 113, 114, 116, 117, 118, 119, 120, 121, 122, 123, 124, 126, and complements thereof, and an introduced second nucleic acid molecule encoding an enzyme selected from the group consisting of FatB2 and KAS.

The present invention includes and provides a transformed plant comprising an introduced first nucleic acid molecule comprising encoding a polypeptide having an amino acid selected from the group consisting of SEQ ID NOs: 86, 88, 89, 90, 91, 92, 94, 96, 98, 104, 110, 112, 115, 125, and 127, and an introduced second nucleic acid molecule encoding an enzyme selected from the group consisting of FatB2 and KAS.

The present invention includes and provides a method for increasing the relative percentage of medium chain length fatty acids in a plant comprising: (A) transforming a plant with a nucleic acid molecule, the nucleic acid molecule having a promoter region which functions in plant cells to cause the production of an mRNA molecule, wherein the promoter region is linked to nucleic acid molecule comprising a nucleic acid sequence selected from the group consisting of SEQ ID NOs: 85, 87, 93, 95, 97, 99, 100, 101, 102, 103, 105, 106, 107, 108, 109, 111, 113, 114, 116, 117, 118, 119, 120, 121, 122, 123, 124, and 126, which is linked to a 3' non-translated sequence that functions in the plant cells to cause termination of transcription and addition of polyadenylated ribonucleotides to a end of the mRNA sequence; and (B) growing the transformed plant.

The present invention includes and provides a method for increasing the relative percentage of medium chain length fatty acids in a plant comprising: (A) transforming a plant with a nucleic acid molecule, the nucleic acid molecule having a promoter region which functions in plant cells to cause the production of an mRNA molecule, wherein the promoter region is linked to nucleic acid molecule encoding a polypeptide having an amino acid sequence selected from the group consisting of SEQ ID NOs: 86, 88, 89, 90, 91, 92, 94, 96, 98, 104, 110, 112, 115, 125, and 127, which is linked to a 3' non-translated sequence that functions in the plant cells to cause termination of transcription and addition of polyadenylated ribonucleotides to a 3' end of the mRNA sequence; and (B) growing the transformed plant.

The present invention includes and provides a method of producing a plant having increased DAGAT activity comprising: (A) transforming the plant with a nucleic acid molecule, wherein the nucleic acid molecule comprises a promoter region, wherein the promoter region is linked to a nucleic acid sequence that encodes a polypeptide having an amino acid sequence selected from the group consisting of SEQ ID NOs: 86, 88, 89, 90, 91, 92, 94, 96, 98, 104, 110, 112, 115, 125, and 127; and, (B) growing the plant.

The present invention includes and provides a method of producing a plant having increased mole percent of medium chain fatty acids comprising: (A) transforming the plant with a nucleic acid molecule, wherein the nucleic acid molecule comprises a promoter region, wherein the promoter region is linked to a nucleic acid sequence that encodes a polypeptide having an amino acid sequence selected from the group consisting of SEQ ID NOs: 86, 88, 89, 90, 91, 92, 94, 96, 98, 104, 110, 112, 115, 125, and 127; and, (B) growing the plant.

The present invention includes and provides a transformed plant comprising an introduced nucleic acid molecule comprising a nucleic acid sequence selected from the group consisting of SEQ ID NOs: 85, 87, 93, 95, 97, 99, 100, 101, 102, 103, 105, 106, 107, 108, 109, 111, 113, 114, 116, 117, 118, 119, 120, 121, 122, 123, 124, 126, and complements thereof, wherein the plant produces seed having increased DGAT activity relative to a plant having a similar genetic background but lacking the introduced nucleic acid molecule.

The present invention includes and provides a transformed plant comprising an introduced nucleic acid molecule encodes a polypeptide comprising an amino acid sequence selected from the group consisting of SEQ ID NOs: 86, 88, 89, 90, 91, 92, 94, 96, 98, 104, 110, 112, 115, 125, and 127, wherein the plant produces seed having increased DGAT activity relative to a plant having a similar genetic background but lacking the introduced nucleic acid molecule.

BRIEF DESCRIPTION OF THE DRAWINGS

FIG. 6 presents results of analysis of *Mortierella ramanniana* DAGAT activity in column fractions from a DAGAT purification protocol.

FIG. 13 shows the protein alignments of the two DAGAT proteins identified in *Mortierella ramanniana*. Full-length protein sequence of the 36 kDa candidate is shown while partial sequence of the 36.5 kDa protein is shown.

FIG. 17A shows the results on Yellow-86 agarose chromatography. Solubilized Lipid Body Proteins are applied to a Yellow-86 agarose column in buffer D (Example 17) containing 75 mM KCl. DGAT2 activity is eluted in buffer D containing 500 mM KCl. Protein content is determined according to the method of Bradford (1976) and is reported as milligrams of protein per fraction. DGAT2 activity is reported as nanograms of TAG formed per minute per fraction. Active fractions from four Yellow-86 agarose columns were pooled and concentrated 12 fold by ultrafiltration.

FIG. 17B shows the results by Hydroxyapatite chromatography. The 500 mM KCl concentrate is applied to a Hydroxyapatite column in Buffer G (Example 17) containing 500 mM KCl. The column was washed with equilibration buffer and bound proteins are eluted with 0.1 M potassium phosphate in equilibration buffer. Active fractions present in the flow-through are pooled and diluted 1:3.3 to reduce the KCl concentration to 150 mM.

FIG. 17C shows the results on Heparin chromatography. The diluted hydroxyapatite flow-through is applied to a Heparin column in Buffer G containing 150 mM KCl. The column is washed with equilibration buffer and DGAT2 activity is eluted in a linear gradient of 150-500 KCl in Buffer G followed by a wash of 500 mM KCl in Buffer G. DGAT2 activity is resolved into two peaks.

FIG. 19 shows the sequence alignment of derived DGAT2 polypeptide sequences. The amino acid sequences of the predicted DGAT2 polypeptides are aligned using the Clustal multiple sequence alignment program. Totally conserved residues are shaded black, grey shaded is the consensus of three or more sequences. All sequences are full-length. Residues shown above the alignment are highly conserved signature amino acids found in the motifs D and E of the acyl transferase superfamily (Neuwald, F. (1997) *Current Biology* 7, 465-466 (herein incorporated by reference). In this area DGAT2 and the acyltransferase superfamily sequences co-align, only the shared conserved amino acid residues are shown. Sources: *M. ramanniana*: MrDGAT2A (Accession: AF391089); MrDGAT2B (Accession: AF391090); *S. cerevisiae*: ScDGAT2 (Accession: YOR245C); *C. elegans*: CeDGAT2A (Accession: CAB04533); CeDGAT2B (Accession: AAB04969); CeDGAT2C (Accession: AAD45832); *A. thaliana*: AtDGAT2 (Accession: T45783); *M. musculus*: MmDGAT2 (Accession: BAB22105).

FIG. 25 shows statistical data on percent oil for DGAT2A in $R_2$ soybean (field data and greenhouse data).

FIG. 26 shows statistical data on percent protein for DGAT2A in soybean (field data and greenhouse data).

DETAILED DESCRIPTION OF THE INVENTION

Figure 1:
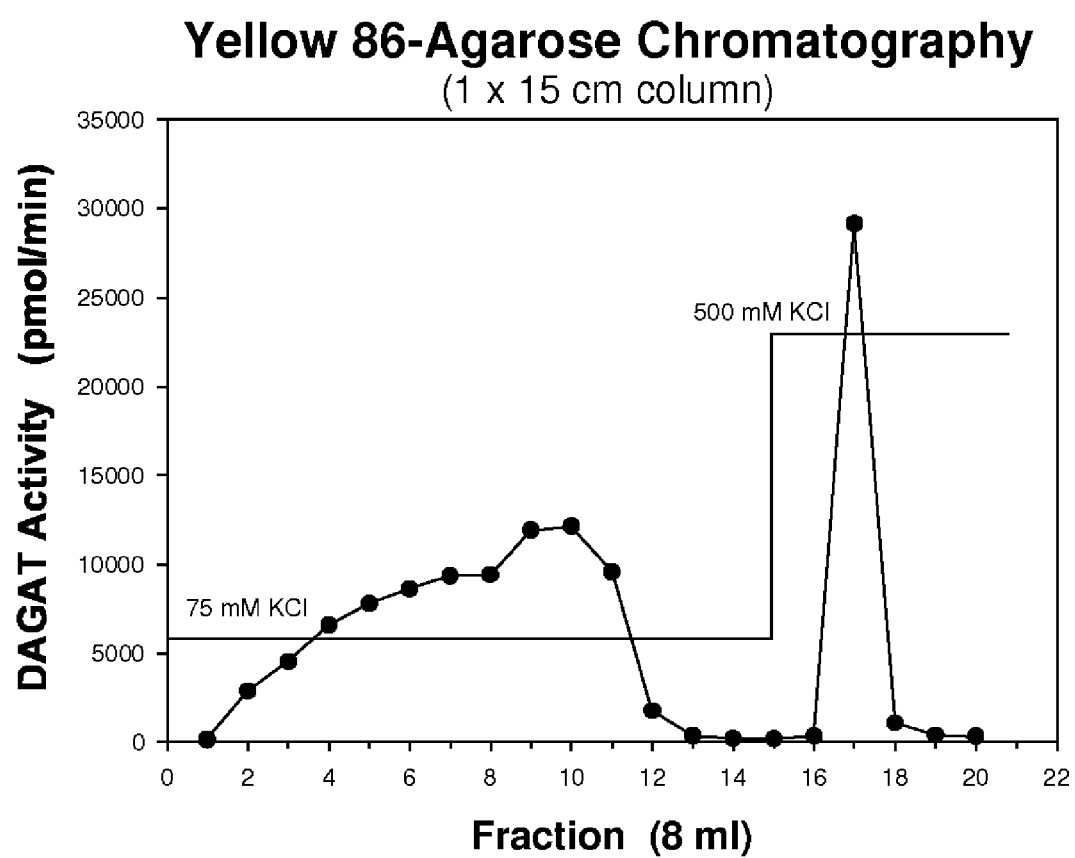
FIG. 1 shows the results of chromatography of *Mortierella ramanniana* DAGAT activity on a Yellow 86-Agarose column.

As used herein, the phrase "oil composition" means the ratio of different fatty acid or oil components within a sample. Such a sample may be a plant or plant part, such as a seed. Such a sample may also be a collection of plant parts.

As used herein, the phrase "percentage content" in a preferred embodiment means the percent by total weight of a particular component, relative to other similar or related components.

As used herein, a diacylglycerol acyltransferase (DGAT) gene of the present invention includes any nucleic acid sequence encoding amino acids, such as protein, polypeptide or peptide, obtainable from a cell source, which demonstrates the ability to catalyze the production of triacylglycerol from 1,2-diacylglycerol and fatty acyl substrates under enzyme reactive conditions. By "enzyme reactive conditions" it is meant that any necessary conditions are available in an environment (i.e., such factors as temperature, pH, lack of inhibiting substances) which will permit the enzyme to function.

The present invention relates to acyl CoA:diacylgycerol acyltransferase (DGAT or DAGAT, alternatively) which catalyzes the final step in the production of triacylglycerol (TAG). More particularly, the present invention includes two polypeptides, which can be purified to near homogenity from the fungus *Mortierella ramanniana*. Using methods known in the art, the polynucleotide sequences encoding these proteins were obtained.

The present invention includes two *Mortierella ramanniana* DGAT2 enzymes having molecular masses of 36 kD (DGAT2A) and 36.5 kD, (DGAT2B) as estimated by gel electrophoresis, and showed a broad activity maximum between pH 6-8. Based on partial peptide sequence information, polymerase chain reaction techniques are used to obtain full-length cDNA sequences encoding the purified proteins. Expression of the cDNAs in insect cells conferred high levels of DGAT activity on the membranes isolated from these cells. The two proteins share 54% homology with each other but are unrelated to the previously identified DGAT gene family (DGAT1, described in application Ser. No. 09/326,203, filed on Jun. 4, 1999 (herein incorporated by reference) which is related to the acyl CoA:cholesterol acyltransferase (ACAT) gene family). DGAT activity of these identified proteins was confirmed by enzyme assay.

The present invention provides a gene family, including members in fungi, plants, and animals, which encode enzymes with DGAT function. To distinguish the two unrelated families the present invention designates this class DGAT2 and refer to the *M. ramanniana* genes as MrDGAT2A and MrDGAT2B.

Figure 19:
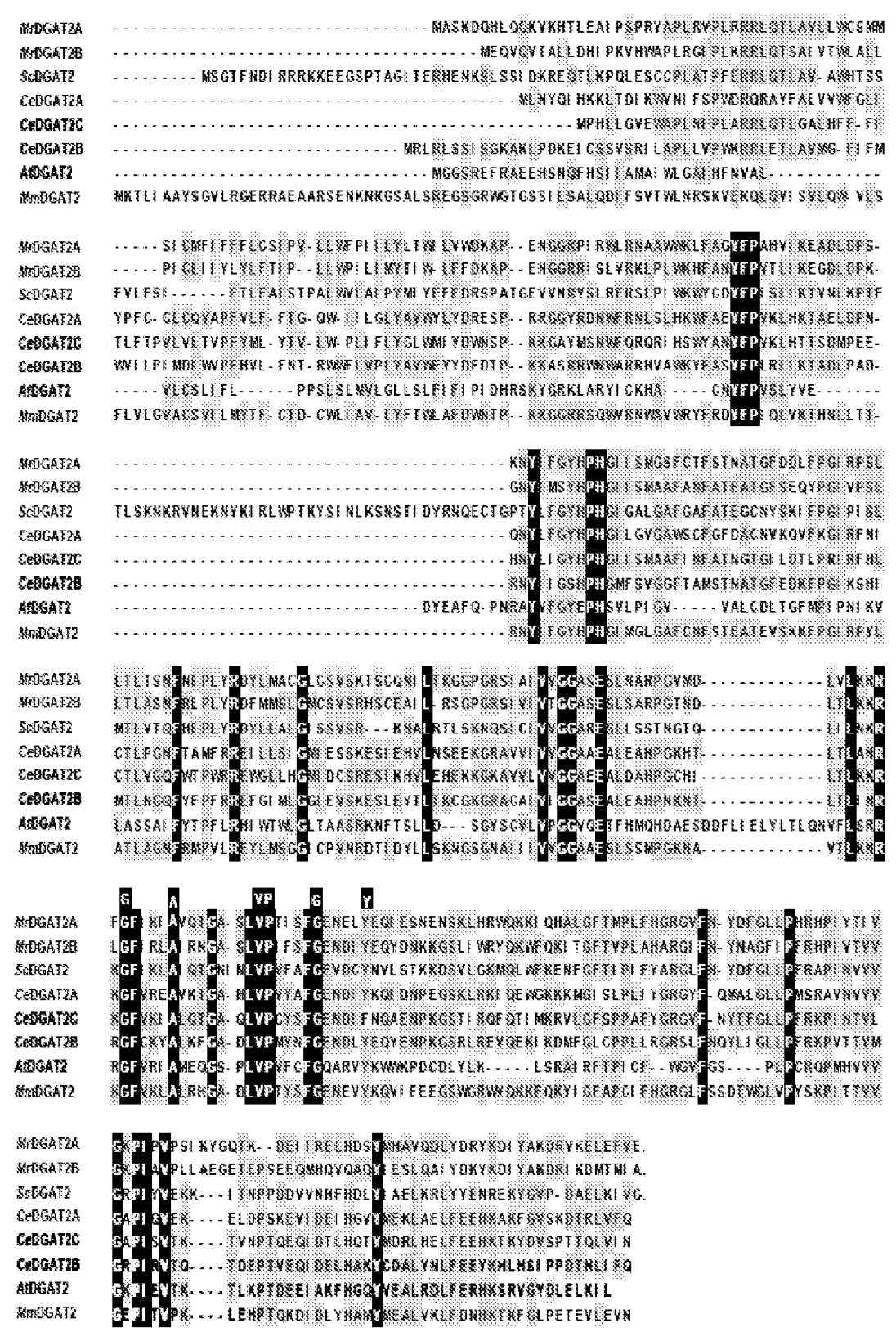

DGAT proteins are isolated from cells of the oleaginous fungus *Mortierella ramanniana*. Following cell lysis, DGAT activity is associated with the lipid body fraction and detergent solubilization is required to release the membrane-bound proteins to permit their purification using traditional chromatographic techniques. A stimulation of DGAT activity in the homogenate is observed following the addition of the detergent Triton X-100. Using a 5-step protocol, two proteins, 36 kD and 36.5 kD by SDS-PAGE, are identified as being associated with DGAT activity. These proteins are named MrDGAT2A and MrDGAT2B, respectively. Final specific activity recoveries of 1.6 and 4.2%, respectively, are reported for the purest, most active fractions containing each protein. Expression of the cloned cDNAs in insect cells confirmed DGAT. Alignment of the two protein sequences indicates they share only 54% sequence similarity (FIG. 19, top two lines).

*M. ramanniana* DGAT in the present invention differs from that reported by Kamisaka, et al. (1997) *J. Biochem.* 121: 1107-1114 (herein incorporated by reference) who identified a 53 kD protein (by SDS-PAGE) as DGAT. The open reading frame of *M. ramanniana* DGAT2A cDNA is terminated 5' and 3' by in-frame stop codons. In addition, other identified DGAT2 polypeptides from other species (FIG. 19) are approximately in the 33-42 kD range. Since apparent molecular weights and predicted molecular weights match approximately, it is likely that the proteins isolated in the present inventions represent unprocessed DGAT2 polypeptides. A 36 kD and a 36.5 kD polypeptide are the only protein bands observed with DGAT activity throughout purification (Example 17).

An unexpected observation of the characterization of *M. ramanniana* DGAT2 proteins isolated from insect cells was the enhanced activity with medium-chain substrates. *Mortierella ramanniana* produces TAG comprised primarily of C18 acyl groups yet more activity was detected when C6-C10 DAGs were provided as the acyl acceptor, especially when a medium chain donor (12:0-CoA) was used. While absolute activity values cannot be compared between samples because of differences in the level of protein expression in different insect cell lines, DGAT2A has greater specificity for medium-chain substrates relative to long-chain substrates that does DGAT2B.

Figure 20:
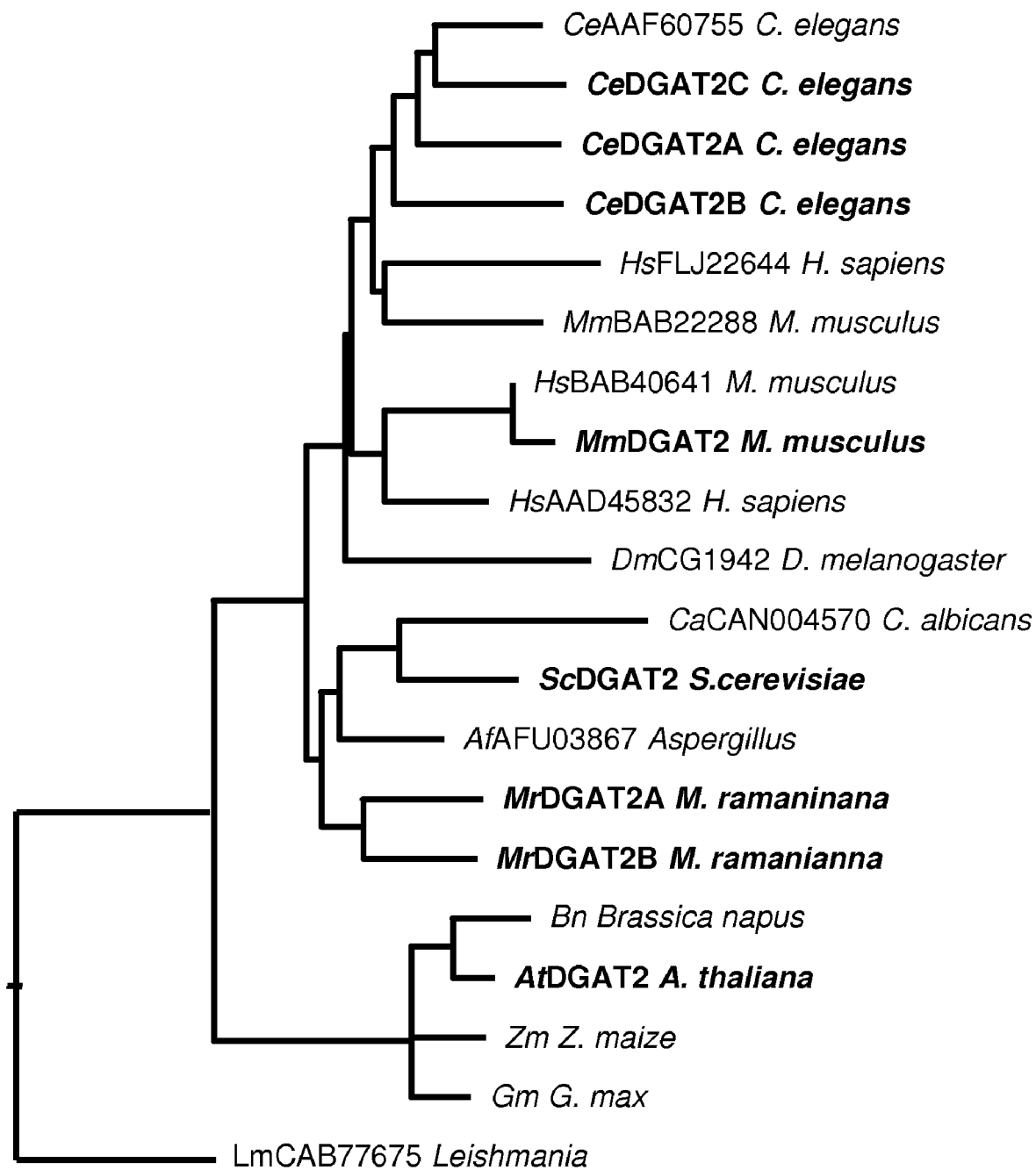
FIG. 20 shows the phylogenetic tree for DGAT2 family members. Several more DGAT2 homologous sequences are added to the assembly of FIG. 19, and a similarity tree is constructed using the DNASTAR software. GenBank accession numbers and the species are shown for each entry. The entries for certain plant sequences are not full length.

A search of the sequence databases using the deduced amino acid sequences of the two *M. ramanniana* clones revealed no homology with the previously identified DGAT1 gene family that is sequence-related to the ACAT gene family. Unidentified DGAT2 homologues are found in many eukaryotic species, namely animals, plants, fungi and *Leishmania*, but are absent from the prokaryotes (FIG. 20). Several conserved signature amino acid residues of motifs D and E of the previously proposed acyltransferase superfamily (Neuwald, F. *Current Biology* 7, 465-466 (1997)) and motif IV of sn-glycerol-3-phosphate acyltransferase consensus (Lewin, T. M. et al. (1999) *Biochemistry* 38:5764-5771) (herein incorporated by reference)), are also conserved in DGAT2 (FIG. 19).

Full-length clones are obtained for several homologues and the expressed proteins were evaluated in insect cells. All of the homologues tested exhibited some level of DGAT activity demonstrating that the genes in this family are related by function. The identification of an additional DGAT gene family is consistent with previous biochemical observations (See, e.g., Katavic, V., et al. (1995) *Plant Physiol.* 108:399-409 and Routaboul J. M., et al. (1999) *Plant Physiol. Biochem.* 37:831-840 (both of which are herein incorporated by reference in its entirety)). First, gene-disruptions of DGAT1 (TAG1 locus) in *Arabidopsis* did not abolish DGAT activity completely or eliminated TAG production in seeds. Second, Smith, S. J., et al. (2000) *Nat. Genet.*, 25:87-90 (herein incorporated by reference in its entirety), working with DGAT1 knock-out mice, concluded there may be an additional DGAT gene present in mammals when experimental data showed that TAG production still occurred in these animals.

In addition to the discovery of a second DGAT gene family described in the present invention, an alternative mechanism for the production of TAG has recently been reported in yeast (see, e.g., Stobart, K., et al. (1997) *Plant J.* 19:645-653; and Dahlqvist, A., et al. (1998) *Advances in Plant Lipid Research,* eds. Sanches, J1, Cerda-Olmedo, E., & Martinez-Force, E., (Universidad de Sevilla, Seville, Spain), pp. 211-214 (both of which are herein incorporated by reference)). This pathway utilizes phospholipid, rather than acyl-coenzyme A, as a substrate for acyl transfer to DAG to produce TAG. The acyl-CoA-independent production of TAG during exponential growth in yeast was associated with the LOR1 gene (Oelkers, P., et al. (2000) *J. Biol. Chem.* 275:15609-15612; and Dahlqvist, A., et al. (2000) *Proc. Natl. Acad. Sci.* USA 97:6487-6492 (both of which are herein incorporated by reference)). A knock out of LOR1 resulted in the complete removal of the acyl-CoA-independent activity and a significant reduction in TAG accumulation. Dahlqvist designated this enzyme phospholipid:diacylglycerol acyltransferase (PDAT) since the enzyme apparently does not discriminate between phospholipid species supplying the acyl group. PDAT is structurally related to the lecithin:cholesterol acyltransferase (LCAT) family and homologues of LOR1 appear to be common in eukaryotes.

Three independent gene families (DGAT1, DGAT2, and PDAT) have been described which encode proteins with the capacity to form TAG, and all three arc present in genomes of eukaryotes. In yeast, all three genes are present but their expression levels vary during different phases of the life cycle (Dahlqvst, A., et al. *Proc. Natl. Acad. Sci. USA* 97:6487-6492 (2000) (herein incorporated by reference)). In mice in which the DGAT1 gene was disrupted, certain tissues appeared to be more affected than others (Smith, S. J., et al. *Nat. Genet.* 25:87-90 (2000) (herein incorporated by reference)). For example, while the Dgat1–/– mice showed only a 20% reduction in total carcass triglyceride, the female mice lost the ability to lactate. Examination of the breast tissue showed a severe reduction in lipid droplets indicating DGAT1 plays a key role in this specific tissue. Dhalqvist et al. (2000) (supra) proposed, in plant seeds, PDAT may be responsible for the selective shuttling of unusual fatty acids out of membrane lipids into TAG. Microsomes isolated from developing seeds of species which produce large amounts of unusual fatty acids in their oil, such as ricinoleic acid in castor and vernolic acid in *C. palaestina*, preferentially incorporate these fatty acids into TAG. TAG is an abundant molecule found in many forms of life most likely because of its high energy density. Additional DGAT polypeptides and nucleic acid sequences are set forth in "Diacylglycerol Acyl Transferase Nucleic Acid Sequences and Associated Products", and naming as inventors Kathryn D. LARDIZABAL, Kristen A. HADFIELD, and Nicholas WAGNER Appl. No. 60/399,427, filed on Jul. 31, 2002, which is herein incorporated by reference in its entirety.

Isolated Proteins, Polypeptides and Polynucleotides

A first aspect of the present invention relates to isolated DAGAT proteins. As used herein, "isolated" means altered "by the hand of man" from its natural state. For example, if it occurs in nature, it has been changed or removed from its original environment, or both. For example, a polynucleotide or a polypeptide naturally present in a living organism is not "isolated," but the same polynucleotide or polypeptide when separated from the materials of its natural state is "isolated". In particular, DAGAT proteins were identified which have a molecular weight between approximately 36 kDa and approximately 37 kDa, according to SDS-PAGE analysis. In particular, DAGAT proteins are provided which have molecular weights of approximately 36 kDa and 36.5 kDa and are obtainable from *Mortierella ramanniana*. Further, the DAGAT proteins have been solubilized. "Solubilization" refers to extraction of the DAGAT enzyme from the membranes in such a way that it then behaves in a manner typical of enzymes that are not membrane-associated.

The DAGAT protein of the subject invention may utilize a variety of acyl substrates in a host cell, including fatty acyl-CoA and fatty acyl-ACP molecules. In addition, the acyl substrates acted upon by the DAGAT may have varying carbon chain lengths and degrees of saturation, although the DAGAT may demonstrate preferential activity towards certain molecules.

Another aspect of the present invention relates to DAGAT polypeptides. Such polypeptides include isolated polypeptides set forth in the Sequence Listing, as well as polypeptides and fragments thereof, particularly those polypeptides which exhibit DAGAT activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76-80 (1994); Birren, et al., *Genome Analysis, 1*: 543-559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403-410 (1990)). The well known Smith Waterman algorithm can also be used to determine identity.

Parameters for polypeptide sequence comparison typically include the following:

Algorithm: Needleman and Wunsch, *J. Mol. Biol.* 48:443-453 (1970)

Comparison matrix: BLOSSUM62 from Hentikoff and Hentikoff, *Proc. Natl. Acad. Sci USA* 89:10915-10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443-453 (1970)

Comparison matrix: matches=+10; mismatches=0.

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

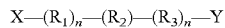

$$X-(R_1)_n-(R_2)-(R_3)_n-Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably SEQ ID NOs: 38 and 45. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in SEQ ID NOs: 37, 44 and 46-72.

Polypeptides of the present invention have been shown to have DAGAT activity and are of interest because DAGAT is involved in the metabolism of cellular glycerolipids, and particularly catalyzes the formation of triacylglycerol from sn-1, 2-diacylglycerol and fatty acyl-CoAs. DAGAT is the only enzyme unique to the triacylglycerol biosynthetic pathway (Coleman R A, (1992) *Methods Enzymol* 209:98-104).

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

Another aspect of the present invention relates to isolated DAGAT polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3 sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

$$X—(R_1)_n—(R_2)—(R_3)_n—Y$$

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably SEQ ID NOs: 37, 44 and 46-72. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the DAGAT peptide sequences. The oligonucleotides are used as primers in polymerase chain reaction (PCR) techniques to obtain partial DNA sequence of DAGAT genes. The partial sequences so obtained are then used as probes to obtain DAGAT clones from a gene library prepared from *Mortierella ramanniana* tissue. Alternatively, where oligonucleotides of low degeneracy can be prepared from particular DAGAT peptides, such probes may be used directly to screen gene libraries for DAGAT gene sequences. In particular, screening of cDNA libraries in phage vectors is useful in such methods due to lower levels of background hybridization.

Typically, a DAGAT sequence obtainable from the use of nucleic acid probes will show 60-70% sequence identity between the target DAGAT sequence and the encoding sequence used as a probe. However, lengthy sequences with as little as 50-60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20-50% deviation (i.e., 50-80% sequence homology) from the sequences used as probe. Oligonucleotide probes can be considerably shorter than the entire nucleic acid sequence encoding an DAGAT enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related DAGAT genes. Shorter probes are often particularly useful for polymerase chain reactions (PCR), especially when highly conserved sequences can be identified. (See, Gould, et al., *PNAS USA* (1989) 86:1934-1938.).

The polynucleotides and polypeptides of the invention can be used, for example, in the transformation of plants, as research reagents, and for the discovery of treatments of and diagnostics for disease, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Plant Constructs and Methods of Use

Of particular interest is the use of the nucleotide sequences in recombinant DNA constructs to direct the transcription or transcription and translation (expression) of the acyltransferase sequences of the present invention in a host plant cell. The expression constructs generally comprise a promoter functional in a host plant cell operably linked to a nucleic acid sequence encoding a diacylglycerol acyltransferase of the present invention and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810-812; Rogers, U.S. Pat. No. 5,378,619). In addition, it may also be preferred to bring about expression of the acyltransferase gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.*, 83:8560-8564 (1986))) and oleosin.

It may be advantageous to direct the localization of proteins conferring DAGAT to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104-126; Clark et al. (1989) *J. Biol. Chem.* 264:17544-17550; della-Cioppa et al. (1987) *Plant Physiol.* 84:965-968; Romer et al. (1993) *Biochem. Biophys. Res Commun.* 196: 1414-1421; and, Shah et al. (1986) *Science* 233:478-481.

Depending upon the intended use, the constructs may contain the nucleic acid sequence which encodes the entire DAGAT protein, or a portion thereof. For example, where antisense inhibition of a given DAGAT protein is desired, the entire DAGAT sequence is not required. Furthermore, where DAGAT sequences used in constructs are intended for use as probes, it may be advantageous to prepare constructs containing only a particular portion of a DAGAT encoding sequence, for example a sequence which is discovered to encode a highly conserved DAGAT region.

The skilled artisan will recognize that there are various methods for the inhibition of expression of endogenous sequences in a host cell. Such methods include, but are not limited to antisense suppression (Smith, et al. (1988) *Nature* 334:724-726), co-suppression (Napoli, et al. (1989) *Plant Cell* 2:279-289), ribozymes (PCT Publication WO 97/10328), and combinations of sense and antisense Waterhouse, et al. (1998) *Proc. Natl. Acad. Sci. USA* 95:13959-13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the diacylglycerol acyltransferase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the DAGAT sequences directly from the host plant cell plastid. Such constructs and methods are known in the art and are generally described, for example, in Svab, et al. (1990) *Proc. Natl. Acad. Sci. USA* 87:8526-8530 and Svab and Maliga (1993) *Proc. Natl. Acad. Sci. USA* 90:913-917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a DAGAT nucleic acid sequence.

Plant expression or transcription constructs having a plant DAGAT as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of plant DAGAT constructs in plants which have been genetically engineered to produce a particular fatty acid in the plant seed oil, where TAG in the seeds of nonengineered plants of the engineered species, do not naturally contain that particular fatty acid. Thus, the expression of novel DAGAT in plants may be desirable for the incorporation of unique fatty acyl groups into the sn-3 position.

Further plant genetic engineering applications for DAGAT proteins of this invention include their use in preparation of structured plant lipids which contain TAG molecules having desirable fatty acyl groups incorporated into particular positions on the TAG molecules.

It is contemplated that the gene sequences may be synthesized, either completely or in part, especially where it is desirable to provide plant-preferred sequences. Thus, all or a portion of the desired structural gene (that portion of the gene which encodes the DAGAT protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" DAGATs from a variety of plant sources. Homologous sequences are found when there is an identity of sequence, which may be determined upon comparison of sequence information, nucleic acid or amino acid, or through hybridization reactions between a known DAGAT and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature protein. (See generally, Doolittle, R. F., *OF URFS and ORFS* (University Science Books, CA, 1986.)

Thus, other DAGATs may be obtained from the specific exemplified *Mortierella* protein preparations and sequences provided herein. Furthermore, it will be apparent that one can obtain natural and synthetic DAGATs, including modified amino acid sequences and starting materials for synthetic-protein modeling from the exemplified DAGATs and from DAGATs which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

For immunological screening, antibodies to the DAGAT protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the *Mortierella ramanniana* DAGAT. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

Many plants utilize DAGAT proteins in production of storage TAG in seeds, and thus any such plant species can be considered as a source of additional DAGAT proteins. Plants having high amounts of TAG with palmitate or stearate acyl groups at the sn-1 and sn-3 positions with oleate or linoleate at sn-2 are preferred candidates to obtain plant DAGATs capable of incorporating saturated fatty acids at the sn-3 position of TAG which show special selectivity for synthesis of structured TAG of the form S-U-S, where S represents a saturated fatty acid and U represents an unsaturated fatty acid. For example, oils from several tropical plants including cocoa, illipe, sat, shea, and *Garcinia* species such as kokum have been shown to accumulate high amounts of TAG in this form.

Plants having significant medium-chain fatty acids in their seed oils are preferred candidates to obtain plant DAGATs capable of incorporating medium-chain fatty acids into the sn-3 position of TAG. Several species in the genus *Cuphea* accumulate triglycerides containing medium-chain fatty acids in their seeds, e.g., *procumbens, lutea, hookeriana, hyssopifolia, wrightii* and *inflata*. Another natural plant source of medium-chain fatty acids are seeds of the Lauraceae family. In addition to the exemplified California Bay (*Umbellularia californica*), Pisa (*Actinodophne hookeri*), Sweet Bay (*Laurus nobilis*) and *Cinnamomum camphora* (camphor) accumulate medium-chain fatty acids. Other plant sources include Ulmaceae (elm), Palmae, Myristicaceae, Simarubacene, Vochysiaceae, and Salvadoraceae.

Also of particular interest are DAGATs from plant species which incorporate unusual long-chain fatty acids in the storage TAG. For example nasturtium and meadowfoam contain 22:1 acyl groups in the seed.

It should also be noted that plant DAGATs from a variety of sources can be used to investigate TAG biosynthesis events of plant lipid biosynthesis in a wide variety of in vivo applications. Because all plants appear to synthesize lipids via a common metabolic pathway, the study and/or application of one plant DAGAT to a heterologous plant host may be readily achieved in a variety of species. In other applications, a plant DAGAT can be used outside the native plant source of the DAGAT to enhance the production and/or modify the composition of the TAG produced or synthesized in vitro.

In addition to isolation of other DAGATs, it is considered that genes for other related acyltransferase proteins may also be obtained using sequence information from the DAGAT and related nucleic acid sequences. For example, other acyltransferase enzymes are involved in plant lipid biosynthesis, including plastidial DAGAT, mitochondrial DAGAT, lysophosphosphatidylcholine acyltransferase (LPCAT), lysophosphosphatidvlserine acyltransferase (LPSAT), lysophosphosphatidylethanolamine acyltransferase (LPEAT) phosphatidylcholine diacylglyercol acyltransferase (PDAT), and lysophosphosphatidylinositol acyltransferase (LPIAT). While many of these enzymes catalyze acyltransferase reactions involving the sn-2 position of lysophospholipids, the genes encoding these sequences may also be related to the plant acyl-CoA DAGAT sequences of the instant invention and obtainable therefrom.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, such as Northern or Southern blots, or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266-285). A useful probe and appropriate hybridization and washing conditions having been identified as described above, cDNA or genomic libraries are screened using the labeled sequences and optimized conditions.

The nucleic acid sequences associated with plant DAGAT proteins will find many uses. For example, recombinant constructs can be prepared which can be used as probes, or which will provide for expression of the DAGAT protein in host cells to produce a ready source of the enzyme and/or to modify the composition of triglycerides found therein. Other useful applications may be found when the host cell is a plant host cell, either in vitro or in vivo. For example, by increasing the amount of a respective medium-chain preferring DAGAT available to the plant TAG biosynthesis pathway, an increased percentage of medium-chain fatty acids may be obtained in the TAG. In a like manner, for some applications it may be desired to decrease the amount of DAGAT endogenously expressed in a plant cell by anti-sense technology. For example, to allow for more opportunity for an inserted foreign DAGAT to transfer saturated acyl groups, or medium-chain or unusual longer-chain fatty acyl groups to sn-3 position, decreased expression of a native *Brassica* long-chain preferring DAGAT may be desired.

As discussed above, nucleic acid sequence encoding a plant DAGAT of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired plant DAGAT nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant DAGAT of this invention may be combined with other non-native, or "heterologous", sequences in a variety of ways. By "heterologous" sequences is meant any sequence which is not naturally found joined to the plant DAGAT, including, for example, combinations of nucleic acid sequences from the same plant which are not naturally found joined together.

The DNA sequence encoding a plant DAGAT of this invention may be employed in conjunction with all or part of the gene sequences normally associated with the DAGAT. In its component parts, a DNA sequence encoding DAGAT is combined in a DNA construct having, in the 5' to 3' direction of transcription, a transcription initiation control region capable of promoting transcription and translation in a host cell, the DNA sequence encoding plant DAGAT and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant DAGAT foreign to the wild-type cell present therein, for example, by having a recombinant nucleic acid construct encoding a plant DAGAT therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Saccharomyces cer-*

*evisiae* including genes such as beta-galactosidase, T7 polymerase, tryptophan E and the like.

The methods used for the transformation of the host plant cell are not critical to the present invention. The transformation of the plant is preferably permanent, i.e. by integration of the introduced expression constructs into the host plant genome, so that the introduced constructs are passed onto successive plant generations. The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, *Agrobacterium* infection, liposomes or microprojectile transformation. The skilled artisan can refer to the literature for details and select suitable techniques for use in the methods of the present invention.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A.* (1980) 77:7347-7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (*Plant Mol. Biol.* (1990) 14:269-276), wherein the pRiHRI (Jouanin, et al., *Mol. Gen. Genet.* (1985) 201:370-374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the diacylglycerol acyltransferase of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the DAGAT expression construct, or alternatively, transformed plants, one expressing the DAGAT construct and one expressing the second construct, can be crossed to bring the constructs together in the same plant.

Other Constructs and Methods of Use

In a preferred embodiment, expression or overexpression of a polypeptide of the present invention in a plant provides in that plant, relative to an untransformed plant with a similar genetic background, is associated with an increase of a medium chain length fatty acids comprising about 8 to 12 carbon atoms in length.

In a preferred embodiment, expression or overexpression of a polypeptide of the present invention in a plant provides in that plant, relative to an untransformed plant with a similar genetic background, is associated with an alteration of the oil composition.

In a preferred embodiment, expression or overexpression of a polypeptide of the present invention in a plant provides in that plant, relative to an untransformed plant with a similar genetic background, is associated with an increase in total oil.

In a preferred embodiment, expression or overexpression of a polypeptide of the present invention in a plant provides in that plant, relative to an untransformed plant with a similar genetic background, is associated with an increase of a percent content change of a particular component.

In a preferred embodiment, expression or overexpression of a polypeptide of the present invention in a plant provides in that plant, relative to an untransformed plant with a similar genetic background, is associated with an increase in DGAT activity.

In a preferred embodiment, expression or overexpression of a polypeptide of the present invention in a plant provides in that plant, relative to an untransformed plant with a similar genetic background, is associated with an increase in the mole percentage of medium chain-length fatty acids.

In a preferred embodiment, expression or overexpression of a polypeptide of the present invention in a plant provides in that plant, relative to an untransformed plant with a similar genetic background, an increase in DGAT activity associated with at least a 1.5 fold increase in the production of triacylglycerol (TAG). In a more preferred embodiment, increased DGAT activity is associated with at least a 2 fold increase in TAG production relative to an untransformed plant with a similar genetic background. In an even more preferred embodiment, increased DGAT activity is associated with at least a 2.5 fold increase in TAG production relative to an untransformed plant with a similar genetic background. In an even more preferred embodiment, increased DGAT activity is associated with at least a 3 fold increase in TAG production relative to an untransformed plant with a similar genetic background. In a most preferred embodiment, increased DGAT activity is associated with at least a 3.5 fold increase in TAG production relative to an untransformed plant with a similar genetic background.

In a preferred embodiment, expression or overexpression of a polypeptide of the present invention in a plant provides in that plant, relative to an untransformed plant with a similar genetic background, is associated with an increase of greater than about 2 mole percent of medium chain-length fatty acid content relative to an untransformed plant with a similar genetic background. In a more preferred embodiment, expression or overexpression of a polypeptide of the present invention in a plant is associated with an increase of greater than about 5 mole percent of medium chain-length fatty acid content relative to an untransformed plant with a similar genetic background. In an even more preferred embodiment, expression or overexpression of a polypeptide of the present invention in a plant is associated with an increase of greater than about 7.5 mole percent of medium chain-length fatty acid content relative to an untransformed plant with a similar genetic background. In an even more preferred embodiment, expression or overexpression of a polypeptide of the present invention in a plant is associated with an increase of greater than about 10 mole percent of medium chain-length fatty acid content relative to an untransformed plant with a similar genetic background. In a most preferred embodiment, expression or overexpression of a polypeptide of the present invention in a plant is associated with an increase of greater than about 12, 15 or 17 mole percent of medium chain-length fatty acid content relative to an untransformed plant with a similar genetic background.

The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds and flowers. A preferred organ is a seed. For example the levels of products may be increased in one or more of the tissues and organs of a plant including without limitation: roots, tubers, stems, leaves, stalks, fruit, berries, nuts, bark, pods, seeds and flowers.

In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

The invention also relates to vectors that include a polynucleotide or polynucleotides of the invention, host cells that are genetically engineered with vectors of the invention and the production of polypeptides of the invention by recombinant techniques. Cell free translation systems can be employed to produce such protein using RNAs derived from the DNA constructs of the invention.

For recombinant production, host cells can be genetically engineered to incorporate expression systems or portions thereof or polynucleotides of the present invention. Introduction of a polynucleotide into a host cell can be effected by methods described in many standard laboratory manuals, such as Davis et al., Basic Methods in Molecular Biology, (1986) and Sambrook et al, Molecular Cloning: A Laboratory Manual, $2^{nd}$ Edition, Cold Spring Harbor Laboratory Press, Cold Spring Harbor N.Y. (1989). Such methods include, but are not limited to, calcium phosphate transfection, DEAE dextran mediated transfection, transvection, microinjection, cationic lipid-mediated transfection, electroporation, transduction, scrape loading ballistic introduction and infection.

Representative examples of appropriate hosts include bacterial cells, such as streptococci, staphylococci, enterococci, *E. coli, streptomyces*, and *Bacillus subtilis* cells; fungal cells, such as yeast cells and *Aspergillus* cells; insect cells, such as *Drosophila* S2 and *Spodoptera* Sf9 cells; animal cells such as CHO, COS, HeLa, C127, 3T3, BHK, 293 and Bowes melanoma cells; and plant cells as described above.

A variety of expression systems can be used to produce the polypeptides of the invention. Such vectors include, but are not limited to, chromosomal, episomal, and virus derived vectors, for example vectors from bacterial plasmids, bacteriophage, transposons, yeast episomes, insertion elements, yeast chromosomal elements, viruses such as baculoviruses, papova viruses, such as SB40, vaccinia viruses, adenoviruses, fowl pox viruses, pseudorabies viruses and retroviruses, and vectors derived from combinations of such viruses, such as those derived from plasmid and bacteriophage genetic elements, such as cosmids and phagemids. The expression system constructs may contain control regions that regulate as well as engender expression. Generally, any system or vector which is suitable to maintain, propagate or express polynucleotides and/or to express a polypeptide in a host can be used for expression. The appropriate DNA sequence can be inserted into the chosen expression by any of a variety of well-known and routine techniques, such as, for example, those set forth in Sambrook et al, *Molecular Cloning, A Laboratory Manual*, (supra).

Appropriate secretion signals, either homologous or heterologous, can be incorporated into the expressed polypeptide to allow the secretion of the protein into the lumen of the endoplasmic reticulum, the periplasmic space or the extracellular environment.

The polypeptides of the present invention can be recovered and purified from recombinant cell cultures by any of a number of well known methods, including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. It is most preferable to use high performance liquid chromatography (HPLC) for purification. Any of the well known techniques for protein refolding can be used to regenerate an active confirmation if the polypeptide is denatured during isolation and/or purification.

This invention is also related to the use of the polynucleotides of the invention as diagnostic reagents. Detection of a mutated form of a gene can be used as a diagnostic tool that to assist in the diagnosis of a disease or of susceptibility to a disease which results from under-expression, over-expression or altered expression of the gene. A variety of well known techniques can be used to detect, at the DNA level, an individual who has a mutation in the gene.

Nucleic acids for diagnosis may be obtained from an infected individual's cells and tissues, such as bone, blood, muscle, cartilage and skin. Genomic DNA can be used directly for detection or can be amplified prior to analysis using PCR or other amplification techniques. RNA or cDNA can also be used in the same manner. Deletions and insertions can be detected by a change in the size of the amplified product as compared to the genotype of a reference sequence. Point mutations can be identified by hybridizing amplified DNA to labeled polynucleotide sequences of the invention. Sequences that are perfectly matched can be distinguished from mismatched duplexes by RNase digestion or by differences in the melting temperature. Sequence differences can also be detected, at the DNA level, by comparing electrophoretic mobility of DNA fragments in gels, with or without denaturing agents; or by direct DNA sequencing (See, for example, Myers et al., *Science* 230: 1242 (1985)). A sequence change at a particular location can also be detected using nuclease protection assays, such as RNase and S1 protection or a chemical cleavage method (See, for example, Cotton et al., *Proc. Natl. Acad. Sci., USA*, 85: 43974401 (1985). It is anticipated that an array of oligonucleotide probes comprising a DAGAT nucleotide sequence or fragments thereof can be used for screening, particularly for genetic mutations. Array technology methods are well known and are useful in gene expression, genetic linkage and genetic variability analyses (See, for example, M. Chee et al., *Science*, 274: 610-613 (1996)).

The invention further provides a method for diagnosing or determining a susceptibility to a disease associated with DAGAT activity, particularly diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis, by determining from a sample an abnormally altered level of polypeptide or NA. Altered expression can be measured at the RNA level by any of the techniques well known in the art for quantitation of polynucleotides, including, but not limited to, amplification, PCR, RT-PCR. RNase protection, Northern blotting and other hybridization methods. Diagnostic assays are also contemplated which detect levels of protein expression including, but not limited to radioimmunoassays, competitive-binding assays, Western Blot analysis and ELISA assays.

The nucleotide sequences of the present invention can also be used in chromosome identification.

The polypeptides of the invention or variants thereof, or cells expressing them can be used as an immunogen to produce antibodies which are immunospecific for polypeptides of the present invention. "Immunospecific" means that the antibodies have a substantially greater affinity for the polypeptides of the present invention as compared to the affinity of the antibodies for other related polypeptides. "Antibodies" includes monoclonal and polyclonal antibodies, including chimeric, single chain, simianized, humanized, resurfaced and other types of complementarity determining region (CDR) replaced antibodies, as well as Fab fragments, including products of an Fab immunoglobulin expression library.

Antibodies can be obtained by administering the polypeptides or epitope bearing fragments, analogs or cells to an animal, preferably non-human, using routine protocols. Any of the well known techniques continuous cell culturing techniques can be used to prepare monoclonal antibodies including hybridoma technology (See for example, Kohler, G. and Milstein, C., *Nature* 256:495-497 (1975)); trioma technology; human B-cell hybridoma technology (Kozbor et al., *Immunology Today* 4:72 (1983)); and the EBV-hybridoma technology (Cole et al., *Monoclonal Antibodies and Cancer Therapy*, Alan R. Liss. 77-96, (1985)).

Single chain, humanized, resurfaced, simianized and other types of CDR replaced antibodies can be produced according to techniques which are well known in the art.

The described antibodies can be used to isolate or identify clones that express the polypeptide or to purify polypeptides by affinity chromatography. The antibodies can also be used to treat diseases associated with DAGAT activity, particularly diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis.

The present invention also relates to genetically engineered soluble fusion proteins which comprises a polypeptide of the present invention, or a fragment thereof, fused to portions of the constant regions of the heavy or light chains of immunoglobulins of the various subclasses (IgG, IgM, IgA and IgE). Preferably the constant portion of the heavy chain of human IgG, particularly IgG1, is used with fusion at the hinge region. Particularly preferred is the use of Fc portion. (See, for example, WO 94/29458 and WO 94/22914)

Polypeptides of the present invention can also be used to identify compounds which bind to the polypeptide, and in particular, inhibit or stimulate the activity of the polypeptide by binding. The binding of small molecule substrates and ligands can be assessed in, for example, cells, cell-free preparations, chemical libraries, and natural product mixtures. The agonists or antagonists/inhibitors can be natural substrates or ligands or can be structural or functional mimetics thereof. See, for example, Coligan et al., Curr Prot in Immuno, 1(2): Chapter 5 (1991).

The invention also provides a method for screening compounds to identify those compounds that bind to the polypeptides or polynucleotides of the present invention and particularly those compounds that enhance (agonist) or inhibit (antagonist) the action of polypeptides or polynucleotides of the invention. High throughput screening techniques can be used. As an example, to screen for agonists or antagonists, a synthetic reaction mix, a cellular compartment, such as a membrane, cell envelope or cell wall, or a preparation of any of these, comprising a polypeptide of the invention and a labeled substrate or ligand of such polypeptide is incubated in the absence or presence of a candidate compound that is being screening. The ability of the candidate compound to agonize or antagonize a polypeptide of the invention is detected by a decrease in binding of the labeled ligand or a decrease in the production of product from the substrate. Candidate compounds that bind gratuitously, without inducing the effects of a polypeptide of the invention, are most likely to be good antagonists. On the other hand, compounds that bind well and increase the rate of product production from substrate are considered agonists. The detection of the rate or level of production of product from substrate can be enhanced by using a reporter system such as, but not limited to, colormetric labeling, inclusion of a reporter gene that is responsive to changes in polynucleotide or polypeptide activity and binding assays known in the art.

Competitive assays that combine a polypeptide of the invention and a potential antagonist with a compound that binds the polypeptide, natural substrates or ligands, or substrate or ligand mimetics can also be used to screen for antagonist compounds. The polypeptide of the invention can be label, such as by radioactivity or colorimetric compound, such that the number of such polypeptide molecules that bound to the binding molecule or converted to product can be determined to assess the effectiveness of the potential antagonist.

Potential antagonists can include, but are not limited to, small organic molecules, peptides, polypeptides and antibodies that bind to a polynucleotide or polypeptide of the invention and thereby inhibit or partially or completely block its activity. Antagonists can also include small organic molecules, peptides, polypeptides and antibodies that bind to the same site on a binding molecule without inducing the activities that are induced by a polypeptide of the invention, thereby preventing the action of the polypeptide by blocking it from binding. Potential antagonists also include small molecules that bind to and occupy the binding site of the polypeptide thereby preventing the polypeptide from binding to cellular binding molecules, so as to prevent or reduce normal biological activity of the polypeptide. Examples of such small molecules include, but are not limited to, small organic molecules, peptides and peptide like molecules. Other potential antagonists include antisense molecules (see, for example, Okano, J. Neurochem, 56: 560 (1991); Oligodeoxynucleotides as Antisense Inhibitors of Gene Expression, CRC Press, Boca Raton, Fla. (1988)).

Antagonists and agonists of DAGAT activity are particular useful as DAGAT is important in the formation of chylomicra in small intestine, VLDL in liver, and for storage of energy as triacylglycerol in adipose tissue. Thus, inhibiting DAGAT activity in small intestine, liver, and adipose tissues will reduce lipid absorption and plasma triglyceride levels and will decrease adipogenesis. Further, hypertriglyceridemia has been shown to be an independent risk factor for atherosclerosis (Kugiyama, K., et al., (1998) Circulation 97:2519-2526,) and is a marker for increased risk of coronary artery disease and can serve as a marker for several atherogenic factors (Grundy, S. M., (1998) Am. J. Cardiol, 81:18 B-25B). Compounds that inhibit DAGAT activity are also useful in controlling intestinal fat absorption, altering TAG rich lipoprotein secretion and controlling serum TAG, and reducing adipogenesis (Owen M R, et al. (1997) Biochem J 323:17-21, Jamdar S C and Cao W F (1995) Biochim Biophys Acta 1255:237-243). Furthermore, the diacylglycerol substrate of DAGAT is a signal transducing molecule within the cell and is a known modulator of protein kinase C activity. Altered cellular diacylglycerol concentration and PROTEIN KINASE C activity has been associated with cancer (da Costa et al., (1993) J. Biol. Chem. 268:2100-2105), diabetes (Koya D and King G L (1998) Diabetes 47:859-866), heart failure (Okumura, et al., (1991) J. Mol. Cell. Cardiol. 23:409-416), adipocyte (Baldo et al., (1995) J. Lipid Res., 36:1415-1426), leukemia and skin carcinoma cells (Goldkorn T., and Ding, T. (1997) Adv. Exp. Med. Biol., 400A:461-472), and rat fibroblasts (Pai et al., (1991) Proc. Natl. Acad. Sci., 88:598-602). As such, agonists and antagonists of the invention are particularly useful in treating or ameliorating diseases associated with DAGAT activity, including diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis.

The invention also relates to compositions comprising the polynucleotide or the polypeptide, or variants, agonists or antagonists thereof. The polypeptides of the invention can be used in combination with a sterile or non-sterile carrier or carriers for use with cells, tissues or organisms, such as a pharmaceutical carrier suitable for administration to a subject. Such compositions comprise, for example, a therapeutically effective amount of a polypeptide or other compound of the invention and a pharmaceutically acceptable carrier or excipient. Such carriers include, but are not limited to, saline, buffered saline, dextrose, water, glycerol, ethanol and combinations thereof. The formulation should be consistent with the mode of administration. The invention further relates to diagnostic and pharmaceutical packs or kits comprising one or more containers filled with one or more of the ingredients of the aforementioned compositions of the invention.

Polypeptides and other compounds of the invention may be administered alone or in combination with other compounds.

The pharmaceutical compositions can be administered in any effective, convenient manner including, but not limited to, topical, oral, anal, vaginal, intravenous, intraperitoneal, intramuscular, subcutaneous, intranasal or intradermal routes.

The required dosage range will depend on the peptide or other compound of the present invention that is used, the route of administration, the nature of the formulation, the nature of the subject's condition and the judgment of the practitioner. Suitable dosages will generally be in the range of approximately 0.1 to 100 µg/kg. The large variation in the dosage is expected due to the variety of compounds and the differences in the efficacy of administration. As an example, it is expected that oral administration would require higher dosages than intravenous administration. The skilled practitioner can determine the appropriate dosage using standard empirical methods.

Polypeptides can also be generated endogenously in the subject, which is generally referred to as "gene therapy" For example, cells from a subject may be engineered with a polynucleotide, such as a DNA or RNA, to encode a polypeptide, ex vivo, and by the use of a retroviral plasmid vector. The cells are then introduced into the subject.

The polynucleotide and polypeptide sequences can also be used to identify additional sequences which are homologous to the sequences of the present invention. The most preferable and convenient method is to store the sequence in a computer readable medium, for example, floppy disk, CD ROM, hard disk drives, external disk drives and DVD, and then to use the stored sequence to search a sequence database with well known searching tools. Examples of public databases include the DNA Database of Japan (DDBJ) (http://www.ddbj.nig.ac.jp/); Genebank (http://www.ncbi.nlm.nih.gov/web/Genbank/Index.htlm); and the European Molecular Biology Laboratory Nucleic Acid Sequence Database (EMBL) (http://www.ebi.ac.uk/ebi_docs/embl_db.html). A number of different search algorithms are available to the skilled artisan, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, Trends in Biotechnology, 12: 76-80 (1994); Birren, et al.,

*Genome Analysis*, 1: 543-559 (1997)). Additional programs are available in the art for the analysis of identified sequences, such as sequence alignment programs, programs for the identification of more distantly related sequences, and the like, and are well known to the skilled artisan.

The invention now being generally described, it will be more readily understood by reference to the following examples which are included for purposes of illustration only and are not intended to limit the present invention.

EXAMPLES

Example 1

Diacylglycerol Acyltransferase (DAGAT) Assays

Methods to assay for DAGAT activity in non-solubilized or solubilized protein preparations are described for *Mortierella ramanniana*.

A. Non-Solubilized Samples

DAGAT activity is assayed with 3.67 µM 1-$^{14}$C-18:1-Coenzyme A (53.5-54.5 Ci/mole, New England Nuclear, Boston, Mass.) and 1.5 mM 1,2-18:1 diacylglycerol (DAG) (Sigma D-0138, prepared as a 150 mM stock in 2-methoxyethanol) in a buffer containing 10 mM potassium phosphate (pH 7.0), 100-150 mM KCl, and 0.1% TX-100 (w/v) in a total volume of 100 µl as similarly described by Kamisaka et al. (1993) supra and Kamisaka et al. (1994) supra. Assays are performed at 30° C. for 5 min and terminated with the addition of 1.5 ml of heptane:isopropanol:0.5M $H_2SO_4$ (10:40:1, v/v/v). If necessary, samples may be diluted with buffer prior to assay in order to maintain a linear rate of product formation during the assay.

B. Solubilized Samples

The assay is performed as described for non-solubilized samples with the following changes: the amount of 1,2-18:1 DAG is reduced to 0.5 mM, the amount of Triton X-100 is increased to 0.2%, and the KCl concentration is maintained between 100-125 mM. It is also necessary to include L-α-phosphatidic acid (Sigma P-9511, prepared as a 50 mM stock in 1% Triton X-100 (w/v)) to recover activity following solubilization with detergent as described by Kamisaka et al. (1996 and 1997) supra, with the following modifications of the protocol. The use of 300 µM phosphatidic acid rather than 500 µM gives a higher stimulation of DAGAT activity following treatment by Triton X-100. In addition, the DAGAT activity is sensitive to the amount of KCl introduced in the assay with the optimum level between 100-125 mM. Assays are performed at 30° C. for 5-30 minutes and terminated as described for non-solubilized samples.

C. Processing of Sample Assays

After the assays are terminated, the samples can be stored at 4° C. for processing at a later date or immediately processed by addition of 0.1 ml 1 M $NaHCO_3$ followed by 1 ml of heptane containing 15 nmoles/ml triolein as a carrier for extraction. The samples are vortexed and, after separation of aqueous and organic phases, the upper organic phase is removed to a new glass vial and washed with 1 ml 1M NaCl. Forty percent of the final organic phase is removed for liquid scintillation counting and the remaining organic phase is transferred to a clean vial and evaporated to dryness under nitrogen gas. The residue is resuspended in 45 µl hexane and spotted onto a silica gel-G, glass, thin-layer chromatography (TLC) plate with a pre-adsorbent loading zone (Analtech #31011, Newark, Del.). The TLC plate is developed in hexane:diethyl ether:acetic acid (50:50:1, v/v/v) to the top then dried and scanned by a radio-image analyzer (AMBIS 3000, San Diego, Calif.) to determine the portion of radioactivity incorporated into triacylglycerol. Activity is reported in units as pmole/min.

Example 2

*Mortierella ramanniana* Culture Conditions

*Mortierella ramanniana* is cultured by inoculating 1 liter of Defined Glucose Media (30 g glucose, 1.5 g $(NH_4)_2SO_4$, 3 g $K_2HPO_4$, 0.3 g $MgSO_4.7H_2O$, 0.1 g NaCl, 5 g $CH_3COONa.3H_2O$, 10 mg $FeSO_4.7H_2O$, 1.2 mg $CaCl_2.2H_2O$, 0.2 mg $CuSO_4.5H_2O$, 1.0 mg $ZnSO_4.7H_2O$, 1.0 mg $MnCl_2.4H_2O$, 2 mg thiamine-HCl and 0.02 mg biotin in 1 L of water purified by reverse osmosis (pH 5.7)) with 1.5-3× $10^6$ spores and incubating at 30° C. with shaking at 200 rpm for 9-11 days. Cultures are harvested by filtration through one layer of Miracloth (Calbiochem, La Jolla, Calif.). Excess liquid is removed by hand squeezing. The average yield of packed cells per liter harvested is 22.5 g.

Example 3

SDS-PAGE Analysis

Samples from the column fractions are diluted in SDS-PAGE sample buffer (1× buffer=2% SDS w/v, 250 mM β-mercaptoethanol, 0.0025% bromphenol blue) and analyzed by electrophoresis. Polyacrylamide gradient gel electrophoresis (10-13%) is carried out according to the method of Laemmli ((1970) *Nature* 227:680-685) with some of the modifications of Delepelaire (1979) *Proc. Natl. Acad. Sci. USA* 76:111-115. Sodium dodecyl sulfate is used in the upper reservoir buffer at 0.1% but is omitted from the lower reservoir buffer, stacking and resolving gels. The stacking gel contains 5% of a 30% acrylamide stock (acrylamaid:N,N'-Methylenacrylamid, 37.5:1, Bio-Rad, Hercules, Calif.), 0.06% ammonium persulfate and 0.1% TEMED (v/v). The resolving gel contains a 10-13% linear gradient of acrylamide stock stabilized by a 0-10% linear gradient of sucrose. Electrophoresis is carried out at room temperature at 150V, constant voltage, for 7-9 hours. Proteins are visualized by staining with silver according to the method of Blum et al. (1987) *Electrophoresis* 8:93-99, or with Coomassie Blue (0.1% Coomassie Blue R-250, 50% methanol (v/v), 10% acetic acid (v/v)).

Example 4

Evaluation of the Chromatography Used by Kamisaka et al. (1997) in the Purification of DAGAT A. Preparation of the Lipid Body Fraction The following steps are performed at 4° C.

Typically, 70-75 g of wet packed *Mortierella ramanniana* cells (stored at −70° C.) are used for each lipid body preparation. Just prior to use, cells are thawed on ice and resuspended in 150 ml of Buffer A (10 mM potassium phosphate (pH 7.0), 0.15 M KCl, 0.5 M sucrose, and 1 mM EDTA). The following protease inhibitors are added to reduce proteolysis: 0.1 µM Aprotinin, 1 µM Leupeptin, and 100 µM Pefabloc (all from Boehringer Mannheim, Germany). Cells are divided into five, 50-ml tubes and lysed with a Polytron Tissue Homogenizer (Kinematic GmbH, Brinkman Instruments, Switzerland) on setting #7 with a 1 cm diameter probe for 7×1 min. The resulting slurry is transferred to centrifuge tubes (29×104 mm) and solid debris made to pellet by spinning at 1500×g (Beckman Instruments, J2-21, JA-20 rotor, 3500 rpm) for 10 min at 4° C. The supernatant is removed and the pellets washed with another 5 ml of Buffer A. Following centrifugation, the supernatant volumes are combined. This fraction is referred to as the 'S1'. The S1 is divided into six ultracentrifuge tubes (25×89 mm, Beckman Instruments, Fullerton, Calif.) and each is overlayed with 5 ml of Buffer B (10 mM potassium phosphate, pH 7.0, 0.15 M KCl, 0.3 M sucrose, and 1 mM EDTA). Samples are centrifuged at 100,000×g (Beckman Instruments, L8-M, SW-28 rotor, 21000 rpm) at 4° C. for 3 hours. The Lipid Body Fraction (LBF), floating on top of the overlay, is recovered with a spatula and transferred to a glass homogenizer (Potter-Elvehjem). Small amounts of LBF remaining in the centrifuge tube are recovered with a pipette by removing 4 ml of the Buffer B overlay and combining it with the LBF in the homogenizer. The final LBF is homogenized in 40 ml of Buffer B. The remaining fractions are collected as follows: Interface fraction (the interface between the 0.3 and 0.5 M sucrose buffers), Soluble fraction (the liquid volume beneath the interface), and the Membrane fraction (a tan/brown pellet at the bottom of each tube). All are frozen and stored at −70° C. for solubilization and further purification.

B. Solubilization of DAGAT Activity

The LBF is thawed on ice and solubilization is achieved by addition of Triton X-100 (Boehringer Mannheim, Mannheim, Germany) from a 10% (w/v) stock to a final concentration of 1.3% (w/v). Solid sucrose (Mallinckrodt, Paris, Ky.) is added to achieve a final concentration of 0.5M. The detergent-treated sample is rocked at 4° C. for one hour then divided into six ultracentrifuge tubes (25×89 mm, Beckman Instruments). Each tube is overlayed with 5 ml of Buffer B. Samples are centrifuged at 100,000×g (Beckman Instruments, L8-M, SW-28 rotor, 21000 rpm) at 4° C. for 3 hours. The solubilized material, referred to as the 'Triton X-100 extract', is recovered by inserting a thin tube through the overlay to within 1 cm of the bottom of each ultracentrifuge tube and removing the lower, 0.5M sucrose, layer with gentle suction while leaving the upper 0.3M sucrose overlay (including a floating fat layer) and the pellet behind.

In the protocol described by Kamisaka et al. (1997) supra, the Lipid Body Fraction was solubilized with 0.1% (w/v) Triton X-100 and further centrifuged at 100,000×g or filtered through a 0.2 µm filter. As described in Kamisaka et al. (1997) supra it was necessary to increase the Triton X-100 concentration to 1.5% for DAGAT activity to bind the first column.

C. Chromatography used in the Purification of DAGAT

Buffer C, used for chromatography, contains 10 mM potassium phosphate (pH 7.0), 0.1% Triton X-100 (w/v) (Boehringer Mannheim, Mannheim, Germany), 10% glycerol (w/v), 0.1 µM Aprotinin, 1 µM Leupeptin, 100 µM Pefabloc (all from Boehringer Mannheim, Mannheim, Germany) and varying amounts of potassium chloride (75-500 mM). This buffer differs from the corresponding column buffer used by Kamisaka et al. (1997) supra, in that glycerol is substituted for ethylene glycol and EDTA, DTT, and PMSF are omitted while Aprotinin, Leupeptin and Pefabloc are included. Following the protocol by Kamisaka et al. (1997) supra, a Yellow 86-Agarose (Sigma R-8504, St. Louis, Mo.) column is prepared (1.5 cm×5.8 cm) and equilibrated with 150 mM KCl in Buffer C. The majority of the DAGAT activity present in the Triton X-100 extract did not bind the Yellow 86-Agarose column. However, a significant portion of the DAGAT activity was bound to the column by diluting the KCl concentration of the applied sample to 75 mM with an equal volume of Buffer C (without KCl). In accordance, the Yellow 86-Agarose column is also equilibrated in 75 mM KCl in Buffer C. Following application of the sample at 0.56 ml/min, the column is washed with 4 column volumes of equilibration buffer. DAGAT activity and proteins bound to the column are eluted with 500 mM KCl in Buffer C (FIG. 1).

Figure 2A:
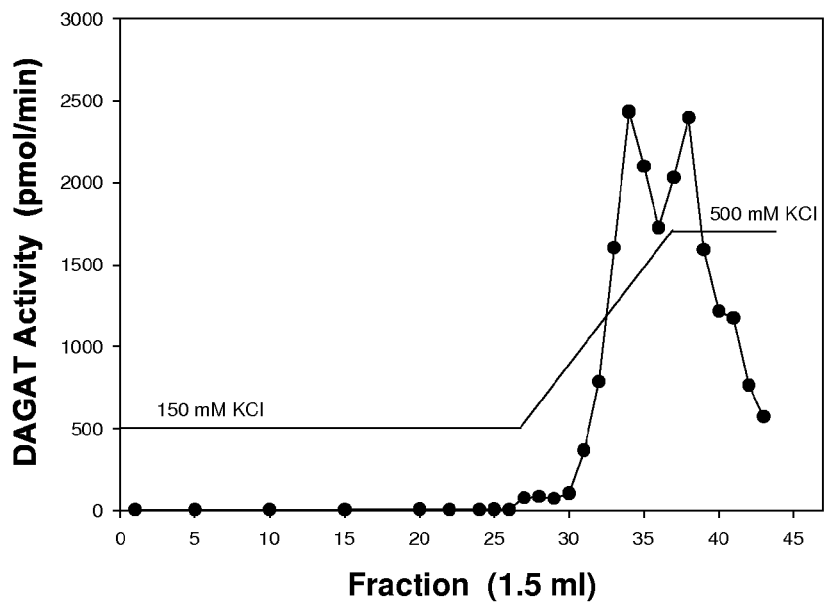
FIG. 2A shows the results of chromatography of *Mortierella ramanniana* DAGAT activity from the Yellow 86-Agarose column on a column of Heparin Sepharose CL6B.

DAGAT activity eluted from the Yellow 86-Agarose column (fractions 17-20) is diluted 1:3.33 with Buffer C to reduce the KCl concentration to 150 mM. The diluted pool (103 ml) is applied to a Heparin-Sepharose CL-6B column (Pharmacia, Uppsala, Sweden, 0.5 cm×4.8 cm) equilibrated with 150 mM KCl in Buffer C at 0.2 ml/min. The column is washed with 5 volumes of equilibration buffer and DAGAT activity and protein are eluted in a 15 ml linear gradient of 150-500 mM KCl in Buffer C. DAGAT activity elutes in two overlapping peaks. The first peak elutes during the gradient, as found by Kamisaka et al. (1997) supra, and a second peak, not found by Kamisaka et al., elutes at the end of the gradient with much less protein (FIG. 2A).

A portion (250 µl) of the two peak fractions from the Heparin column are further purified by size exclusion chromatography on a Superdex-200 column (1×30 cm, Bio-Rad, Hercules, Calif.) at 0.2 ml/min equilibrated with 150 mM KCl in Buffer C. For calibration only, the column is equilibrated with 150 mM KCl in a Modified Buffer C in which Triton X-100 is replaced with Triton X-100 R (Calbiochem, La Jolla, Calif.). The column is calibrated using Bio-Rad Gel Filtration Standards. The DAGAT activity from each of the two peaks from Heparin Sepharose CL-6B elutes at an estimated molecular mass of 99 kDa.

Figure 3A:
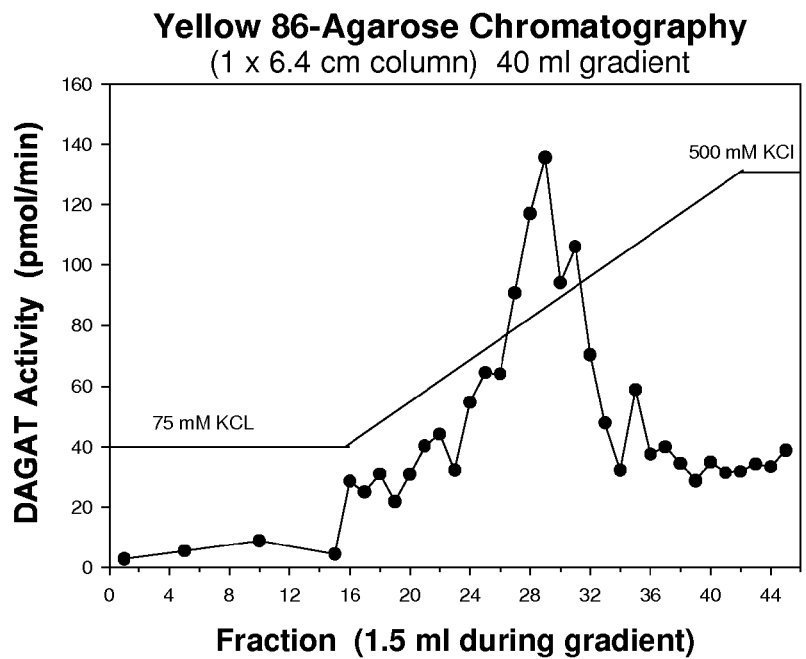
FIG. 3A shows the results of chromatography of *Mortierella ramanniana* DAGAT activity from the second activity peak of the Heparin Sepharose CL6B column chromatographed on a Yellow 86-Agarose column where protein was eluted during a gradient of 75-150 mM KCl.

Additional chromatography is performed on the later eluting peak from the Heparin column, which contained DAGAT at a higher specific activity. In this case, the second peak from the Heparin column (fractions 36-41) is diluted 1:6.6 with Buffer C to a volume of 46.7 ml. The sample is applied to a Yellow 86 Agarose column (1.0 cm×6.4 cm) equilibrated with 75 mM KCl in Buffer C at 0.5 ml/min. After washing with 5 column volumes of equilibration buffer, bound proteins and all of the DAGAT activity elute in a 40 ml linear gradient of 75-500 mM KCl in Buffer C. DAGAT activity elutes as a single peak (FIG. 3A).

Figure 2B:
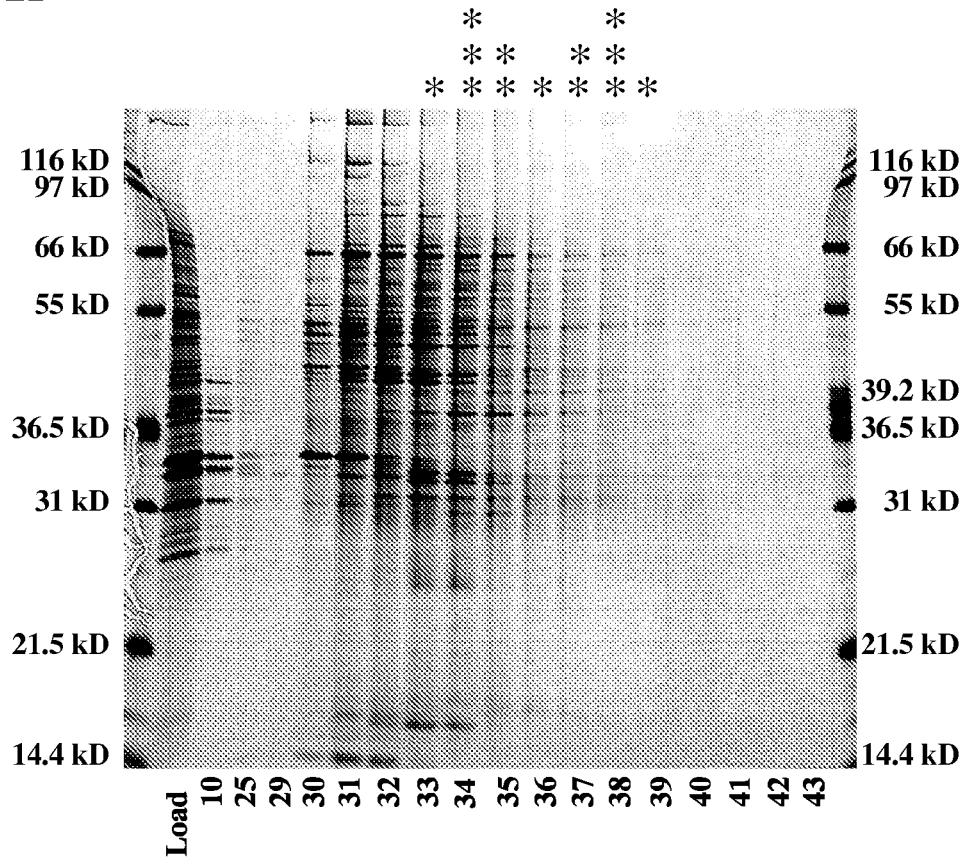
FIG. 2B shows SDS-PAGE analyses of fractions from the Heparin Sepharose CL6B column. Protein bands are detected by silver stain.
Figure 3B:
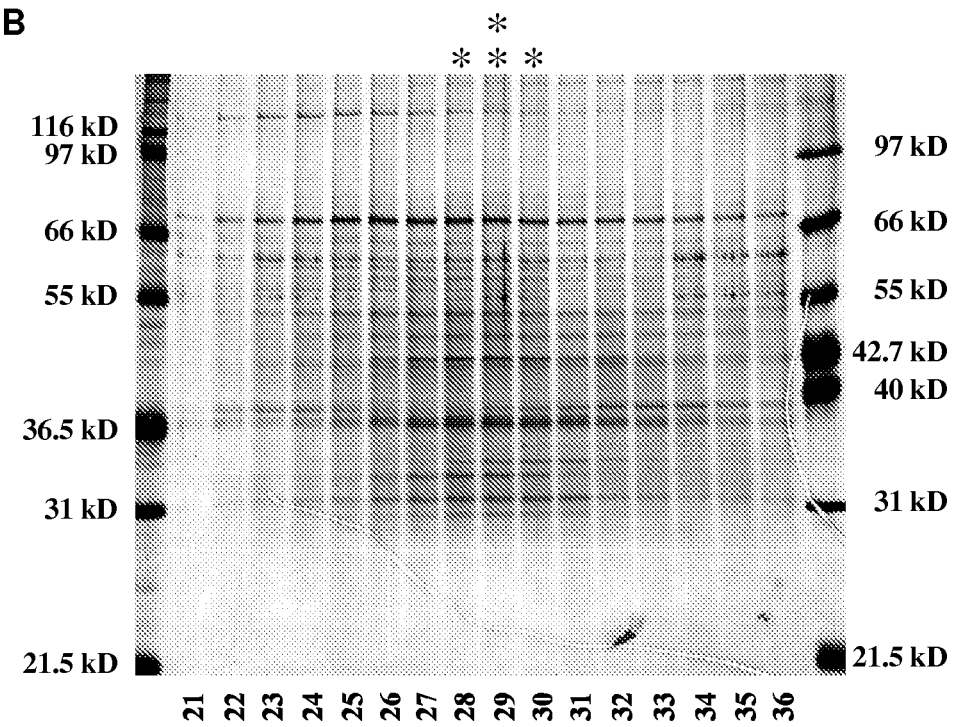
FIG. 3B shows SDS-PAGE analyses of fractions from the Yellow 86-Agarose column. Protein bands are detected by silver stain.

The protein composition of the fractions containing DAGAT activity from the Heparin and second Yellow 86 columns are analyzed by gradient SDS-PAGE according to the protocol in Example 3. Protein bands are detected by silver-staining. The pattern of bands eluting from these columns is compared, fraction by fraction, to the respective DAGAT activity profile. Many protein candidates are present that correlate with the presence of DAGAT activity. This purification protocol is insufficient to identify a particular protein candidate associated with DAGAT activity (FIG. 2B, 3B).

Example 5

New Purification Protocol for Identifying DAGAT Protein Candidates

A. Preparation of the Lipid Body Fraction

The following steps are performed at 4° C.

Typically, 70-75 g of wet packed *Mortierella ramanniana* cells (stored at −70° C.) are used for each lipid body preparation. Just prior to use, cells are thawed on ice and resuspended in 150 ml of Buffer A (10 µM potassium phosphate (pH 7.0), 0.15 M KCl, 0.5 M sucrose, 1 mM EDTA). The following protease inhibitors are added to reduce proteolysis: 0.1 M Aprotinin, 1 µM Leupeptin, and 100 µM Pefabloc (all from Boehringer Mannheim, Germany). Samples are lysed with a cell disrupter (Bead-Beater, Biospec Products, Bartlesville, Okla.) using 0.5 nm glass beads. The sample chamber is filled with 180 ml of glass beads. Wet-packed cells are thawed on ice and resuspended in 150 ml of Buffer A. The cell slurry is poured over the glass beads. In general, an additional 40-50 ml of Buffer A are needed to fill the chamber for proper functioning. This volume is used to rinse the remains of the cell slurry from its original container so that it can be combined with the rest of the sample. Cells are ground ('Homogenize' setting) for 45-90 seconds depending on the viscosity of the sample. The cell slurry containing glass beads is divided into tubes (29×104 mm) and centrifuged at 500×g (Beckman Instruments, GP centrifuge, GH 3.7 Horizontal rotor at 1500 rpm) and 4° C. The supernatant is removed and the pellets washed with another 5 ml of Buffer A. Following centrifugation the supernatant volumes are combined. This fraction is referred to as the 'S1'. The S1 is divided into six ultracentrifuge tubes (25×89 mm, Beckman Instruments) and each is overlayed with 5 ml of Modified Buffer B (10 mM potassium phosphate, pH 7.0, 0.15 M KCl, and 0.3 M sucrose). EDTA is omitted from Buffer B (see Example 4) since it interferes with hydroxylapatite chromatography. Samples are centrifuged at 100,000×g (Beckman Instruments, L8-M, SW-28 rotor, 21000 rpm) at 4° C. for 3 hours. The Lipid Body Fraction (LBF), floating on top of the overlay, is recovered with a spatula and transferred to a glass homogenizer. Small amounts of LBF remaining in the centrifuge tube are recovered with a pipette by removing 4 ml of the Buffer B overlay and combining it with the LBF in the homogenizer. The final LBF is homogenized in 40 ml of Buffer B. The remaining fractions are collected as follows: Interface fraction (the interface between the 0.3 and 0.5 M sucrose buffers), Soluble fraction (the liquid volume beneath the interface), and the Membrane fraction (a tan/brown pellet at the bottom of each tube). All are frozen and stored at −70° C. for solubilization and further purification.

B. Solubilization of DAGAT Activity from the Lipid Body Fraction

Prior to solubilization, a protein determination is made with an aliquot of the Lipid Body Fraction by the method of Bradford (Bio-Rad Reagent, Hercules, Calif.) using bovine serum albumin as a standard. The LBF is thawed on ice, then diluted to a concentration of 1 mg protein/ml and treated with Triton X-100 at a detergent to protein ratio of 15:1 (w/w, equivalent to 1.3% Triton X-100). Solid sucrose (Mallinckrodt, Paris, Ky.) is added to achieve a final concentration of 0.5M. The detergent-treated sample is rocked at 4° C. for one hour then divided into six ultracentrifuge tubes (25×89 mm, Beckman Instruments). Each tube is overlayed with 5 ml of Modified Buffer B. Samples are centrifuged at 100,000×g (Beckman Instruments, L-8M, SW-28 rotor, 21000 rpm) at 4° C. for 3 hours. The solubilized material, referred to as the 'Triton X-100 extract', is recovered by inserting a thin tube through the overlay to within 1 cm of the bottom of each ultracentrifuge tube and removing the lower, 0.5M sucrose, layer with gentle suction while leaving the upper 0.3M sucrose overlay (including a floating fat layer) and the pellet behind.

C. DAGAT Column Chromotography

A purification method of Yellow 86-Agarose followed by hydroxylapatite chromatography is used to further purify the protein. The method is performed in two ways. In Protocol A, activity is bound to the first column and after elution, fractions are assayed for activity. The active fractions are then pooled and applied to the second column (also referred to as a sequential run). In Protocol B, activity is bound to the first column then elutes and flows directly onto the second column without pooling and assaying in between (also referred to as a tandem run).

Figure 4:
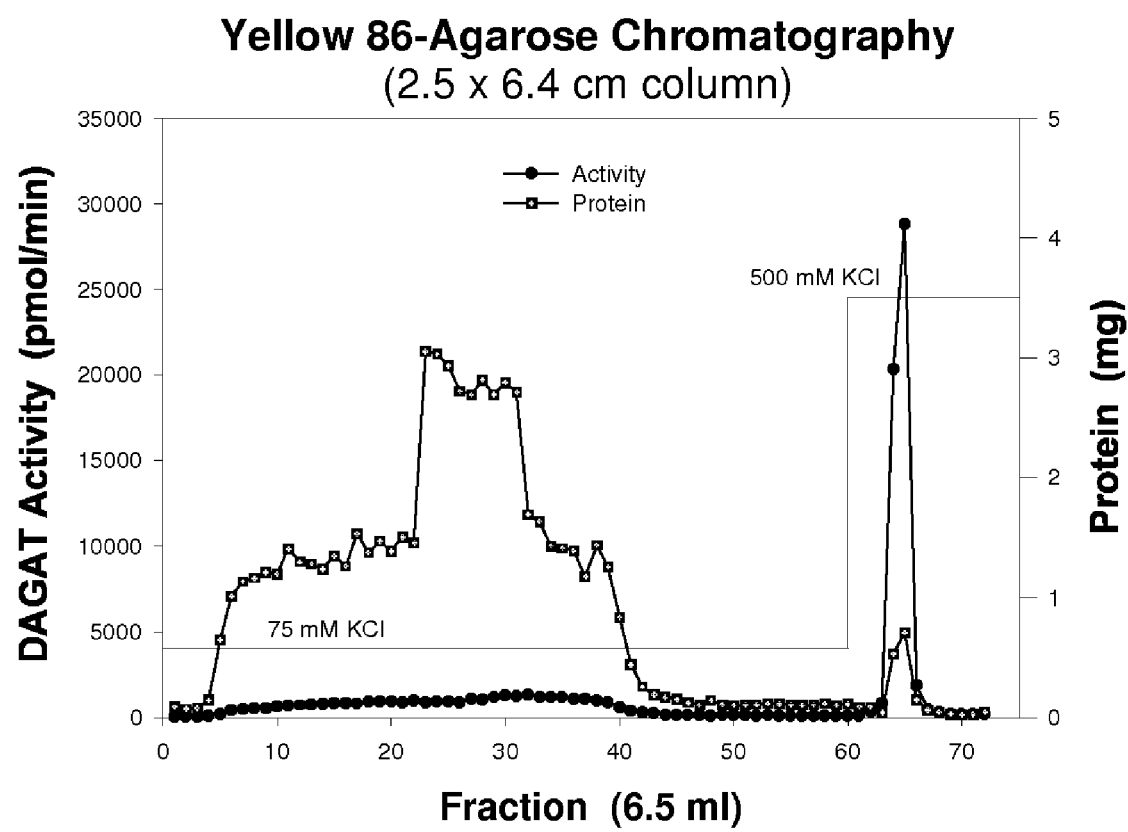
FIG. 4 shows the results of chromatography of *Mortierella ramanniana* DAGAT activity on a Yellow 86-Agarose column.
Figure 5A:
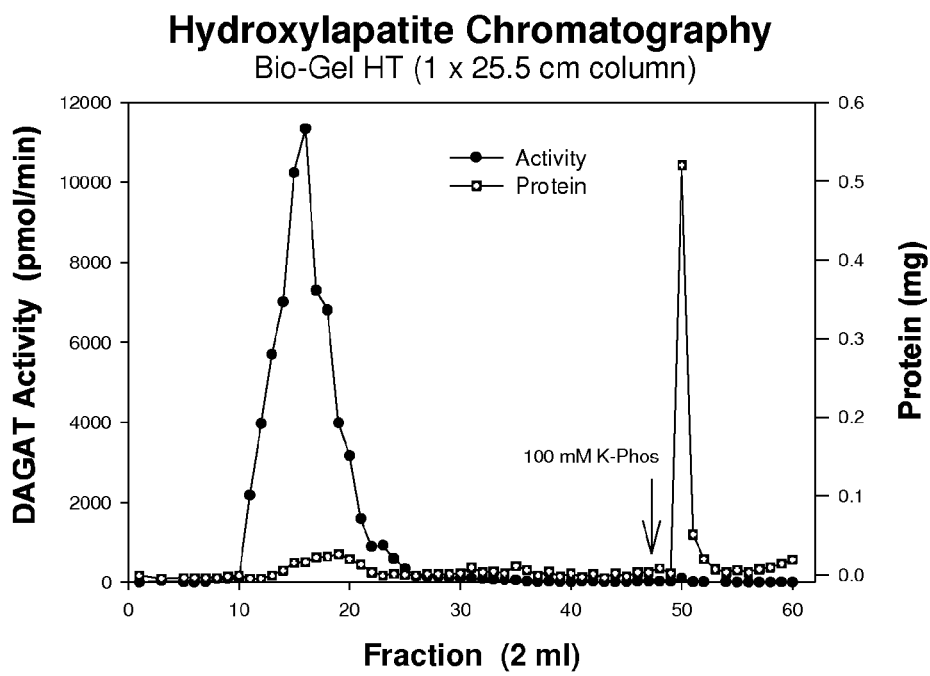
FIG. 5A shows the results of chromatography of *Mortierella ramanniana* DAGAT activity from the Yellow 86-Agarose column on a column of hydroxylapatite (Bio-Gel HT).
Figure 5B:
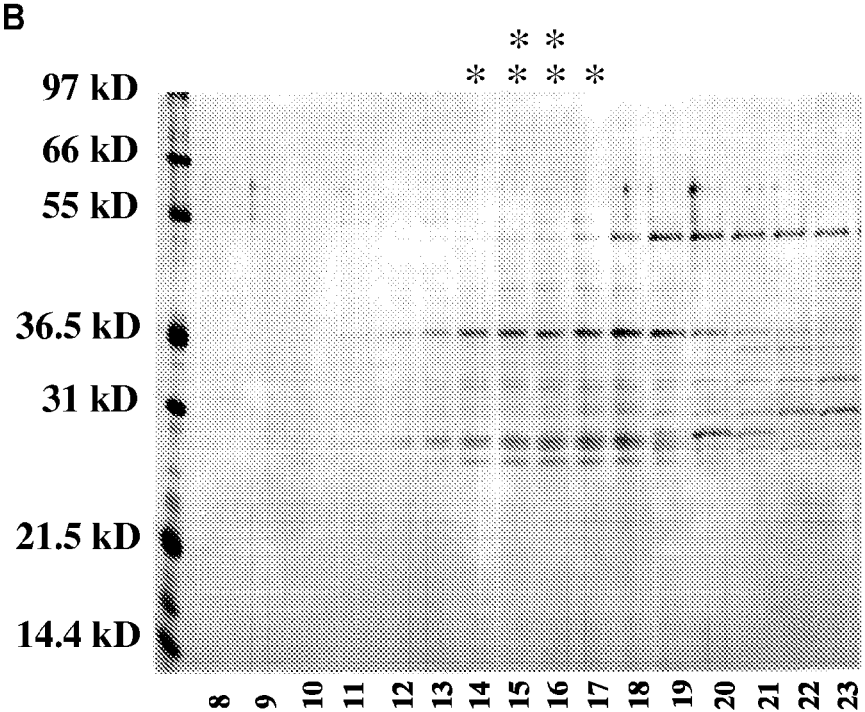
FIG. 5B shows SDS-PAGE analyses of fractions from the hydroxylapatite column. Protein bands are detected by silver stain.

In Protocol A, the Triton X-100 extract is applied to a Yellow 86-Agarose column (2.5 cm×6.4 cm) equilibrated with 75 mM KCl in Buffer C (Example 4.C) at 2 ml/min. The column is washed with 5 column volumes of equilibration buffer then eluted with 500 mM KCl in Buffer C at 0.5 ml/min (FIG. 4). The two most active fractions (64 and 65), containing 93% of the eluted activity, are pooled and loaded onto a hydroxylapatite column (Bio-Gel HT, Bio-Rad, 1 cm×25.5 cm) equilibrated with 500 mM KCl in Buffer C at 0.5 ml/min. DAGAT activity flows through the column whereas the majority of the proteins bind the column. The column is washed with 3 volumes of equilibration buffer. Bound proteins are eluted with 100 mM dipotassium phosphate and 500 mM KCl in Buffer C at 0.5 ml/min (FIG. 5A). A portion of the fractions containing the DAGAT activity peak are run on gradient gel SDS-PAGE as described in Example 9. The proteins are stained with silver and the pattern of the bands are compared, fraction by fraction, to the activity profile (FIG. 5B). Several DAGAT protein candidates correlate with activity. In particular, attention is called to bands migrating at positions corresponding approximately to 43 kD, 36.5 kD, 33 kDa, 29 kD, 28 kD and 27 kD. There does not appear to be a candidate protein in the region of 53 kD that correlates with activity.

In Protocol B, the Triton X-100 extract is applied to a Yellow 86-Agarose column (1.5 cm×5.8 cm) equilibrated with 75 mM KCl in Buffer C at 1 ml/min. The column is washed with 5 column volumes of equilibration buffer. Then, the outlet from the Yellow 86-Agarose column is connected to the inlet of a hydroxylapatite column (1.0 cm×26.2 cm, Bio-Gel HT, Bio-Rad, Hercules, Calif.) equilibrated with 500 mM KCl in Buffer C. DAGAT activity bound to the Yellow 86 column is eluted with 110 ml of Buffer C containing, 500 mM KCl and passes directly through the hydroxylapatite column at 0.2 ml/min. Finally, the hydroxylapatite column is disconnected from the Yellow 86-Agarose column and proteins bound to the hydroxylapatite column are eluted with 100 mM dipotassium phosphate and 500 mM KCl in Buffer C. DAGAT activity is found in fractions from the hydroxylapatite column collected during the 110-ml wash with Buffer C containing 500 mM KCl.

Figure 6A:
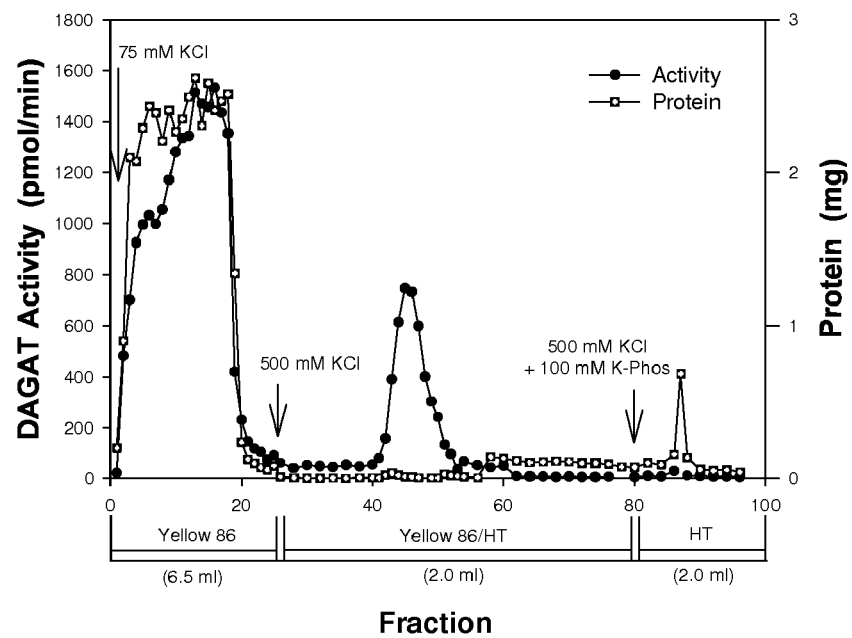
FIG. 6A provides results of tandem Yellow 86-Agarose/Hydroxylapatite chromatography.

The majority of the protein in the Triton X-100 extract does not bind the Yellow 86-Agarose column and is discarded. A small subset of proteins, including DAGAT, do bind the Yellow 86-Agarose column and are eluted with 500 mM KCl in Buffer C. When this eluate is applied to the hydroxylapatite column, DAGAT activity flows through while most of the remaining proteins bind the column and are separated (FIG. 6A). A portion of the fractions containing the DAGAT activity peak are run on gradient gel SDS-PAGE and are silver-stained. The pattern of bands eluting from these columns is compared, fraction by fraction, to the respective DAGAT activity profile. Examination of the stained protein bands indicate a protein at approximately 33 kDa correlates best with DAGAT activity (FIG. 6B).

Figure 6B:
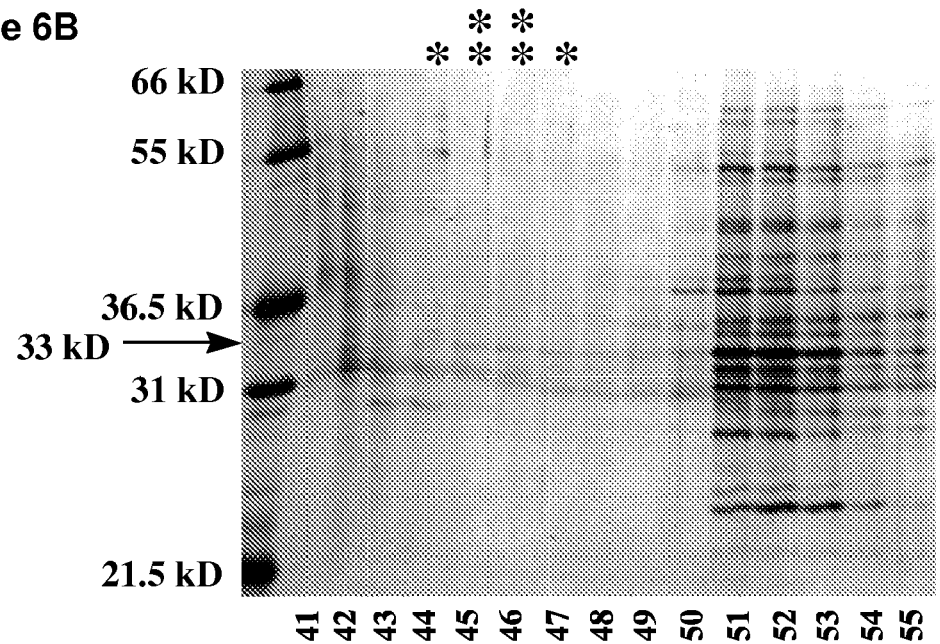
FIG. 6B provides results of SDS-PAGE analysis of the peak fractions from the tandem chromotography. Protein bands are detected by silver stain.

Protein sequence from the 36.5 kDa candidate seen in FIG. 5B and from the 33 kDa candidate seen in FIG. 6B are obtained as described in Examples 8 and 9 and the peptides are used to search the databases. Peptides generated from the 36.5 kDa candidate matched glyceraldehyde-3-phosphate (GAP) dehydrogenase. The best match to the peptides from the 33 kDa candidate is RNA helicase.

Example 6

Modified Protocol for Identifying DAGAT

A. Preparation of the Lipid Body Fraction

The following steps are performed at 4° C.

Typically, 70-75 g of wet *Mortierella ramanniana* packed cells (stored at −70° C.) are used for each lipid body preparation. Just prior to use, cells are thawed on ice and resuspended in 150 ml of Buffer A (10 mM potassium phosphate (pH 7.0), 1 M KCl, 0.5 M sucrose, 1 mM EDTA). The KCl concentration is increased from 0.15 M to 1 M in order to reduce the non-specific binding of soluble proteins with the Lipid Body Fraction. The following protease inhibitors are added to reduce proteolysis: 0.1 µM Aprotinin, 1 µM Leupeptin, and 1100 µM Pefabloc (all from Boehringer Mannheim, Germany). Samples are lysed with a cell disrupter (Bead-Beater, Biospec Products, Bartlesville, Okla.) using 0.5 mm glass beads. The sample chamber is filled with 180 ml of glass beads. Wet-packed cells are thawed on ice and resuspended in 150 ml of Buffer A. The cell slurry is poured over the glass beads. In general, an additional 40-50 ml of Buffer A are needed to fill the chamber for proper functioning. This volume is used to rinse the remains of the cell slurry from its original container so that it can be combined with the rest of the sample. The chamber is surrounded by ice in order to keep the sample cool during lysis. Cells are ground ('Homogenize' setting) for 15 seconds then cooled for 1 minute and the process repeated 2 times. The cell slurry containing glass beads is divided into tubes (29×104 mm) and centrifuged at 1500×g (Beckman Instruments, GP centrifuge, GH 3.7 Horizontal rotor at 2460 rpm) for 10 minutes at 4° C. The supernatant is removed and the pellets washed with another 5 ml of Buffer A. Following centrifugation the supernatant volumes are combined. This fraction is referred to as the 'S1'. The S1 is divided into six ultracentrifuge tubes (25×89 mm, Beckman Instruments) and each is overlayed with 5 ml of Modified Buffer B (10 mM potassium phosphate, pH 7.0, 1 M KCl, and 0.3 M sucrose). EDTA is omitted from Buffer B (see Example 4) since it interferes with hydroxylapatite chromatography. Samples are centrifuged at 100,000×g (Beckman Instruments, L8-M, SW-28 rotor, 21000 rpm) at 4° C. for 3 hours. The Lipid Body Fraction (LBF), floating on top of the overlays, are recovered with a spatula and transferred to a glass homogenizer for solubilization. The remaining fractions are collected as follows: the Soluble fraction (the liquid volume beneath the Lipid Body Fraction) and the Membrane fraction (a tan/brown pellet at the bottom of each tube) is pooled from each tube and saved for assay. The membrane fraction is resuspended in 3.84 ml of Modified Buffer A (in which the KCl concentration has been reduced to 75 mM KCl).

B. Solubilization of DAGAT Activity from the Lipid Body Fraction

On the same day the final LBF is homogenized in 50 ml of Solubilization Buffer (10 mM potassium phosphate (pH 7.0), 75 mM KCl, 0.5M Sucrose, 1.5% Triton X-100) and the homogenate is centrifuged at 90,000×g for 1.8 hours SW-28 at 27 k rpm). Following centrifugation the floating lipid layer is discarded and the solubilized layer (Triton X-100 extract) is pooled and stored at −70° C. awaiting further purification. The Triton X-100 extract is ready to load onto the first column without further dilution.

C. DAGAT Column Chromotography Using Yellow 86-Agarose and HA in Tandem Mode (Protocol B)

Figure 7A:
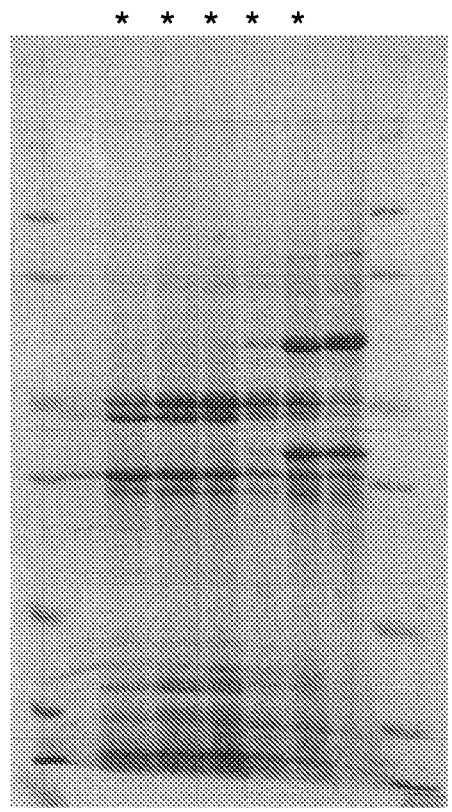
FIGS. 7A and 7B shows SDS-PAGE analyses of high salt and low salt preparation of lipid body fraction purified through Yellow 86-Agarose/Hydroxylapatite chromatography. Protein bands are detected by Coomassie Blue stain.

For comparison with the protocol described in Example 5, one Lipid Body Fraction is prepared as described in Example 5B (low salt) and another Lipid Body Fraction is prepared as described in Example 6B (high salt). Each preparation is solubilized with Triton X-100. The Triton X-100 extracts are chromatographed through Yellow 86-Agarose and hydroxylapatite as described in Example 5C, Protocol B. The amount of protein recovered in the high salt preparation is greater than that recovered in the low salt preparation as shown in FIG. 7A (high salt) and 7B (low salt).

All subsequent preparations are made using the high salt protocol described in Example 6A/B.

Figure 7B:
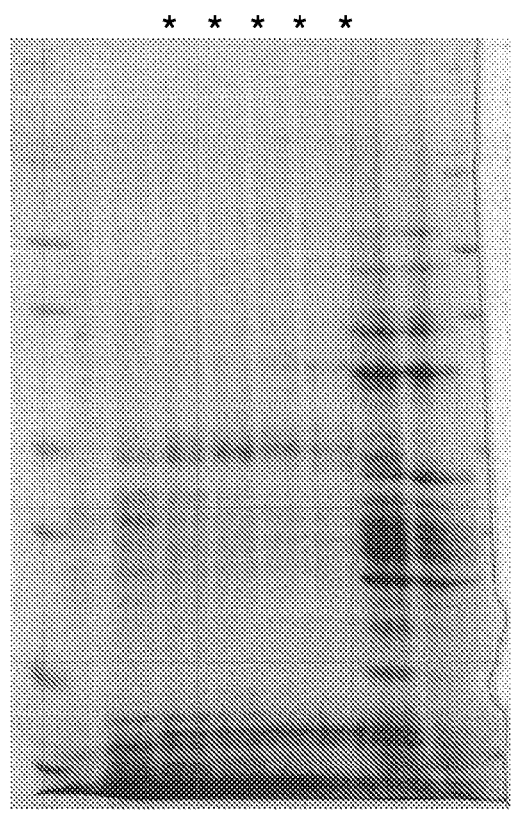

These two comparative preparations also reveal additional DAGAT protein candidates after SDS-PAGE analysis that are not seen previously, especially using the high salt protocol. Active fractions from the two purifications are prepared for in-gel digestion by precipitating fractions from the HA column as described in Example 8B and separated by gradient gel SDS-PAGE as described in Example 8C. Coomassie stained proteins of approximate sizes 55, 50, 39, 36.5, 36, 33, 32.5, 32, 29, and 27 kDa are excised from the gel made from the high salt preparation (FIG. 7A). Coomassie stained proteins of approximate sizes 39, 36.5, 36, 35, 32, 31, 29, and 27 kDa are excised from the gel made from the low salt preparation (FIG. 7B). These candidates are stored at −70° C. for later use in protein sequencing. The 36 kDa band from the high salt preparation was designated Mr18. The 36 kDa band from the low salt preparation was designated Mr19.

Figure 8A:
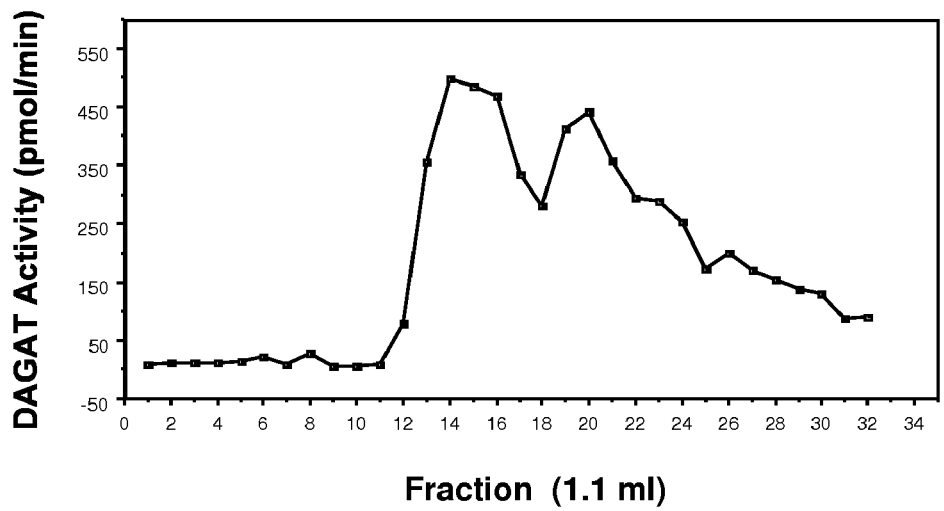
FIG. 8A shows the results of chromatography of *Mortierella ramanniana* DAGAT activity from the Heparin column following chromatography on Yellow 86-Agarose and hydroxylapatite (Bio-Gel HT).
Figure 8B:
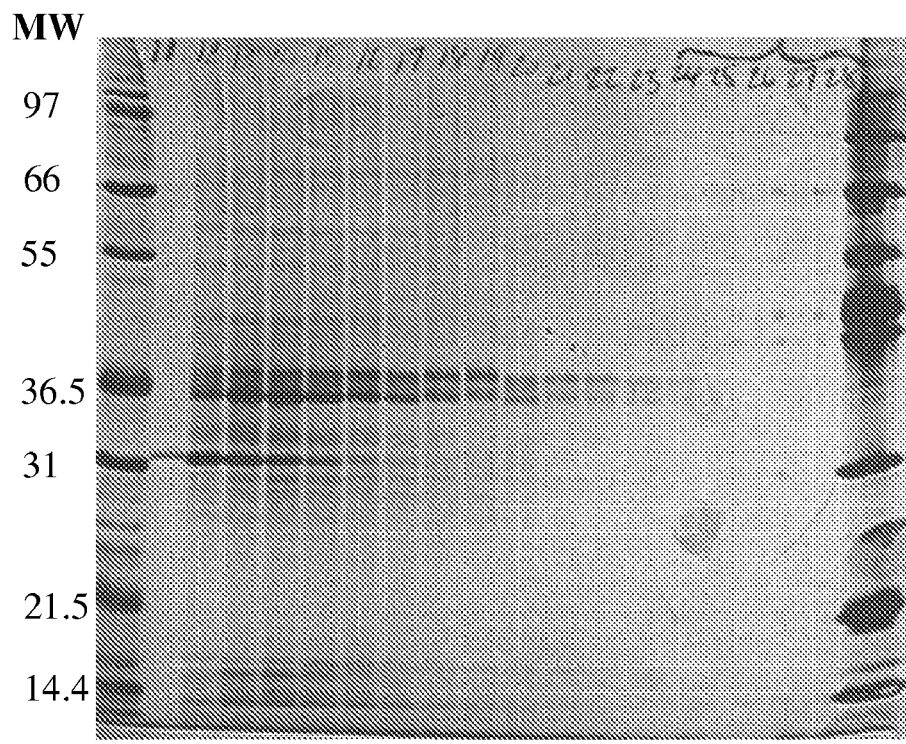
FIG. 8B shows SDS-PAGE analyses of fractions from the Heparin column. Protein bands are detected by silver stain.

D. DAGAT Column Chromatography Using Yellow 86-Agarose, Hydroxylapatite and Heparin The Triton X-100 extract described in Example 6B is thawed and applied to a Yellow 86-Agarose column (2.5 cm×6.4 cm) equilibrated with 75 mM KCl in Buffer C (10 mM potassium phosphate (pH 7.0), 0.1% (w/v) Tx-100, 10% (w/v) glycerol) at 2 ml/min. Most of the protein does not bind the column but a portion of the protein and DAGAT activity bind the column. The column is washed with 5 column volumes of equilibration buffer then bound protein and DAGAT activity are eluted over a 120 ml linear gradient of 75-500 mM KCl in Buffer C at 2 ml/min. Fractions are assayed immediately and active fractions are pooled and concentrated 8 fold by ultrafiltration using a pressurized stirred cell (Amicon) fitted with a YM-30 membrane. The concentrate is loaded onto a hydroxylapatite column (approximately 1.0 cm×26 cm, Bio-Gel HT, Bio-Rad, Hercules, Calif.) equilibrated with 500 mM KCl in Buffer C at 0.5 ml/min and the column is washed with 40 ml of equilibration buffer. Since DAGAT activity is found in the flow-through and wash, bound proteins are not eluted in this experiment. Active fractions are pooled and diluted 1:3.3 to reduce the KCl concentration from 500 to 150 mM. The diluted sample is applied to a Heparin column (0.55×4.7 cm) equilibrated with 150 mM KCl in Buffer C at 0.5 ml/min. The column is washed with 5 volumes of equilibration buffer and bound protein is eluted in a 10 ml linear gradient of 150-500 mM KCl in Buffer C at 0.25 ml/min. After the gradient the column is washed with 15 volumes of 500 mM KCl in Buffer C at 0.25 ml/min. DAGAT activity elutes in two peaks, one during the gradient and one during the 500 mM KCl wash after the gradient. Fractions over the column profile, including those containing DAGAT activity, are concentrated by precipitation as in Example 8. The precipitated samples are separated by gradient gel SDS-PAGE and the gel is stained with silver as in Example 3. The pattern of bands eluting from the column are compared, fraction by fraction, to the respective DAGAT activity profile (FIG. 8A). Examination of the stained protein bands indicate a protein in the size range of about 36 kDa to about 37 kDa correlates best with DAGAT activity found in the peak eluting during the 500 mM KCl wash (FIG. 8B). Based on this information, the 36 to about 37 kDa protein bands excised from the two gels described in Example 6C are sent for in-gel digestion and protein sequencing.

Example 7

Scale-Up of the Purification Protocol for Identifying DAGAT Protein Candidates from *Mortierella ramanniana*

The purification protocol described in Example 6D indicates two possible forms of DAGAT may be present in this preparation, however, there is insufficient protein at the final step of purification to proceed with protein sequencing therefore a scale-up of the protocol was performed.

A. Scale-Up Through Yellow 86-Agarose

Figure 9:
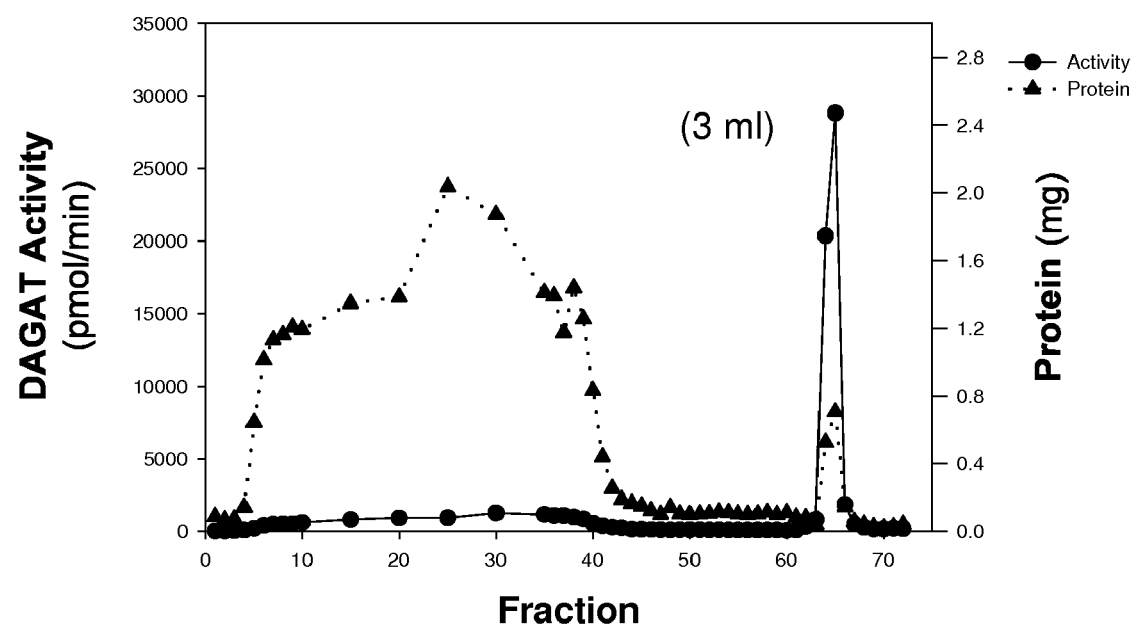
FIG. 9 shows the results of chromatography of *Mortierella ramanniana* DAGAT activity on a Yellow 86-Agarose column.

The Triton X-100 extract described in Example 6A and 6B is thawed and applied to a Yellow 86-Agarose column (2.5 cm×6.4 cm) equilibrated with 75 mM KCl in Buffer C (10 mM potassium phosphate (pH 7.0), 0.1% (w/v) Tx-100, 10% (w/v) glycerol) at 2 ml/min. Most of the protein does not bind the column but a portion of the protein and DAGAT activity bind the column. The column is washed with 5 column volumes of equilibration buffer then bound protein and DAGAT activity are eluted with 500 mM KCl in Buffer C at 2 ml/min (FIG. 9). The DAGAT activity is stable to freeze/thaw at this stage of purification so eluted fractions are typically stored at −70° C. at this stage. Eluted fractions are also assayed for DAGAT activity according to Example 1B.

B. Chromatography on Hydroxylapatite

Figure 10A:
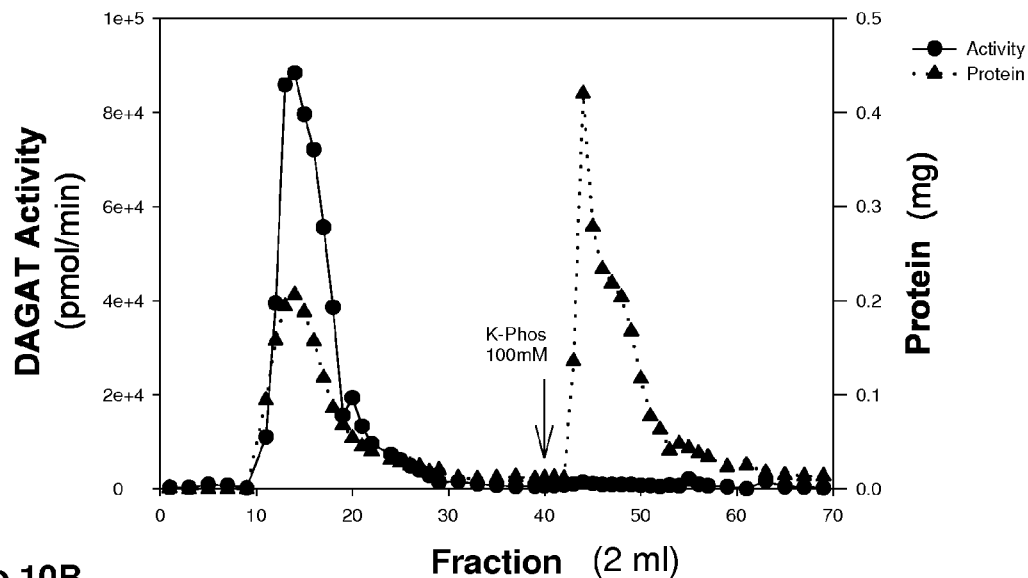
FIG. 10A shows the results of chromatography of *Mortierella ramanniana* DAGAT activity pooled from four Yellow 86-Agarose columns on a column of hydroxylapatite (Bio-Gel HT).
Figure 10B:
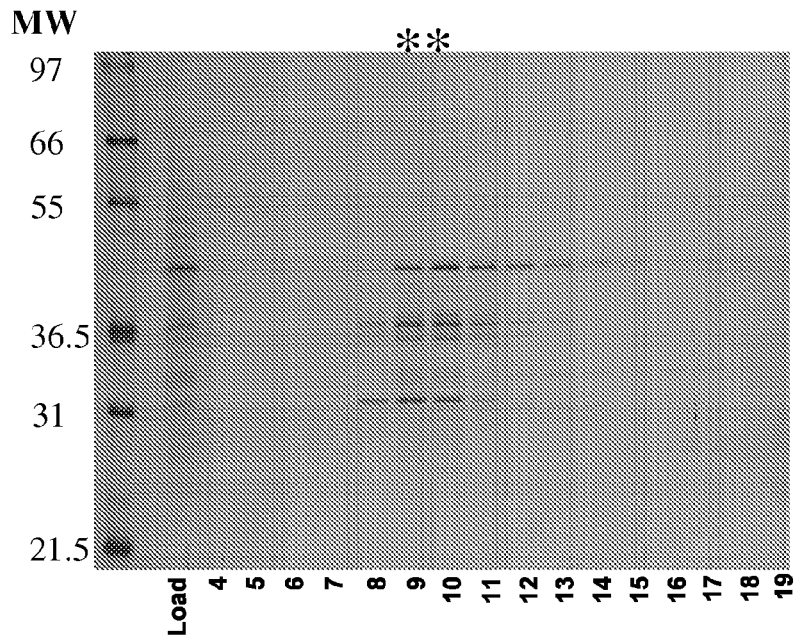
FIG. 10B shows SDS-PAGE analyses of fractions from the hydroxylapatite column. Protein bands are detected by silver stain.

After four preparations are purified through Yellow 86-Agarose, the most active fractions are pooled, concentrated 12-14 fold by ultrafiltration (Amicon stirred cell, YM-30 membrane) and applied (0.5 ml/min) to a hydroxylapatite column (Bio-Gel HT, Bio-Rad, 1 cm×25.5 cm) equilibrated with 500 mM KCl in Buffer C. Concentration of the sample is performed prior to HA chromatography in order to reduce the time required for loading of the sample. DAGAT activity flows through the column whereas the majority of the remaining proteins bind the column and are separated. The column is washed with 3 volumes of equilibration buffer. Bound proteins are eluted with 100 mM dipotassium phosphate and 500 mM KCl in Buffer C at 0.5 ml/min (FIG. 10A). A portion of the fractions containing the DAGAT activity peak are run on gradient gel SDS-PAGE as described in Example 3. The proteins are stained with silver and the pattern of the bands are compared, fraction by fraction, to the activity profile (FIG. 10B). Several DAGAT protein candidates correlate with activity. In particular, attention is called to bands migrating at positions corresponding approximately to 36.5 kD, 36 kD, 35 kDa, 34 kD, 33 kD and 31 kD. Again, there does not appear to be a candidate protein in the region of 53 kD previously described that correlates with activity.

C. Chromatography on Heparin

Figure 11A:
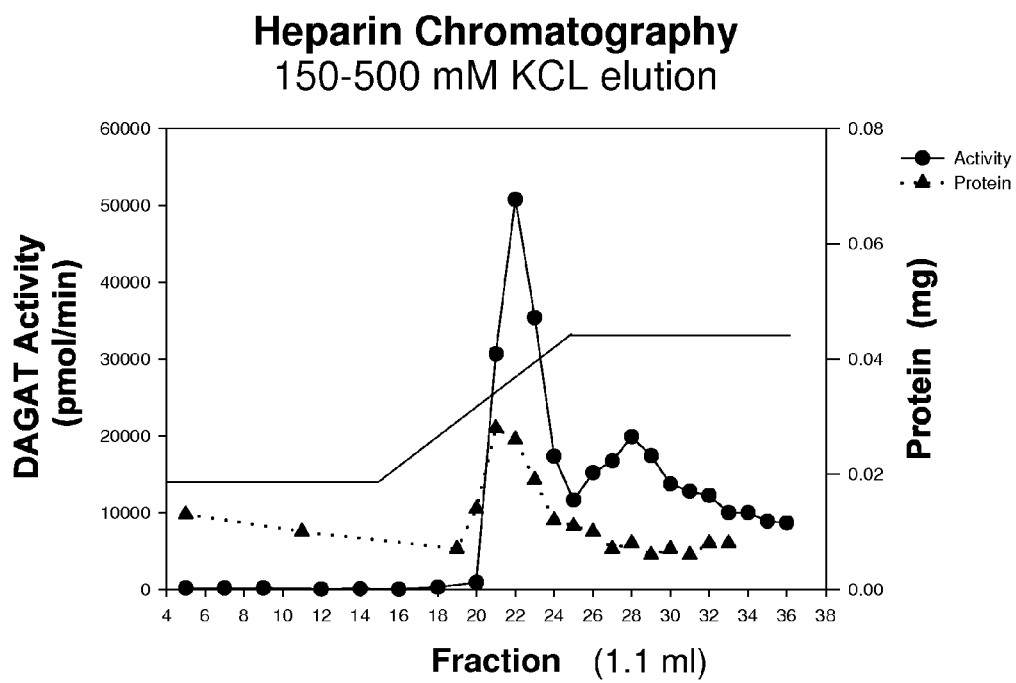
FIG. 11A shows the results of chromatography of *Mortierella ramanniana* DAGAT activity from the hydroxylapatite column on a column of Heparin Sepharose CL6B.
Figure 11B:
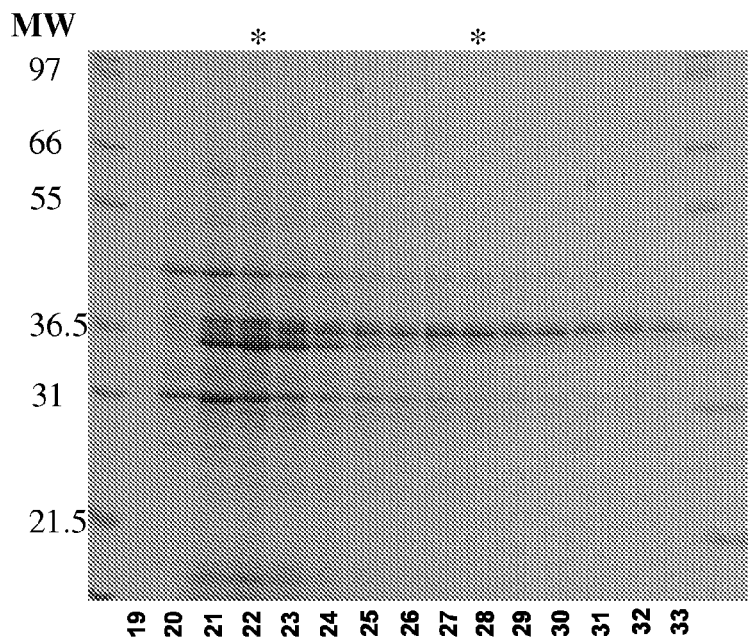
FIG. 11B shows SDS-PAGE analyses of fractions from the Heparin Sepharose CL6B column. Protein bands are detected by Coomassie Blue stain.

Following hydroxylapatite chromatography, DAGAT activity is not stable to freeze/thaw so fractions are assayed immediately and active fractions are pooled for further chromatography. The pool is diluted with Buffer C to lower the KCl concentration from 500 mM to 150 mM KCl. The diluted pool is loaded on a Heparin column (0.55×4.7 cm) equilibrated with 150 mM KCl in Buffer C. Protein and DAGAT activity are eluted during a 10 ml gradient of 150-500 mM KCl in Buffer C followed by a 10 ml wash with 500 mM KCl in Buffer C. DAGAT activity elutes in two peaks, a sharp peak is found during the KCl gradient and another broader peak during the wash (FIG. 11A). A portion of the fractions containing the DAGAT activity peak are run on gradient gel SDS-PAGE and are silver-stained. The pattern of bands eluting from the column is compared, fraction by fraction, to the respective DAGAT activity profile. Examination of the stained protein bands indicate a protein at 36 kDa correlates best with DAGAT activity found in the broad peak (FIG. 11B). Several proteins (of approximately 36.5 kDa, 35 kDa, 34 kDa) are associated with activity found in the sharp peak. The candidates at about 33 kDa and about 31 kDa do not appear to correlate with DAGAT activity. Table 1 demonstrates the fold purification from the 1500×g fraction through Heparin.

TABLE 1

| Fraction | Protein Activity mg | nmol/min | Specific activity nmol/min/mg | Fold Purification |
|---|---|---|---|---|
| 1500 g | 585.3 | 304.5 | 0.5 | 1.0 |
| LBF/Tx-100 | 67.4 | 714.8 | 10.6 | 20.4 |
| TX-100 extract | 29.4 | 517.3 | 17.6 | 33.8 |
| Yellow Load | 15.9 | 364.7 | 22.9 | 44.1 |
| Yellow Ft/wash | nd | 179.8 | nd | nd |
| Yellow Eluted | 0.4 | 169.5 | 440.3 | 846.2 |
| Four Yellow columns were pooled for further chromatography | | | | |
| Yellow Pool | 1.54 | 437.1 | 283.9 | 545.5 |
| HA Pool | 0.56 | 340.2 | 607.6 | 1167.6 |
| Heparin | 0.20 | 264.6 | 1323.0 | 2646.0 |
| Heparin#22 MR-2 | 0.026 | 51.0 | 1961.5 | 3769.5 |
| Heparin#28 MR-1 | 0.0076 | 20.0 | 2631.6 | 5057.2 |

The four candidates identified (at about 36.5 kDa, 36 kDa, 35 kDa and 34 kDa) are prepared for in-gel digestion by precipitating fractions from the Heparin column as described in Example 8B and separated by gradient gel SDS-PAGE as described in Example 8C. In this manner, peptide maps are obtained from each of the DAGAT candidates and individual peptides are selected for protein sequencing.

D. Chromatography on Yellow 86-Agarose with Gradient Elution

Figure 12A:
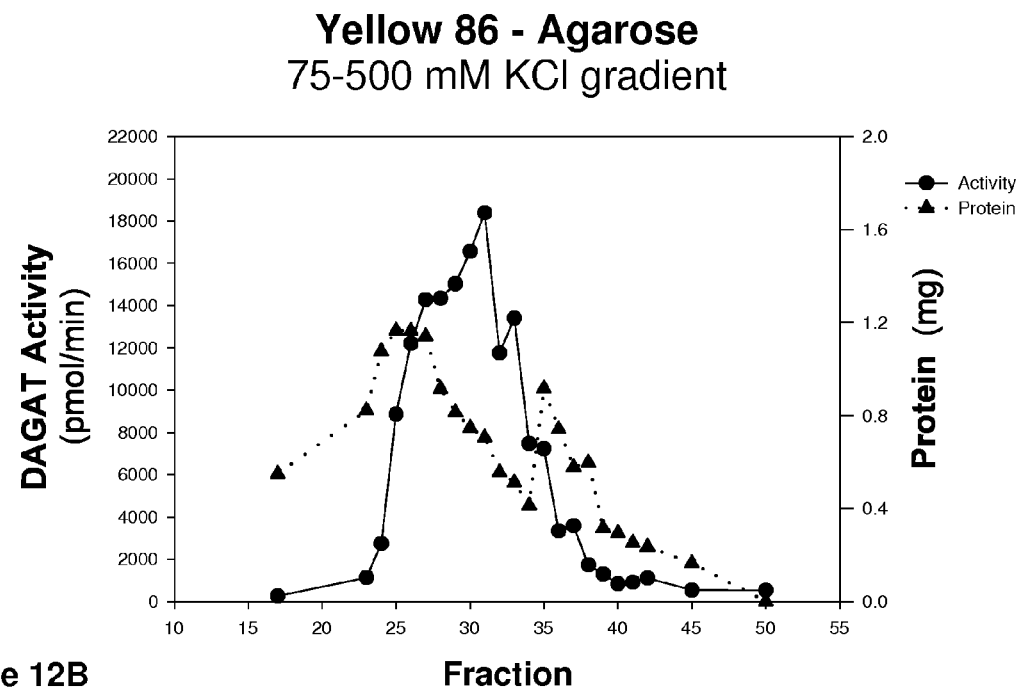
FIG. 12A shows the results of chromatography of *Mortierella ramanniana* DAGAT activity from the first activity peak of the Heparin Sepharose CL6B column chromatographed on a Yellow 86-Agarose column where protein was eluted during a gradient of 75-150 mM KCl.
Figure 12B:
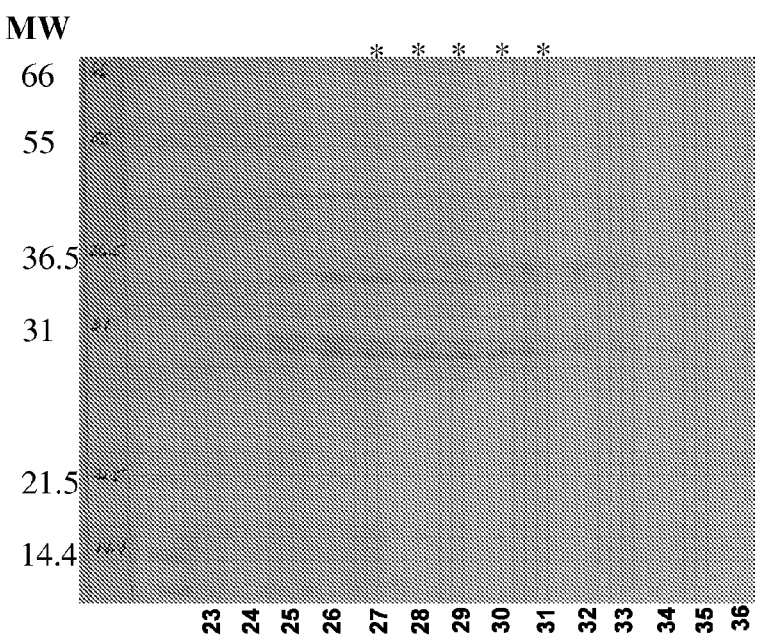
FIG. 12B shows SDS-PAGE analyses of fractions from the Yellow 86-Agarose column. Protein bands are detected by Coomassie Blue stain.

In order to examine another purification protocol DAGAT is purified through hydroxylapatite as described in Example 6A, diluted to 75 mM KCl and then applied to a Yellow 86-Agarose column (1.3×6.3 cm) equilibrated with 75 mM KCl in Buffer C. The column is washed with 25 ml of equilibration buffer and bound proteins are eluted over a 40 ml gradient of 75-500 mM KCl in Buffer C. Fractions are assayed for DAGAT activity as in Example 1B. DAGAT activity appears as a single peak in the middle of the gradient. Fractions containing DAGAT activity are concentrated by precipitation as in Example 8B and are separated by SDS-PAGE as in Example 8C. The pattern of bands eluting from the column are compared, fraction by fraction, to the respective DAGAT activity profile (FIG. 12A). The 34 kDa protein candidate elutes early in the gradient and does not appear to correlate with DAGAT activity (FIG. 12B). Three remaining protein candidates (of about 36.5 kDa, 36 kDa, and 35 kDa, designated Mr21, Mr22, Mr23, respectively) correlate with DAGAT activity.

Example 8

Preparation of Protein for In-Gel Digestion

After a protein candidate has been identified, it is necessary to prepare sufficient amounts for sequencing. Protein sequencing can be performed using a wide variety of methods known in the art. One technique involves digestion of the protein, using enzymes such as trypsin, while still in an SDS-polyacrylamide gel. Several commercial enterprises have established protocols for obtaining peptides in this manner. Following the generation of peptides, standard techniques are employed to separate and sequence them.

In order to gel-purify a protein candidate, it is often necessary to concentrate the liquid sample first so that it can be loaded on the gel. Samples containing high amounts of detergent may pose special problems. Depending on the micelle size of the detergent, it may concentrate during ultrafiltration and pose problems during electrophoresis. An alternative method of concentrating the protein sample must then be employed.

A. Preparation of Samples for SDS-PAGE by Concentration

Fractions can be concentrated in a pressure cell fitted with a membrane of the appropriate molecular weight retention limit. Alternatively, the sample may be concentrated using filtration by centrifugation in individual units, for example a product such as Centricon-30 (Amicon, Inc., Beverly, Mass.), to volumes of approximately 50 µl. Following concentration, samples can be treated with a loading buffer, for example, Laemmli.

B. Preparation of Samples for SDS-PAGE by Precipitation

Sometimes it is desirable to concentrate samples by precipitation. This can be achieved using acid and/or acetone. A typical protocol would be to add trichloroacetic acid (TCA) from a concentrated stock (40%-50% (w/v)) to a final concentration of 7-10% (w/v). After about 10 minutes on ice the samples are centrifuged (12,000×g, 15 minutes at 4 C) to pellet the precipitated protein. The supernatants are removed and in order to remove the precipitated detergent, the pellets are washed with ice cold acetone and centrifuged again. Precipitates can be resuspended with a sample loading buffer (ie. Laemmli or SDS-PAGE sample buffer as in Example 3). SDS-PAGE may be performed using gels cast in the laboratory, as described in Example 3 or from gels prepared by commercial sources.

C. SDS-PAGE

Heating of the samples prior to loading the gel may or may not be performed. It has been observed that some membrane proteins have a tendency to aggregate upon heating. In this case, samples are generally applied to the gel after sitting at room temperature for 15 minutes. Acrylamide gels may be purchased commercially or prepared in the laboratory. One protocol for preparing 10-13% (w/v) acrylamide gels is described in Example 3. Following electrophoresis, the gel can be stained with 0.1% (w/v) Coomassie Blue in 50% (v/v) methanol, 10% (v/v) acetic acid then destained. Destaining can be accomplished with the use of a commercial product, such as Gel-Clear (Novex, San Diego, Calif.) or in 50% (v/v) methanol, 10% (v/v) acetic acid. Protein candidates can then be excised from the gel and sent for in-gel digestion with or without further destaining.

Example 9

Determination of Amino Acid Sequence

Commercial facilities have been established which provide protein sequencing as a service. Among the techniques which are available, the generation of peptides by in-gel digestion using an endopeptidase, such as trypsin, followed by HPLC purification, has proved the most useful. N-terminal sequencing on PVDF, and to a lesser degree the generation of peptides by limited cyanogen bromide treatment of the PVDF proteins, has also proved successful. Procedures for in-gel digestion may include amino acid analysis of a portion (10-15%) of the gel slice for quantitation and amino acid composition, digestion of the protein with one of the proteolytic enzymes (trypsin or lysyl endopeptidase), and fractionation of the products by reverse phase HPLC. Absorbance peaks may be selected from the HPLC run and subjected to laser desorption mass spectrometry to determine the presence, amount, and mass of the peptide prior to protein sequencing. The longest peptides are selected for microsequencing. In particular, DAGAT candidates are gel purified and sent to Argo Bioanalytica (a commercial service) for in-gel digestion and microsequencing.

Example 10

Amino Acid Sequence of Trypsin Generated Peptides

Amino acid sequence of peptides generated from the approximately 36 kDa protein, also designated MR1, (see Examples 6C and 6D) by trypsin digestion as described in Example 9, are as follows (the first two digits of the sequence number designates the Mr bands described in examples 6C and 7C):

| sequence # | amino acid sequence | SEQ ID NO: |
|---|---|---|
| 19-138 | ELHDSYMHAV | 1 |
| 19-169 | kIqHALgFTMplFhgr | 2 |
| 19-181 | HPIYTiv | 3 |
| 18-146 | NAAwpk | 4 |
| 18-151 | VKELEFVE | 5 |
| 18-159-1 | FGF | 6 |
| 18-159-2 | yxhDayphave | 7 |
| 18-164 | ELHDSYMHAVQDLYDR | 8 |
| 18-208-1 | GVFNYDFGLLPHR | 9 |
| 18-208-2 | xlagifpa | 10 |
| 18-219-1 | IAVQTGAGLVPTLsF | 11 |
| 18-219-2 | sIAIVVgSASEsINA | 12 |
| 18-219-3 | gffNYDFxxl | 13 |
| 22-158 | ELHDSYMHAV | 14 |

Amino acid sequence of peptides generated from the approximately 36.5 kDa protein, also designated MR2, (see Example 7B) by trypsin digestion as described in Example 9, are as follows:

| sequence # | amino acid sequence | SEQ ID NO: |
|---|---|---|
| 21-134 | VHWAPLR | 15 |
| 21-149-1 | KLPLFk | 16 |
| 21-149-2 | VDIDxAPpR | 17 |
| 21-160-1 | ITGFTVPHAH | 18 |
| 21-160-2 | ELHDSHMLxV | 19 |
| 91-218 | GIFNYNAGFIPFR | 20 |
| 21-178 | hPIYTIVGKpipv | 21 |
| 21-101 | gsCEAILR | 22 |
| 21-221 | hPIVTVVGKPIAVpLLAegeteppse | 23 |
| 21-197 | sRDsTPVITEHKQPMeQvqvtalldhipv | 24 |

The amino acid sequence is represented using the one letter code. Amino acids represented by lower case letters represent residues which were identified with a lesser degree of confidence. The peptide map from the 35 kDa candidate, Mr23 in Example 7C, substantially similar to the peptide map of the 36.5 candidate, Mr21 in Example 7C.

The amino acid sequences in the peptides above are compared to known protein sequences in public and proprietary data bases. No significant homology is found between the DAGAT peptides and any sequence encoding an enzyme of known function including any portion of glyceraldehyde 3-phosphate (GAP) dehydrogenase which is known to migrate at about 36 kDa by SDS-PAGE.

Example 11

Identification of *Mortierella ramanniana* DAGAT Nucleic Acid Sequences

In general, for use as polymerase chain reaction (PCR) primers from single stranded DNA template reverse-transcribed from mRNA, oligonucleotides containing the sense orientation sequence corresponding to DAGAT peptide encoding sequences are prepared. For the "reverse" reaction for amplification of the encoding DNA strand, an oligonucleotide may be designed which contains sequence complementary to DAGAT peptide encoding sequence.

Alternatively, an oligonucleotide may be designed to be identical to a portion of a primer used to prepare DNA template for PCR. This oligonucleotide may be used as either the "forward" or "reverse" primer as described above.

Where the DAGAT peptide sequences contain amino acids which may be encoded by a number of different codons, the forward or reverse primers may be "degenerate" oligonucleotides, i.e. containing a mixture of all or some of the possible encoding sequences for a particular peptide region. To reduce the number of different oligonucleotides present in such a mixture, it is preferable to select peptide regions which have the least number of possible encoding sequences when preparing the synthetic oligonucleotide for PCR primers.

A. Identification of DAGAT MR1

To identify the nucleic acid sequence for *Mortierella ramanniana* DAGAT MR1, peptide 18-151 is used to design degenerate primer 5'-CACTGCAGACRAAYTCNARYT-CYTTNAC-3' (SEQ ID NO:25), peptide 18-208-1 is used to design primers 5'-CCAAGCTTGGNGTNTTYAAY-TAYGAYTTYG-3' (SEQ ID NO:26) and 5'-CACTG-CAGCRAARTCRTARTTRAANACNCC-3' (SEQ ID NO:27), peptide 18-164 is used to design primer 5'-CACTG-CAGCYTGNACNGCNGCRTGCATRTA-3' (SEQ ID NO:28), peptide 18-219-1 is used to design primer 5'-CCAAGCTTATHGCNGTNCARACNGGNGC-3' (SEQ ID NO:29), peptide 19-181 is used to design primers 5'-CCAAGCTTAARCAYCCNATHTAYACNAT-3' (SEQ ID NO:30) and 5'-CACTGCAGACDATNGTRTADATNG-GRTG-3' (SEQ ID NO:31), peptide 19-169 is used to design primers 5'-CCAAGCTTGCNYTNGGNTTYACNATGCC-3' (SEQ ID NO:32), 5'-CCAAGCTTTTYACNATGCCNYT-NTTYCA-3' (SEQ ID NO:33) and 5'-CACTGCAGAART-GRAANARNGGCATNGT-3' (SEQ ID NO:34).

DNA fragments obtained by PCR are analyzed for nucleic acid sequence encoding amino acid sequence found in the peptides in Example 10. To obtain the entire coding region corresponding to the *Mortierella ramanniana* DAGAT MR1 protein, synthetic oligo-nucleotide primers are designed to amplify the 5' and 3' ends of partial cDNA clones containing MR1 sequences. Primers are designed according to the *Mortierella ramanniana* DAGAT MR1 sequence and are used in Rapid Amplification of cDNA Ends (RACE) reactions (Frohman et al. (1988) *Proc. Natl. Acad. Sci. USA* 85:8998-9002). Amplification of flanking sequences from cDNA clones are performed using the Marathon cDNA Amplification kit (Clontech, Calif.). For example, PCR reactions can be performed with 3' PACE primer 5'-GGTTTGCTC-CCCCATCGCCATCCTATC-3' (SEQ ID NO:35) and 5' RACE primer 5'-GATAGGATGGCGATGGGGGAG-CAAACC-3' (SEQ ID NO:36). In this manner the complete MR1 encoding sequence of 1065 nucleotides is determined (SEQ ID NO:37). The predicted protein sequence for the MR1 DAGAT is also determined (SEQ ID NO:38) DAGAT nucleic acid sequences are obtained which may be analyzed for nucleic acid sequence and used for expression of DAGAT in various hosts, both procaryotic and eucaryotic.

The primers 5-AATTCGCGGCCGCATGGCCAG-CAAGGATCAACATTTACAGC-3' (SEQ ID NO:39) and 5'-TGCTGCAGCTATTCGACGAATTCTAGT-TCTTTTACCCGATCC-3' (SEQ ID NO:40) are used to PCR amplify the open reading frame (ORF) from *Mortierella ramanniana* Marathon cDNA library made according to the manufacturer's protocol (Clonetech). These primers introduce NotI and PstI restriction sites at the 5' and 3' ends of the ORF, respectively. The PCR product is cloned into plasmid pCR2.1 according to the manufacturer's protocol (Invitrogen) to yield plasmid pCGN8707. Double stranded DNA sequence is obtained to verify that no errors are introduced by PCR amplification. For expression of the *M. ramanniana* DAGAT MR1 protein in insect cells using a baculovirus expression system, the NotI-PstI fragment of pCGN8707 is cloned into NotI-PstI digested plasmid pFASTBAC1 (Gibco), and the resultant plasmid, pCGN8708, is transformed into *E. coli* DH10BAC (Gibco). The bacmid DNA is used to transfect insect cells. For expression of the *Mortierella ramanniana* DAGAT MR1 sequence in plants, the NotI-PstI fragment of pCGN8708 is cloned into NotI-PstI digested binary vector pCGN8622 to yield plasmid pCGN8709 under control of a napin promotor. Plasmid pCGN8709 is introduced in *Agrobacterium tumefaciens* EHA105.

B. Identification of DAGAT MR-2

To identify the nucleic acid sequence for *Mortierella ramanniana* DAGAT MR2, peptide 21-221 is used to design degenerate primer 5'-GGCACNGCDATNGGYTTNC-CNAC-3' (SEQ ID NO:41) and peptide 21-218 is used to design primer 5'-CCNGCRTTRTARTTRAADATNCC-3' (SEQ ID NO:42). These are used in a nested PCR as antisense primers in Rapid Amplification of cDNA Ends (RACE) reactions (Frohman et al. (1988) *Proc. Natl. Acad. Sci. USA* 85:8998-9002) using a cDNA library constructed with the Marathon cDNA Amplification kit (Clontech) according to the manufacturers instructions.

RACE amplification of the 5' region corresponding to the *Mortierella ramanniana* DAGAT MR2 protein is performed with primer 5'-TGCCTAGTGACATCATGAAATCTCG-3' (SEQ ID NO:43) using a cDNA library constructed with the Marathon cDNA Amplification kit (Clontech) according to the manufacturers instructions. In this manner the partial encoding sequence of nucleotides is determined (SEQ ID NO:44). A partial amino acid sequence for the MR2 protein is also predicted (SEQ ID NO:45).

Those skilled in the art will recognize that further RACE reactions will lead to the cloning the complete nucleic acid sequence which may be used for expression of DAGAT in various hosts, both procaryotic and eucaryotic.

C. Comparison of MR1 and MR2 Sequences

Analysis of the protein sequence alignments between the protein sequences of the *Mortierella ramanniana* DAGAT sequences MR1 (SEQ ID NO:38) and MR2 (SEQ ID NO:45) (FIG. 13) shows that they share 55% similarity.

Example 12

Identification of DAGAT Related Sequences

Since plant DAGATs are unknown in the art, the *Mortierella ramanniana* DAGAT nucleic acid and protein sequences are used to search public and proprietary EST databases as well as public genomic databases to identify other DAGAT-like sequences.

Three EST sequences can be identified by tblastn in the maize proprietary database, which are assembled into two contigs using the GCG assembly program (SEQ ID NO:46-47). One EST can be identified in each of the *Brassica napus* (SEQ ID NO:48) and soybean proprietary databases (SEQ ID NO:49). Two EST sequences can be identified in *Arabidopsis thaliana* proprietary databases (SEQ ID NO:50-51), and one proprietary genomic sequence (SEQ ID NO:52).

The MR1 protein sequence is used to search proprietary mouse and human databases. Results of this search identified approximately 45 EST sequences from Human, which are assembled into 5 contigs using the GCG assembly program (SEQ ID NO:53-57) and 12 from mouse, which are assembled into 3 contigs using the GCG assembly program (SEQ ID NO:58-60). Searches of proprietary *Aspergillus fumigatus* (SEQ ID NO:61 and 62), *Aspergillus oraceus* (SEQ ID NO:63), *Candida albicans* (SEQ ID NO:64), *Fusarium graminearum* (SEQ ID NO:65), *Morrierella alpina* (SEQ ID NO:66), and *Schizochytrium aggregatum* (SEQ ID NO:67), yield additional EST sequences.

Along with these EST sequences, database searches of the public predicted proteins from the genomic and amino acid sequence databases of *C. elegans* yield four similar sequences, W01A11.2 (SEQ ID NO:68), K07B1.4 (SEQ ID NO:69), F59A1.10 (SEQ ID NO:70), well as the protein sequence y53G8B_93.B (SEQ ID NO:71). Similar searches of the public *S. cerevisae* predicted protein database yields one sequence, YOR245c (SEQ ID NO:72).

Total RNA was collected from these two organisms, and a 1$^{st}$ strand cDNA library was created using the Marathon cDNA library kit (Clontech.) The primers 5'-GCGCGGC-CGCCTGCAGTCACTGGAAGATGAG-3' (SEQ ID NO:73) and 5'-GCGCGGCCGCATGAGACTCCGGCT-GAGCTCG-3' (SEQ ID NO:74) are used to PCR amplify the W01A11.2 from the *C. elegans* cDNA library. Primers 5'-GAGCGGCCGCATGCCACATCTACTAGGAGTTGA-3' (SEQ ID NO:75) and 5'-CGGCGGCCGCCTGCAGT-TAATTGATAACAAGTTGT-3' (SEQ ID NO:76) are used to PCR amplify the CEK07B1.4 2 from the *C. elegans* cDNA library. 5'-GCGCGGCCGCATGCTAAACTACCAAAT-TCACA-3' (SEQ ID NO:77) and 5'-TGGCGGCCGCCTG-CAGTCACTGAAAAACGAGCC-3' (SEQ ID NO:78) are used to PCR amplify the CEF59A 1.10 2 from the *C. elegans* cDNA library. Primers 5'-CAGCGGCCGCATGTCAG-GAACATTC-3' (SEQ ID NO:79) and 5'-CACTGCAGT-TACCCAACTATCTTCAA-3' (SEQ ID NO:80) are used to PCR amplify the YOR245c from the *S. cerevisae* cDNA library. The PCR products were cloned into pCR2.1 TOPO according to the manufacturer's protocol (Invitrogen), and these sequences were verified.

Example 13

Sequence Comparisons

Sequence alignments between DAGAT-like sequences from several different sources are compared to identify the similarity between the sequences.

The longer sequences are aligned using the Clustal Algorithm in DNASTAR. The following percent similarity values are obtained as compared to the MR1 sequence:

| | |
|---|---|
| ATgC-A1X01ds10429d10a1 | 19.8% |
| ATLIB22-029-Q1-E1-G7 | 19.0% |
| ATLIB24-124-Q1-E1-E2 | 16.8% |
| BNLIB3034-036-Q1-E1-C3 | 18.2% |
| CEF59A1.10 | 37.1% |
| CEK07B1.4 | 36.3% |
| CEW01A11.2 | 39.0% |
| HS4371967H1CON | 42.0% |
| HS4818474H1 | 25.9% |
| MALIB26-037-Q1-E1-D8 | 41.6% |
| MMg2813274 | 32.4% |
| MMg2892216 | 30.2% |
| MMg2989686 | 38.7% |
| MR2 | 53.9% |
| ZMLIB3136-059-Q1-K1-F10 | 14.6% |
| GM701121562H1 | 15.2% |

The protein sequences that contain a conserved region corresponding to bases 355 to 796 of MR1 are aligned and truncated to this region, the following percent similarity is achieved.

| | |
|---|---|
| AF804547551F1 | 35.1% |
| ATgC-A1X01ds10429d10a1 | 22.3% |
| ATLIB22-029-Q1-E1-G7 | 20.0% |
| ATLIB24-124-Q1-E1-E2 | 18.8% |
| BNLIB3034-036-Q1-E1-C3 | 19.0% |
| CA803535474F1 | 33.6% |
| CEF59A1.10 | 44.9% |
| CEK07B1.4 | 46.3% |
| CEW01A11.2 | 50.3% |
| GM701121562H1 | 25.4% |
| HS4371967H1CON | 52.4% |

| | |
|---|---|
| MALIB26-037-Q1-E1-D8 | 55.6% |
| MMg2989686 | 49.7% |
| MR2 | 60.3% |
| SCYOR245c | 42.4% |
| ZMLIB3136-059-Q1-K1-F10 | 26.3% |

Example 14

Expression Constructs

A. Baculovirus Expression Constructs

Constructs are prepared to direct the expression of the *M. ramanniana* DAGAT protein in cultured insect cells. The NotI-PstI fragment of pCGN8707 is cloned into NotI-PstI digested plasmid pFASTBAC1 (Gibco), and the resultant plasmid, pCGN8708, is transformed into *E. coli* DH10BAC (Gibco). The bacmid DNA is used to transfect insect cells.

B. Plant Expression Construct Preparation

Constructs which provide for expression of DAGAT sequences in plant cells may be prepared as follows.

A plasmid containing the napin cassette derived from pCGN3223 (described in U.S. Pat. No. 5,639,790, the entirety of which is incorporated herein by reference) is modified to make it more useful for cloning large DNA fragments containing multiple restriction sites, and to allow the cloning of multiple napin fusion genes into plant binary transformation vectors. An adapter comprised of the self annealed oligonucleotide of sequence 5'-CGCGATTTAAATG-GCGCGCCCTGCAGGCGGCCGCCTG-CAGGGCGCGCCATTTAAAT-3' (SEQ ID NO:81) is ligated into the cloning vector pBC SK+ (Stratagene) after digestion with the restriction endonuclease BssHII to construct vector pCGN7765. Plasmids pCGN3223 and pCGN7765 are digested with NotI and ligated together. The resultant vector, pCGN7770, contains the pCGN7765 backbone with the napin seed-specific expression cassette from pCGN3223.

The plasmid pCGN8618 is constructed by ligating oligonucleotides 5'-TCGAGGATCCGCGGCCGCAAGCTTC-CTGCAGG-3' (SEQ ID NO:82) and 5'-TCGACCTGCAG-GAAGCTTGCGGCCGCGGATCC-3' (SEQ ID NO:83) into SalI/XhoI-digested pCGN7770. A fragment containing the napin promoter, polylinker and napin 3' region is excised from pCGN8618 by digestion with Asp718I; the fragment is blunt-ended by filling in the 5' overhangs with Klenow fragment then ligated into pCGN5139 that has been digested with Asp718I and HindIII and blunt-ended by filling in the 5' overhangs with Klenow fragment. A plasmid containing the insert oriented so that the napin promoter is closest to the blunted Asp718I site of pCGN5139 and the napin 3' is closest to the blunted HindIII site is subjected to sequence analysis to confirm both the insert orientation and the integrity of cloning junctions. The resulting plasmid is designated pCGN8622.

The NotI/PstI fragment of pCGN8708 containing the entire DAGAT encoding region is ligated into NotI/PstI digested pCGN8622 to provide the expression construct pCGN8709 having the *Mortierella ramanniana* DAGAT encoding sequence positioned for transcription of the sense sequence under regulation of the napin promoter.

In addition, the MR1 nucleic acid sequence is resynthesized (SEQ ID NO:84) for plant preferred codon usage and used to produce expression constructs for transformation into host plant cells.

Binary vector constructs are transformed into *Agrobacterium* cells, such as of strain EHA105 (Hood et al., *Transgenic Research* (1993) 2: 208-218), by the method of Holsters et al. (*Mol. Gen. Genet.* (1978) 163: 181-187) and used in plant transformation methods as described below.

Example 15

Expression of DAGATs in Insect Cell Culture

A baculovirus expression system is used to express the full length 36 kDa *Mortierella ramanniana* cDNA encoding a putative DAGAT in cultured insect cells.

The baculovirus expression construct pCGN8708 (see Example 14A) is transformed and expressed using the BAC-to-BAC Baculovirus Expression System (Gibco-BRL, Gaithersburg, Md.) according to the manufacturers directions, except harvesting of recombinant viruses was done 5 days post-transfection. The supernatant from the transfection mixture is used for generating virus stock which in turn is used for infecting Sf9 cells for use in the assay.

A. Assay of DAGAT Enzyme Activity in Insect Cell Culture Membranes

The transformed insect cells can be assayed for DAGAT or other acyltransferase activities using methods described herein. Insect cells are centrifuged and the resulting pelletted cells may either be used immediately or be stored at −70 C for later analysis. Cells are resuspended in Medium I (100 mM Tricine/NaOH, pH 7.8, 10% (w/v) glycerol, 280 mM NaCl with: 0.1 µM Aprotinin, 1 µM Leupeptin, and 100 µM Pefabloc (all from Boehringer Mannheim, Germany) and lysed by sonication (2×10 sec). Cell walls and other debris are pelleted by centrifugation (14,000×g, 10 min, 4° C.). The supernatant is transferred to a new vial and membranes are pelleted by centrifugation (100,000×g, Ti 70.1 rotor, 46,000 rpm for 1 hour at 4° C.). Total membranes are resuspended in Medium I. DAGAT activity is assayed in a 0.1 ml reaction mixture containing 30 mM Tricine/NaOH, pH 7.8, 56 mM NaCl, 10 mM MgCl2, 0.2 mM 1,2-diolein in 2-methoxyethanol, 25 mM 1-$^{14}$C-palmitoyl-CoA (17,600 dpm/mole), and 0.2-30 mg of membrane protein. The 5 minute reaction is terminated by addition of a 1.5 ml solution of isopropanol: heptane:0.5M sulfuric acid (80:20:2, v/v/v). The reaction mixture may be stored at 4° C. or processed immediately as described in Example 1C.

Figure 14:
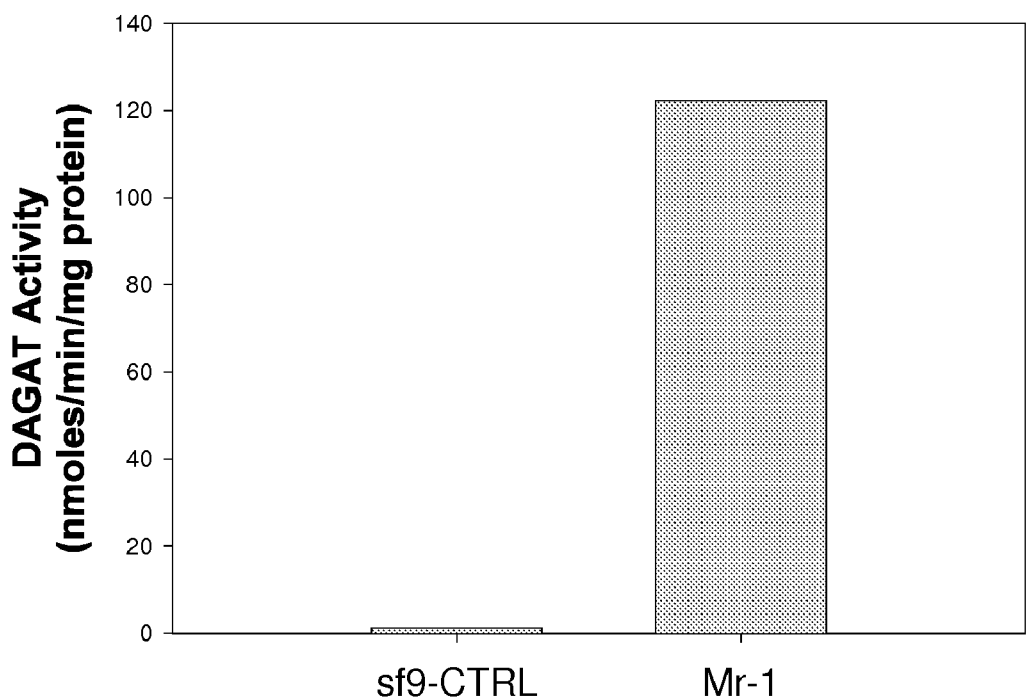
FIG. 14 shows DAGAT activity data on membranes isolated from insect cells infected with either an empty pFASTBAC vector or a pFASTBAC vector containing DNA sequence of the 36 kDa DAGAT sequence identified in *Mortierella ramanniana*.

The 36 kDa *Mortierella* candidate, when expressed in insect cells, demonstrates a 94-fold greater DAGAT activity than the control membranes isolated from insect cells infected with an empty vector (FIG. 14). The result of the DAGAT activity assay demonstrates that this *Mortierella ramanniana* DNA sequence encodes a protein with DAGAT activity.

Figure 15:
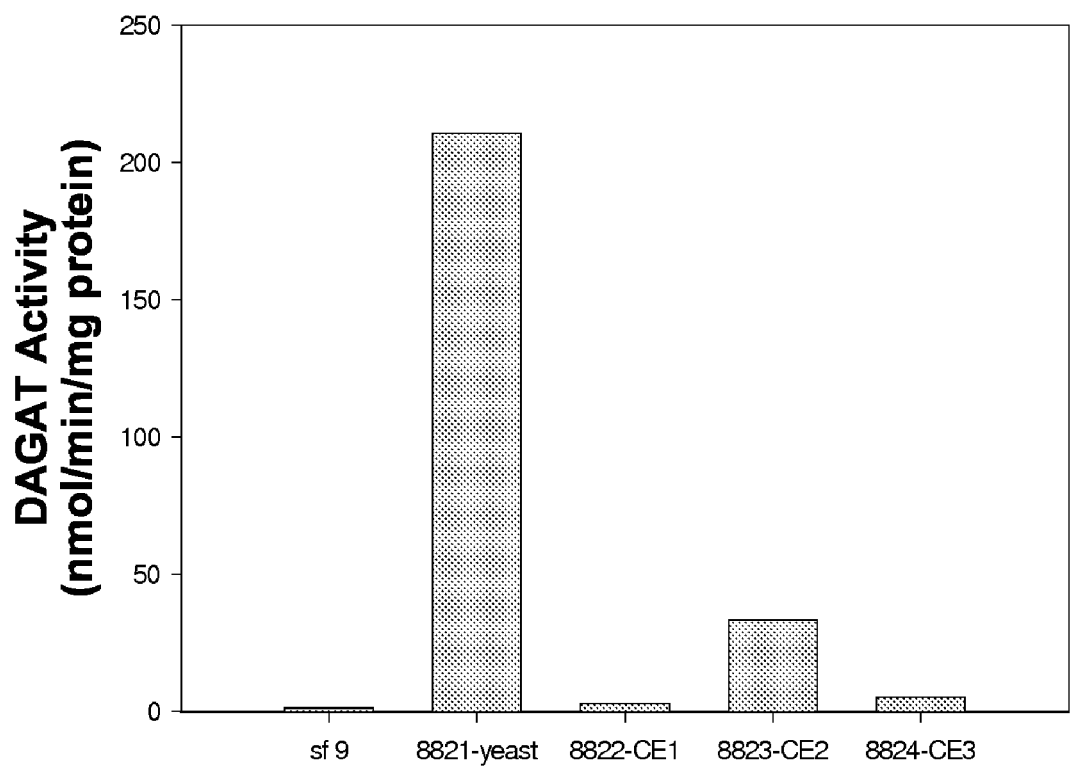
FIG. 15 shows DAGAT activity data on membranes isolated from insect cells infected with either an empty pFASTBAC vector or a pFASTBAC vector containing DNA sequence of DAGAT homologues from yeast and *C. elegans*.

Similarly, homologues of DAGAT identified from yeast (SCYOR245c) and *C. elegans* (CEK07B1.4, CEF59A1.10, AND CEWOLA1.2) were also cloned into the pFASTBAC1 (Gibco) vector to create baculoviral expression constructs pCGN8821, pCGN8822, pCGN8823, and pCGN8824, respectively. Results of DAGAT enzyme activity assays demonstrate significant increases in DAGAT enzyme activity over control vectors when expressed in insect cells (FIG. 15). For example, membranes isolated from insect cells infected with a vector for the expression of the yeast homologue sequence have greater than a 95 fold increase in DAGAT enzyme activity compared to control membranes isolated from insect cells infected with an empty vector (FIG. 15). Furthermore, membranes isolated from insect cells infected with a vector for the expression of the *C. elegans* homologue sequence (pCGN8823) have about a 15 fold increase in DAGAT enzyme activity (FIG. 15). Thus, additional DAGAT encoding sequences can now be readily identified using the sequences of the present invention.

B. Triacylglycerol Production in Insect Cell Culture

The transformed insect cells can be assayed for triacylglycerol, phosphotidyl choline or other lipid classes by methods described herein. An insect cell culture suspension is diluted to a standard optical density of 0.3 to 0.6 at an absorbance of 600 mm with culture medium. A sample of 4.5 ml of culture suspension in culture medium is added 200 µl glacial acetic acid, internal standards consisting of 12.5 ug c17:0 TAG and 25 ug c15:0 PC, and 10 ml of cholorform:methanol (1:1, v/v). After vortexing, the phases are separated by centrifugation (about 500×g, 5 min.). The lower, organic phase (OP1) is saved and the upper, aqueous phase is re-extracted with the lower, organic phase of a mixture of 200 µl glacial acetic acid, 10 ml of cholorform:methanol (1:1, v/v), and 4.5 ml water. The samples are again vortexed and centrifuged to separate the phases. The lower, organic phase is saved (OP2). The OP1 is filtered through a 0.45 µm filter and the filter is rinsed with OP2. The filtrates are combined and concentrated under nitrogen gas to a final volume of 0.4 ml. Twenty-five percent of the final volume is spotted onto a hard layer silica gel GHL TLC plate with inorganic binder (Alltech Associates, Inc., Newark, Del.). The TLC plate is developed for 30 minutes in hexane:diethyl ether:acetic acid (80:20:2, v/v/v) containing 20 mg/100 ml propyl gallate as an antioxidant. After the plate is dried, it is sprayed with 0.001% primuline in 80% acetone and the lipid bands are identified under UV light. The TAG and phospholipid bands are scraped from the TLC plate into glass vials. The samples are methanolyzed in 2 ml 5% $H_2SO_4$ in methanol at 90° C. for 2 hours. After samples have cooled, 2 ml 0.9% NaCl and 0.50 ml hexane are added. After the sample is vortexed, centrifuged to separate the phases, and the top hexane layer is taken for analysis of fatty acid methyl esters (FAME) by as chromatography using methods well known in the art.

Figure 16:
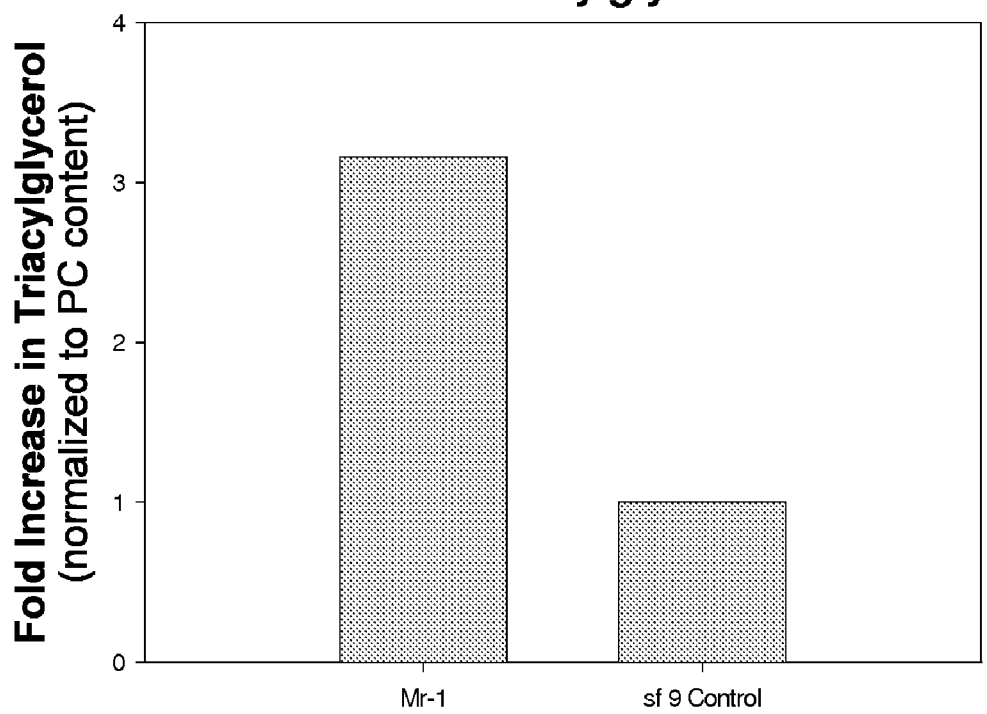
FIG. 16 shows the relative triacylglycerol content in insect cells infected with either an empty pFASTBAC vector or a pFASTBAC vector containing DNA sequence of the 36 kDa DAGAT sequence identified in *Mortierella ramanniana*.

The 36 kDa *Mortierella* candidate, when expressed in insect cells, demonstrates a 3.15 fold increase in triacylglycerol content compared to control culture of insect cells infected with an empty vector (FIG. 16). For comparison, the assays were normalized for cell phospholipid content. The result of the triacylglycerol analysis demonstrates that this *Mortierella ramanniana* DNA sequence encodes a protein that leads to triacylglycerol production.

Example 16

Plant Transformation

A variety of methods have been developed to insert a DNA sequence of interest into the genome of a plant host to obtain the transcription or transcription and translation of the sequence to effect phenotypic changes.

Transgenic *Brassica* plants are obtained by *Agrobacterium*-mediated transformation as described by Radke et al. (*Theor. Appl. Genet.* (1988) 75:685-694; *Plant Cell Reports* (1992) 11:499-505). Transgenic *Arabidopsis thaliana* plants may be obtained by *Agrobacterium*-mediated transformation as described by Valverkens et al., (*Proc. Nat. Acad. Sci.* (1988) 85:5536-5540), or as described by Bent et al. ((1994), *Science* 265:1856-1860), or Bechtold et al. ((1993), *C.R. Acad. Sci, Life Sciences* 316:1194-1199). Other plant species may be similarly transformed using related techniques.

Alternatively, microprojectile bombardment methods, such as described by Klein et al. (*Bio/Technology* 10:286-291) may also be used to obtain nuclear transformed plants.

Seeds or other plant material from transformed plants may be analyzed for DAGAT activity using the DAGAT assay methods described in Examples 1 and 7.

The above results demonstrate the ability to obtain partially purified DAGAT proteins which are active in the formation of triacylglycerols from fatty acyl and diacylglycerol substrates. Methods to obtain the DAGAT proteins and amino acid sequences thereof are provided. In addition DAGAT nucleic acid sequences may also be obtained from the amino acid sequences using PCR and library screening methods provided herein. Such nucleic acid sequences may be manipulated to provide for transcription of the sequences and/or expression of DAGAT proteins in host cells, which proteins can be used for a variety of applications. Such applications include the modification of triacylglycerols levels and compositions in host cells.

Example 17

Isolation of DGAT2 Nucleic Acid Sequences and Confirmation of DGAT Activity

*M. ramanniana* is cultured as described by Kamisaka, Y., et al., 28 *Lipids* 583-587 (1993) (herein incorporated by reference). Cells are harvested by passing 10-13 day old cultures through Miracloth and removing excess liquid by hand wringing. Wet packed cells are stored at −70° C. Lipid bodies are isolated from 70-75 g of wet packed cells. Immediately prior to use, cells are thawed on ice and resuspended in 200 mL of Buffer D (10 mM potassium phosphate (pH 7.0), 1 M KCl, 0.5 M sucrose, 1 mM EDTA). Samples are lysed with an equal volume of 0.5 mm glass beads in a cell disrupter (Bead-Beater, Biospec Products, Bartlesyille, Okla.) set on 'Homogenize' for 45-90 seconds. The cell slurry containing glass beads is centrifuged at 500×g, the supernatant removed, and the pellets washed with another 5 mL of Buffer D. Following centrifugation, the supernatants from both centrifugations are combined. It is divided into six ultracentrifuge tubes (25×89 mm) and each is overlaid with 5 mL of Buffer E (10 mM potassium phosphate, pH 7.0, 1 M KCl, and 0.3 M sucrose). Samples are centrifuged at 100,000×g at 4° C. for 3 hours. The lipid body fractions, floating on top of the overlays, are combined and solubilized in the 50 mL of Buffer F (10 mM potassium phosphate (pH 7.0), 75 mM KCl, 0.5 M Sucrose and 1.5% Triton X-100). Non-solubilized material is removed by ultracentrifugation (90,000×g for 1.8 hours). The floating lipid layer is discarded and the supernatant containing the solubilized fraction (Triton X-100 extract) is retained for column purification.

DAGAT activity is measured as the production of $^{14}C$ triacylglycerol from [1-$^{14}C$]oleoyl-CoA and unlabeled dioleoyl-DAG. For non-solubilized samples the reaction mixture (0.1 mL) consists of enzyme extract, 3.67 µM [1-$^{14}C$]oleoyl-CoA, and 1.5 mM 1,2-18:1 diacylglycerol in a buffer containing 10 mM potassium phosphate (pH 7.0), 100-150 mM KCl, and 0.1% Triton x-100 (w/v). Assay mixtures are incubated at 25° C. for 5 minutes and reactions are terminated by adding 1.5 mL of heptane:isopropanol:0.5 M $H_2SO_4$ (10:40:1, v/v/v). For solubilized samples 1,2-18:1 DAG is reduced to 0.5 mM, Triton X-100 is increased to 0.2%, and 300 µM L-a-phosphatidic acid is included. The L-a-phosphatidic acid is required to recover activity following solubilization with detergent as described by Kamiska et al., 119 *J. Biochem.* 520-523 (1996) (herein incorporated by reference), except 300 μM phosphatidic acid is used rather than 500 μM. This results in a greater stimulation of activity. Following solubilization, product formation is dependent on the addition of exogenous DAG. Under these conditions the reaction rate is linear with respect to time for up to 10 minutes.

After the assay is stopped, radiolabeled glycerolipids are isolated by adding 0.1 mL of 1 M NaHCO$_3$ and 1 mL of heptane containing 15 nmoles/mL triolein as a carrier. The mixture is vortexed and the upper organic phase is removed to a new glass vial. The organic extract is back-extracted with 1 mL of 1 M NaCl. Forty percent of the final organic phase is removed for liquid scintillation counting and the remaining organic phase evaporated to dryness under nitrogen gas. The residue is resuspended in hexane and subjected to TLC on silica gel-G with a preadsorbent loading zone (Analtech #31011, Newark, Del.). The TLC plate is developed in hexane:diethyl ether:acetic acid (50:50:1, v/v/v), before drying and scanning by a radio-image analyzer (AMBIS 3000, San Diego, Calif.) to determine the portion of radioactivity incorporated into TAG. Confirmation of TAG activity on the TLC plate is determined by co-migration of the unlabeled triolein carrier and the [$^{14}$C]TAG following exposure to iodine vapor.

DGAT activity in the Triton X-100 extract is further purified by dye-binding chromatography on a Yellow 86-Agarose column (2.5 cm×6.4 cm) equilibrated with 75 mM KCL in Buffer G (10 mM potassium phosphate (pH 7.0), 0.1% (w/v) Triton X-100, 10% (w/v) glycerol). The column is washed with 5 volumes of equilibration buffer at 2 mL per minute, then activity is eluted with 500 mM KCl in Buffer G. DGAT activity is stable to freeze or thaw at this stage of purification, so eluted fractions are assayed immediately and active fractions are stored at −70° C. Four preparations of Yellow 86-Agarose purified activity are combined and concentrated 12-fold by ultrafiltration (YM-30 membrane, Amicon, Beverly, Mass.). The activity is further purified by hydroxyapatite chromatography on a 1.0 cm×25.5 cm column equilibrated with 500 mM KCl in Buffer G. The column is washed with 40 mL of equilibration buffer before bound proteins are eluted with a step gradient to 100 mM di-potassium phosphate in the equilibration buffer. Fractions containing DGAT activity are pooled and diluted 1:3.3 in Buffer G to reduce the KCl concentration from 500 to 150 mM. The diluted sample was applied to a Heparin column (0.55×4.7 cm) equilibrated with 150 mM KCl in Buffer G. The column is washed with 5 volumes of equilibration buffer at 0.5 mL/minute and bound proteins are eluted in a 10 mL linear gradient of 150-500 mM KCl followed by 10 mL of 500 mM KCl in Buffer G at 0.25 mL/minute. Fractions of 1.1 mL are collected.

The protein concentration of extracts is determined according to Bradford, M., 72 *Anal. Biochem.* 248 (1976) (herein incorporated by reference) using bovine serum albumin as standard.

Polyacrylamide gradient gel electrophoresis (10-13%) is carried out according to the method of Laemmli, 227 *Nature* 680-685 (1970) (herein incorporated by reference) with some of the modifications of Delepelaire, 76 *Proc. Nat. Acad. Sci.* 115-115 (1979) (herein incorporated by reference). The resolving gel contains a 10-13% linear gradient of acrylamide stock stabilized by a 0-10% linear gradient of sucrose. Proteins are visualized by staining with silver according to the method of Blum et al., 8 *Electrophoresis* 93-99 (1987) (herein incorporated by reference), or with Coomassie Blue (0.1% Coomassie Blue R-250, 50% methanol (v/v), 10% acetic acid (v/v)).

Proteins in active fractions eluting from the Heparin step are precipitated with 10% trichloroacetic acid, washed with ice-cold acetone and resuspended in SDS sample buffer. Samples are subjected to SDS-PAGE and the gel is stained with Coomassie Blue. Protein bands at apparent molecular masses of 36 kD and 36.5 kD are excised from the gel and sent to a commercial laboratory (for example, Argo Bioanalytica, Morris Plains, N.J.) for analysis. Gel slices are digested in situ with trypsin and the resulting peptides are separated by reversed-phase HPLC. Amino acid sequencing is performed on a 473 Protein Sequencer (Applied Biosystems, Foster City, Calif.).

Total RNA is prepared from wet packed cells essentially as described by Jones et al., 7 *The Plant Cell* 359-371 (1995) (herein incorporated by reference). The RNA is then used to synthesize a double stranded amplified cDNA Amplification Kit (Clontech Laboratories, Inc. Palo Alto, Calif.).

Degenerate oligonucleotides are synthesized on an oligonucleotide synthesizer (Applied Biosystems model 394) and used as primers in polymerase chain reaction. The peptide sequences used for synthesizing the corresponding coding and complementary oligonucleotides are designated according to the partial amino acid sequence obtained. Marathon cDNA can be used as a template. An amplification mixture consists of template, polymerase chain reaction buffer, 200-300 ng of each primer, 2.5 mM dNTP, and 1 unit of AmpliTaq Gold polymerase (Perkin Elmer, Norwalk, Conn.) in 50 μL. The amplification program consists of one 10 minute hold at 95° C., 30 cycles of denaturation (94° C., 30 seconds), annealing (62° C., 10 seconds, 10% ramp to 50° C., 15 seconds), and primer extension (72° C., 2 minutes). Products of the reaction are separated on a 0.7% agarose gel, excised, and purified according to the QIAPREP DNA extraction handbook (Qiagen, Santa Clara, Calif.). The purified products are cloned into the pCR2.1TOPO vector (Invitrogen, Carlsbad, Calif.).

RACE reactions are completed according to the instruction manual for Marathon cDNA Amplification Kit using oligonucleotides designed from the products of the degenerate PCR. Gel-purified RACE products are cloned into the pCR2.1-TOPO vector.

Database searches of the predicted proteins from the public genomic databases of *C. elegans* yielded three similar sequences. Searches of the *S. cerevisiae* predicted protein database yielded one sequence. Searches of *Arabidopsis* EST databases yielded partial sequences that were sufficient for PCR primer design. Total RNA is collected from these three organisms and first strand cDNA libraries are created using the Marathon cDNA library kit (Clontech). The primers in Table 2 are used to PCR amplify each of the sequences. The PCR products are cloned into the pCR2.1-TOPO vector.

TABLE 2

PRIMER SEQUENCES USED TO CLONE DGAT2 HOMOLOGUES

| Organism | Genbank No. | Primer sequences |
|---|---|---|
| C. elegans | gi: 146580 | 5'-GCGCGGCCGCCTGCAGTCACTGGAAGATGAG-3'<br>5'-GCGCGGCCGCATGAGACTCCGGCTGAGCTCG-3' |
| C. elegans | gi: 2088817 | 5'-GAGCGGCCGCATGCCACATCTACTAGGAGTTGA-3'<br>5'-CGGCGGCCGCCTGCAGTTAATTGATAACAAGTTGT-3' |

TABLE 2-continued

PRIMER SEQUENCES USED TO CLONE DGAT2 HOMOLOGUES

| Organism | Genbank No. | Primer sequences |
|---|---|---|
| C. elegans | gi: 1914359 | 5'-GCGCGGCCGCATGCTAAACTACCAAATTCACA-3'<br>5'-TGGCGGCCGCCTGCAGTCACTGAA.AAACGAGCC-3' |
| S. cerevisiae | gi: 1420557 | 5'-CAGCGGCCGCATGTCAGGAACATTC-3'<br>5'-CACTGCAGTTACCCAACTATCTTCAA-3' |
| A. thaliana | gi: 6572057 | 5'-AACTCGAGCTGCAGATGGGTGGTTCCAGAG-3'<br>5'-AGCGGCCGCTCGAGTCAAAGAATTTTCAGC-3' |

DNA sequence determinations are carried out using a modified protocol from Applied Biosystems. Sequence analyses are carried out using software of the Gen Codes Corporation (Ann Arbor, Mich.).

A commercial BAC-to-BAC Baculovirus Expression System (Life Technologies, Inc., Gaithersburg, Md.) is used to express full-length proteins in cultured insect (sf9) cells. Full-length DGAT2 open reading frames are amplified by PCR employing primers containing restriction sites at the 5' ends (NotI and SpeI to the sense primers and PstI to the antisense primers). The PCR products are cloned into the pCR2.1TOPO vector and sequenced to confirm the fidelity of the constructs. Full-length cDNA in pCR2.1-TOPO vectors are digested with NotI and PstI and cloned into the NotI and PstI restriction sites of the pFASTBAC1 vector (Life Technologies, Inc., Gaithersburg, Md.).

Insect cells ($1 \times 10^6$ cells/mL) are infected at a multiplicity of infection (MOI) of 0.05-0.1 and harvested after 5 days at 27° C. by centrifugation. Pelleted cells are resuspended in Buffer H (100 mM Tricine-NaOH, pH 7.8, 10% glycerol, 100 mM NaCl) and lysed by sonication (2×10 seconds). Cell walls and other debris are pelleted by centrifugation and discarded. Membranes are harvested by centrifugation of the supernatant fraction (100,000×g for one hour) and pellets are resuspended in Buffer H for enzyme assay. Assays are linear with respect to protein and time.

Transformed insect cells are assayed for triacylglycerol and phosphatidylcholine by the following methods: an insect cell culture suspension is diluted to a standard optical density (usually 0.5) at an absorbance of 600 nm with a culture medium. A volume of 200 µl glacial acetic acid, internal standards consisting of 12.5 µg C17:0 TAG and 25 µg C15:0 PC, and 10 mL of chloroform:methanol (1:1, v/v) are added to a sample of 4.5 mL of insect cells in culture medium. After vortexing, the phases are separated by centrifugation (about 500×g, 5 minutes). The lower, organic phase is saved and the upper, aqueous phase is re-extracted. The two organic extracts are combined and evaporated under nitrogen gas to a final volume of 0.4 mL. Twenty-five percent of the final volume is spotted onto a hard layer silica gel-GHL TLC plate with inorganic binder (Alltech Associates, Inc., Newark, Delaware). The TLC plate is developed for 30 minutes in hexane:diethyl ether:acetic acid (80:20:2, v/v/v) containing 20 mg/100 mL propyl gallate as an antioxidant. The plate is dried, sprayed with 0.001% primuline in 80% acetone and the lipid bands are identified under UV light. The TAG and phospholipid bands are scraped from the TLC plate into glass vials. The samples are methanolyzed in 2 mL 5% $H_2SO_4$ in methanol at 90° C. for 2 hours. After cooling, 2 mL 0.9% NaCl and 0.50 mL hexane are added and the top hexane layer analyzed for fatty acid methyl esters (FAME) by gas chromatography according to Jones et al.

Figure 17:
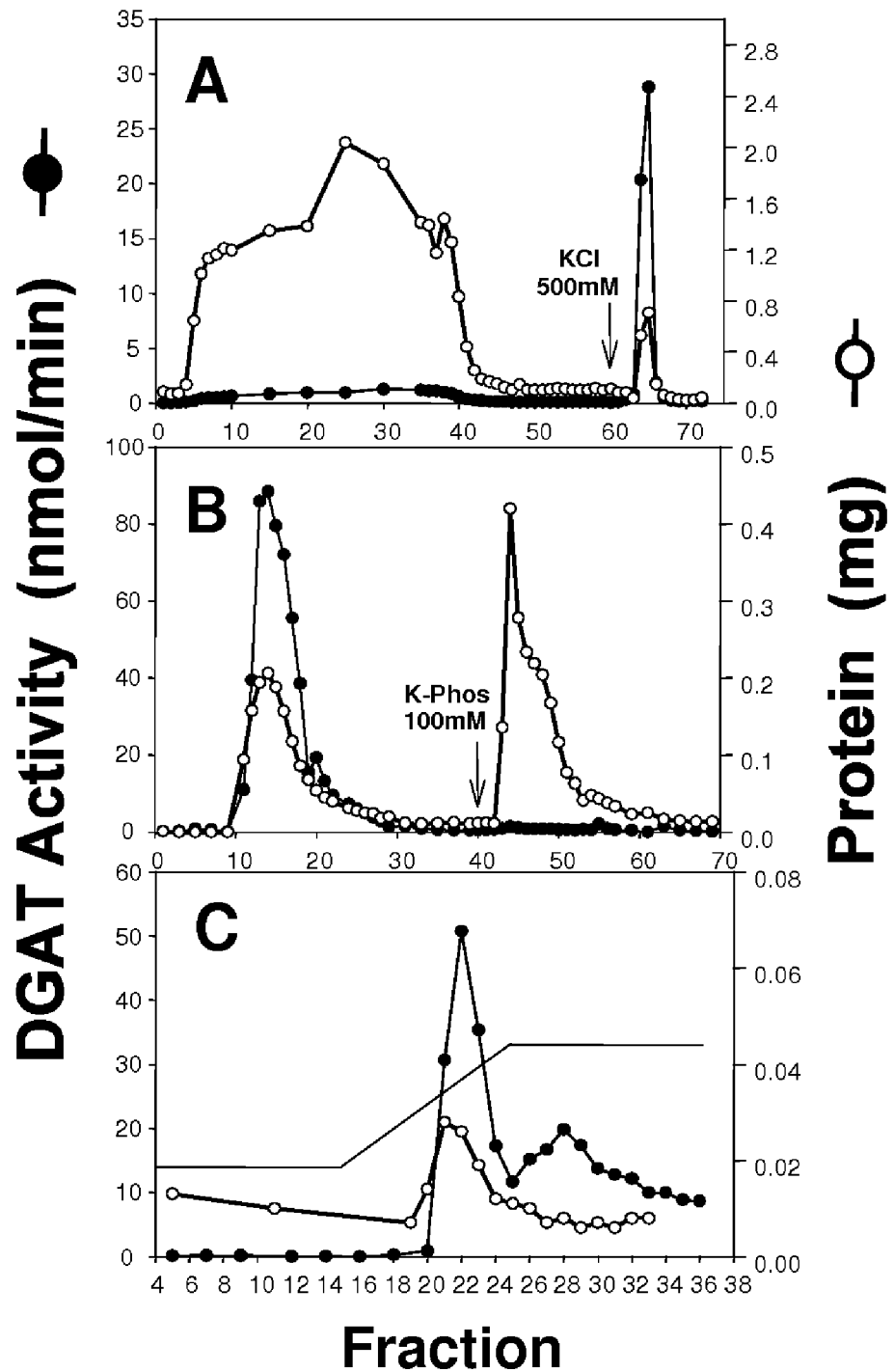
FIG. 17 shows the chromatographic enrichment of *M. ramanniana* DGAT2 activity.
Figure 18:
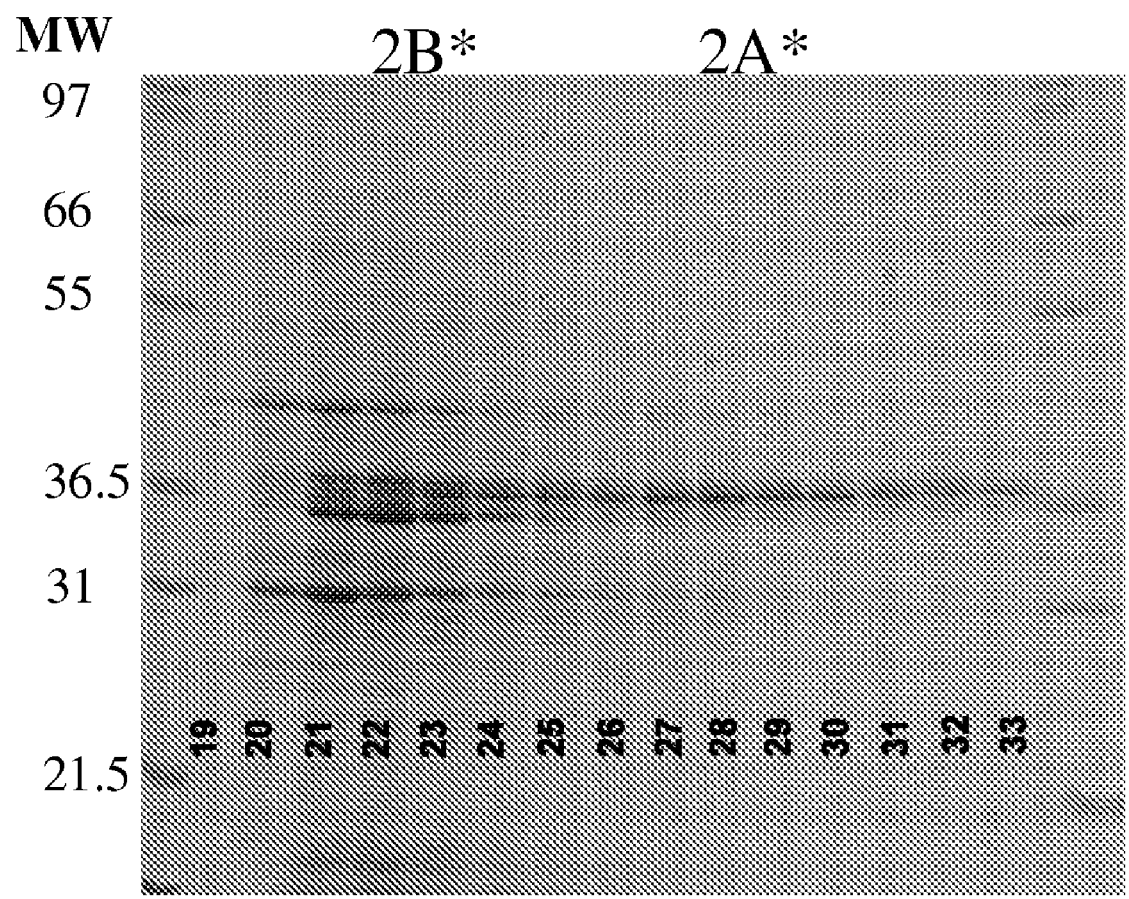
FIG. 18 shows SDS-PAGE of the Heparin column fractions. Proteins present in fractions from the Heparin column are separated by SDS-PAGE. Electrophoresis is carried out on a 20×20 cm gel containing a 10-13% acrylamide gradient and the gel is stained with Coomassie Blue. The stars indicate the location of the two peaks of DGATB activity.

A summary of the purification of the two proteins from M. ramanniana is presented in Table 3. Initial steps include homogenization of the fungal paste, isolation of the lipid bodies by centrifugation, and solubilization of the membrane-bound proteins using the detergent Triton X-100. In the early stages of purification, high salt and detergent concentrations are necessary to maintain the solubility of the hydrophobic proteins. Enzyme activity is stable through the first column, Yellow-86 Agarose (FIG. 17A), but is rapidly lost during subsequent purification. For that reason, scale-up occurs by pooling and concentrating the eluted fractions from four Yellow 86-Agarose preparations. In order to maintain maximal activity, subsequent chromatography is performed and fractions are assayed on the same day. Significant purification is achieved using hydroxyapatite (HA) chromatography (FIG. 17B). While DGAT activity does not bind the column, 64% of the protein present does bind to the column and is removed. Active fractions from the flow-through of the HA column are purified on Heparin-CL 6B agarose (FIG. 17C). Two activity peaks are eluted from the heparin column, one during the 100-500 mM KCL wash. Several protein bands (36.5 kD, 36 kD, 35 kD, and 34 kD) are associated with the first peak of activity (FIG. 18, fxn 22). The 34 kD band does not correlate with DGAT activity in all chromatographic steps, so it is eliminated. The second peak has a higher specific activity (Table 3) and contains a major protein band at 36 kD by SDS-PAGE (FIG. 18, fxn 28). Three proteins (36.5 kD, 36 kD, and 35 kD) are identified from the purification as potential DGAT candidates.

TABLE 3*

| Fraction | Protein (mg) | Activity (nmol/min) | Specific Act. (nmol/min/mg) | Fold Purification | Recovery (%) |
|---|---|---|---|---|---|
| 1500 g | 2341.2 | 1218.0 | 0.5 | 1.0 | 100 |
| Tx-100 extract | 117.6 | 2069.2 | 17.6 | 33.8 | 169.8 |
| Yellow load | 63.6 | 1458.8 | 22.9 | 44.1 | 119.7 |
| Yellow Ft/wash | nd | 719.2 | nd | nd | 59.0 |
| Yellow eluted | 1.6 | 678.0 | 440.3 | 846.2 | 55.7 |
| HA pool | 0.56 | 340.2 | 607.6 | 1167.6 | 27.9 |
| Heparin eluted | 0.20 | 264.6 | 1323.0 | 2646.0 | 21.7 |
| Heparin fxn 22 | 0.0026 | 51.0 | 1961.5 | 3769.5 | 4.2 |
| Heparin fxn 28 | 0.0076 | 20.0 | 2631.6 | 5057.2 | 1.6 |

*Purification scheme for DGAT2. A lipid body fraction isolated from 300 g of M. ramanniana cell paste are used for the preparation. Recovery values for Mr-DGAT2A (Heparin fxn 28) and Mr-DGAT2B (Heparin fxn 22) are reported separately in the last chromatographic step.

Three proteins associated with DGAT activity are gel purified by SDS-PAGE, stained with Coomassie Blue, then excised for protein sequencing. In-gel digestion of the proteins is performed using trypsin and peptides are purified using reversed-phase HPLC. Examination of the peptide maps reveals that the 36.5 kD map and the 35 kD map are identical. Only the peptides from the 36.5 kD band are sequenced. A peptide map of the 36 kD protein is different than that of the 36.5/35 kD proteins and several of these peptides are sequenced.

Degenerate primers (FIG. 19), designated from the amino acid sequences generated from the 36 kD peptide, are constructed in both sense and antisense orientations. These primers are employed in different combinations to amplify cDNA produced from *M. ramanniana* total RNA. PCR products are cloned into pCR2.1 TOPO and analyzed by DNA sequencing. Comparisons between peptide sequences obtained by Edman degradation not used to design the primers and the deduced amino acid sequences of PCR products are used to confirm the identity of the fragments. RACE using primers specific to these fragments is performed to yield a 1312 base pair (bp) long cDNA. This cDNA, designated DGAT2A (accession #AF391089), contains a large open reading frame starting at bp 15. The most 5' ATG codon of this reading frame is located at bp 76, allowing for the translation of a polypeptide of 355 amino acids in length (FIG. 19, DGAT2A) (Patent Appln. No. WO 00/01713 (herein incorporated by reference)).

A similar strategy is employed to clone the cDNA encoding the 36.5 kD protein. Similarities are observed between peptide sequences obtained from the 36 kD and 36.5 kD polypeptides. Therefore, degenerate oligonucleotide primers are designed to the sequences of the 36.5 kD peptide, which has the least homology to the 36 kD protein (FIG. 19). Evolutionary PCR, combined with RACE, using primers specific to these fragments is performed to yield a 1177 bp long cDNA. This cDNA, which was designated DGAT2B (accession #AF391090), contains a single large open reading frame from the 5' end to bp 1131. The most 5' ATG codon of this reading frame is located at position 84, which allows for the translation of a 349 amino acid polypeptide (FIG. 19, DGAT2B) (Patent Appln. No. WO 00/01713, herein incorporated by reference). Both designated MrDGAT2 ATG codons are followed by a G residue, the consensus nucleotide for initiation of translation in eukaryotes at this position.

The DGAT2A cDNA encodes a polypeptide of a calculated molecular mass of 40,602.5 Da, and a theoretical pI value of 9.18. The DGAT2B cDNA encodes a polypeptide with a calculated molecular mass of 39595.49 Da, and a theoretical pI value of 9.40. These predicted molecular weights fit very well with the apparent molecular weight (MW) of the purified proteins, which indicates that DGAT2 polypeptides do not undergo major post-translational proteolytic processing in vivo. The two polypeptides share 54% identity at the protein level (FIG. 19, top two sequences).

Genbank searches showed that these polypeptides are not sequence-related to the known DGAT1 or any other acyl transferases, but were members of a previously unannotated gene family present in major phyla of eukaryotes, in particular fungi, plants, animal and basal eukaryotes (FIG. 19). An alignment of members from different major eukaryotic phyla shows that these sequences are approximately conserved in length and they co-align over large stretches, with about 10% of totally conserved residues dispersed throughout. A preliminary phylogenic tree (FIG. 20), constructed from currently available sequences, shows clustering of sequences by systematic relationship of species indicating that DGAT2 gene variations, as found in *Mortierella, C. elegans* and mammals, appear to be the result of relatively late gene duplications, having occurred after the divergence of the respective main branches of eukaryotes.

Figure 21:
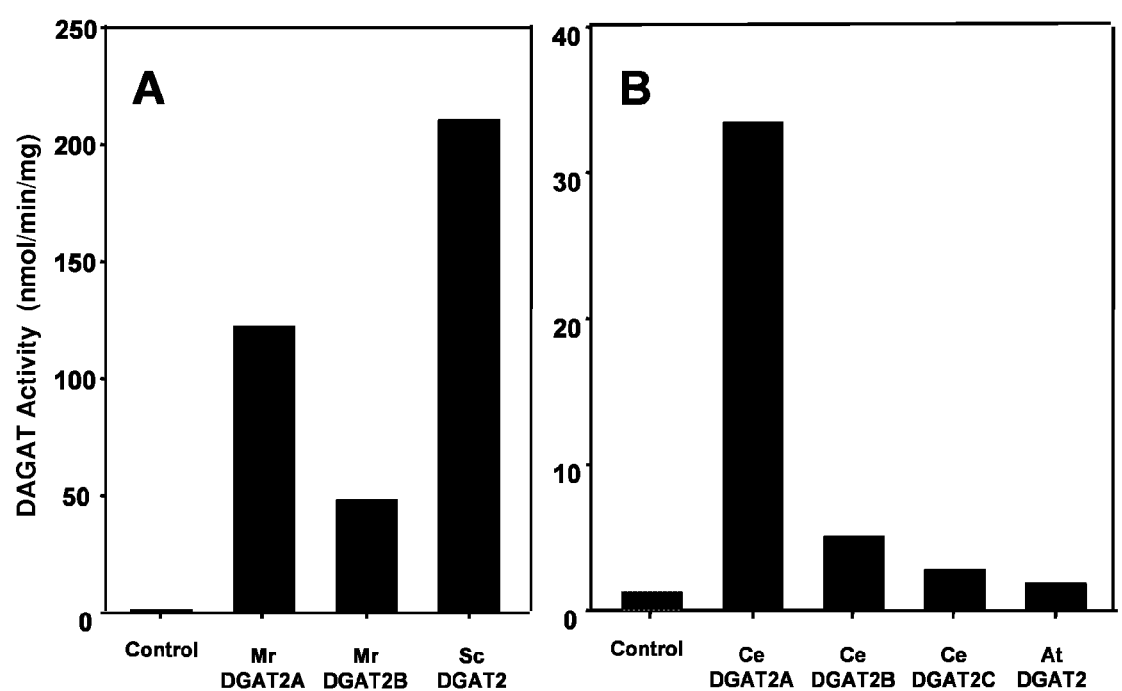
FIG. 21 shows DGAT activity in insect cells expressing selected DGAT2 genes. Activity is expressed as the nanomoles of TAG produced per minute per milligram of membrane protein. Data is not normalized for the amount of gene product produced.

Two DGAT genes identified in *M. ramanniana* are expressed in an insect cell system to confirm that they encode polypeptides with DGAT activity. Membranes from baculovirus-infected insect cells expressing DGAT2 cDNAs are harvested and assayed for activity. An elevation in DGAT activity is detected relative to untransformed sf9 cells for both DGAT2A and DGAT2B proteins of 94 and 37 fold, respectively (FIG. 21*a*).

Full-length clones are obtained for several of the genes whose sequences show homology to the *M. ramanniana* DGAT2 genes. These genes (*S. cerevisiae* DGAT2; *C. elegans* DGAT2A, DGAT2B, and DGAT2C; and *Arabidopsis thaliana* DGAT2) are selected from different phyla to test the relatedness of protein function. The cDNAs are expressed in insect cells and the isolated membranes are assayed for DGAT activity. A 2-180 fold increase in DGAT activity is observed, relative to untransformed sf9 cells, confirming that these genes encode proteins which are related by function (FIGS. 21*a* and 21*b*).

In addition to the observed increase in DGAT activity, a 2.7 fold increase is detected in the amount of TAG present in insect cells expressing the *M. ramanniana* DGAT2A gene relative to untransformed sf9 cells. When the samples are normalized with respect to phospholipid content, the TAG production is increased by 3.1 fold. Thus, results of the triacylglycerol analysis demonstrate that overexpression of the *M. ramanniana* DGAT2A gene leads to an increase in the production of triacylglycerols in insect cells.

Figure 22:
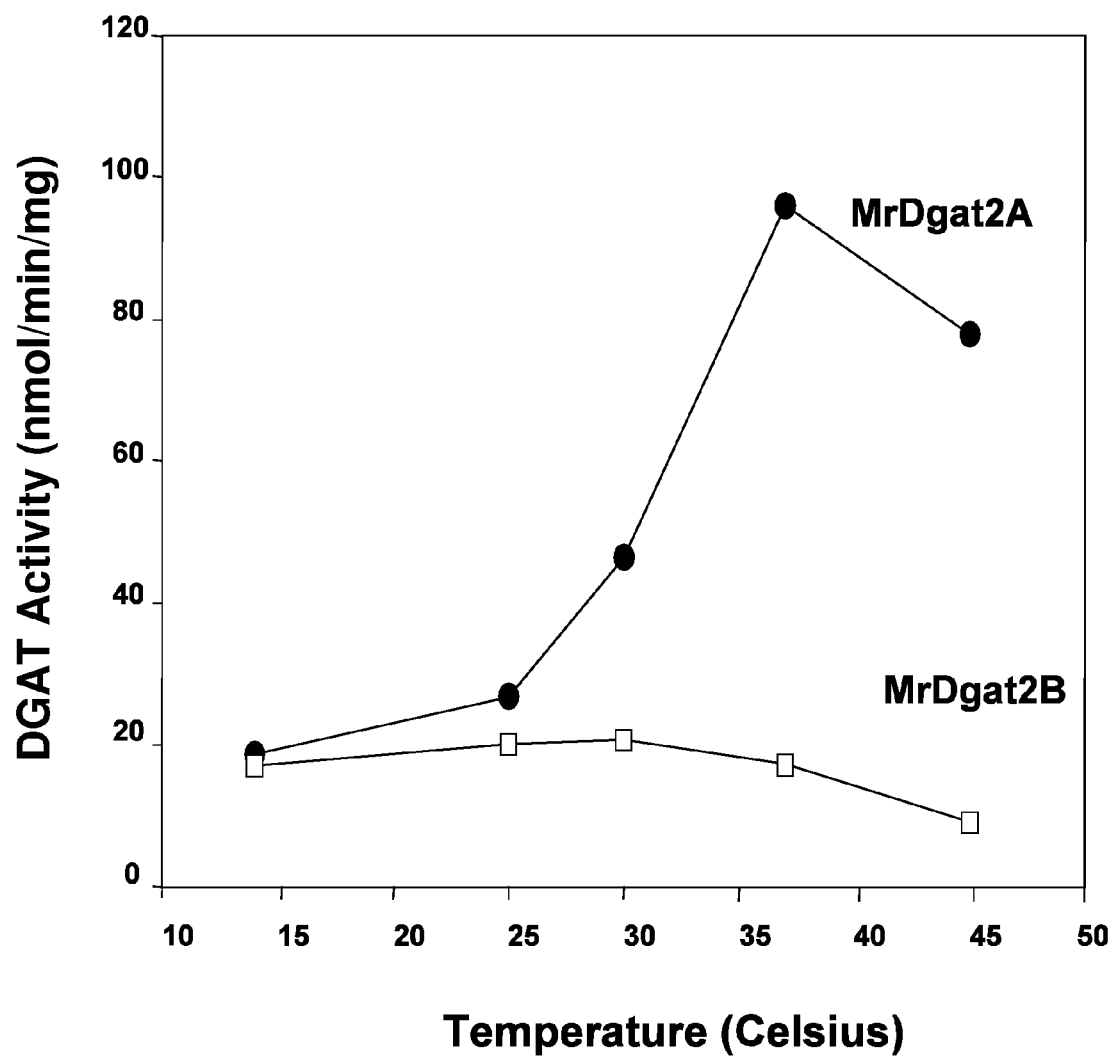
FIG. 22 shows the effect of temperature on MrDGAT2A and MrDGAT2B activity in insect cell membranes.

Enzymological properties of the expressed *M. ramanniana* DGAT2A and DGAT2B genes are also investigated. The effect of pH on DGAT activity is evaluated over a range of 4.0 to 11.0. The pH optimum for both enzymes is observed at 6.8. No differences are detected between the two polypeptides with respect to pH. A difference is observed in their response to temperature. The temperature optimum for DGAT2A is 37° C. whereas DGAT2B does not demonstrate an optimum temperature (FIG. 22). The polypeptides are also characterized with respect to their ability to utilize two different acyl-coenzyme A donors, 18:1 and 12:0, and a range of diacylglycerol acceptors (6:0 through 18:0, even numbers, and 18:1) (FIGS. 23*a* and 23*b*). An enhanced capacity for the utilization of medium-chain substrates (6:0 to 10:0) is detected for both DGAT2A and DGAT2B proteins.

Example 18

Expression of DGAT2 in Insect Cells

Two proteins exhibiting DGAT activity are purified to near homogeneity from the fungus *M. ramanniana*. Genbank searches showed that these polypeptides are not sequence-related to the previously identified diacylglycerol acyltransferase gene family (DGAT1) or any other acyltransferase, but are members of a gene family present in all eukaryotes (DGAT2).

Several DGAT2 *M. ramanniana* (MrDGAT2A); *S. cerevisiae* (SCYOR245c), and *C. elegans* (CEK07B1.4, CEF59A1.10, and CEWOLA112) are cloned and expressed in insect cells. Membranes from the insect cells are harvested and assayed for DGAT activity. All tested exhibited an increase in DGAT activity relative to the untransformed control cells. The assay results are described in Example 15A and the results are illustrated in FIG. 15.

Additional genes are cloned and tested (*M. ramanniana* DGAT2B and *A. thaliana* DGAT2). FIG. 19 shows the derived amino acid sequences at lines 2 and 7, respectively. These genes are then expressed in insect cells. Membranes isolated from the cells expressing MrDGAT2B and those expressing *A. thaliana* DGAT2 exhibited a 71 fold and 2.2 fold increase, respectively, in DGAT activity relative to untransformed cells (FIG. 2; panel A, lane 3 and panel B, lane 5).

The level of sequence homology among the DGAT2 members across species is low (only 10% of the residues are totally conserved and dispersed throughout the polypeptide).

Figure 24:
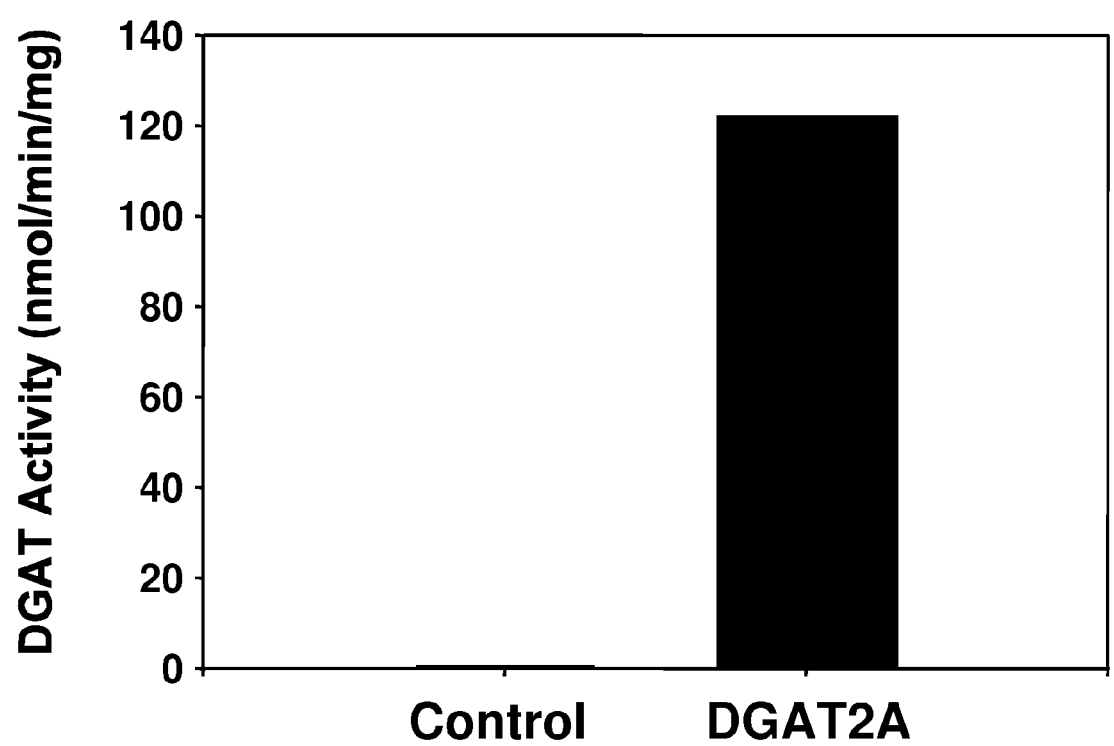
FIG. 24 shows DGAT activity assay results for DGAT2A in insect cell membranes.

When *M. ramanniana* DGAT2A (SEQ ID NO: 99) is expressed in insect cells, the amount of TAG that accumulated in these cells increased approximately 3 fold. (Example 16 and FIG. 16.) *M. ramanniana* DGAT2A was resynthesized in order to optimize codon usage according to the preferences in plants. The resynthesized gene, DGAT2A (SEQ ID NO: 99), encodes the same protein as the unresynthesized gene. Activity of the resynthesized gene in insect cells was confirmed. A 180 fold increase in DGAT activity was detected relative to untransformed cells (FIG. 24).

Example 19

Expression of DGAT2 in Plants

A resynthesized *M. ramanniana* DGAT2A gene (SEQ ID NO: 99) is expressed in soybean under control of 7S regulatory sequences. Plants are transformed by particle bombardment and enzyme assays are performed on pooled, developing $R_1$ seed. Several plants exhibited significant (5-20 fold) increases in DGAT activity relative to untransformed plants and shown in FIG. 23.

$R_1$ seed from plants expressing the resynthesized *M. ramanniana* DGAT2A gene are advanced to the next generation ($R_2$). Oil and protein levels are determined by Near-Infra-Red (NIR) analysis of mature $R_2$ seed. A statistically significant increase in oil levels is observed in seeds expressing the transgene, relative to those that do not contain the transgene (nulls) while a statistical evaluation of the protein data shows that it is unchanged, as shown in FIGS. 25 and 26. This data illustrates the modification of the triacylglycerol composition in a plant cell (i.e., oil is increased relative to other plant components, for example, protein).

Example 20

Analysis of Medium-Chain Triglyceride Production by DGAT2

Figure 23:
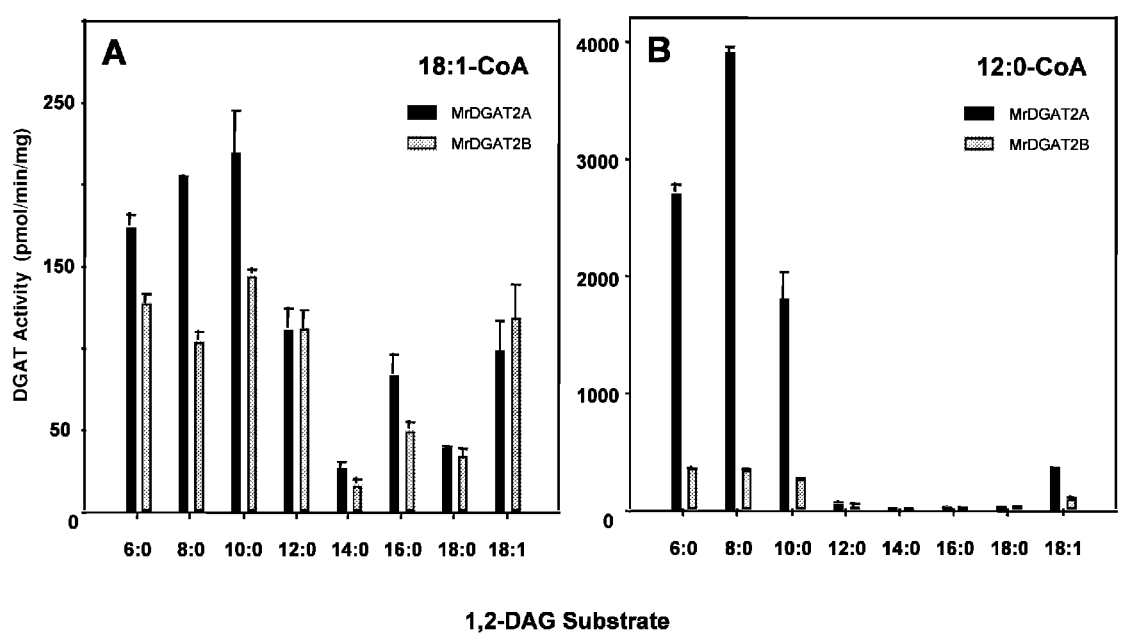
FIG. 23 shows DGAT2 substrate specificity profiles. Substrate profiles were obtained for DGAT2A and DGAT2B in insect cell membranes. Substrate specificity was determined with 18:1-CoA as acyl donor (FIG. 23A) and 12:0-CoA as acyl donor (FIG. 23B) using a range (6:0-18:1) of DAG acceptors.

An ability of *M. ramanniana* DGAT2A and DGAT2B to utilize a range of acyl-donors (C6 to C18 and C18:1 acyl-Coenzyme A's) and acyl acceptors (C6 to C18 and C18:1 1,2-DAG's) as substrates is evaluated in a DGAT assay. Insect cell membranes expressing either *M. ramanniana* DGAT2A or DGAT2B are used for the analysis. *M. ramanniana* DGAT2A is preferably able to utilize medium-chain (C6-C10) substrates compared to *M. ramanniana* DGAT2B, producing more than 1000 pmol/min/mgs of medium-chain triglyceride (FIG. 23).

Figure 27:
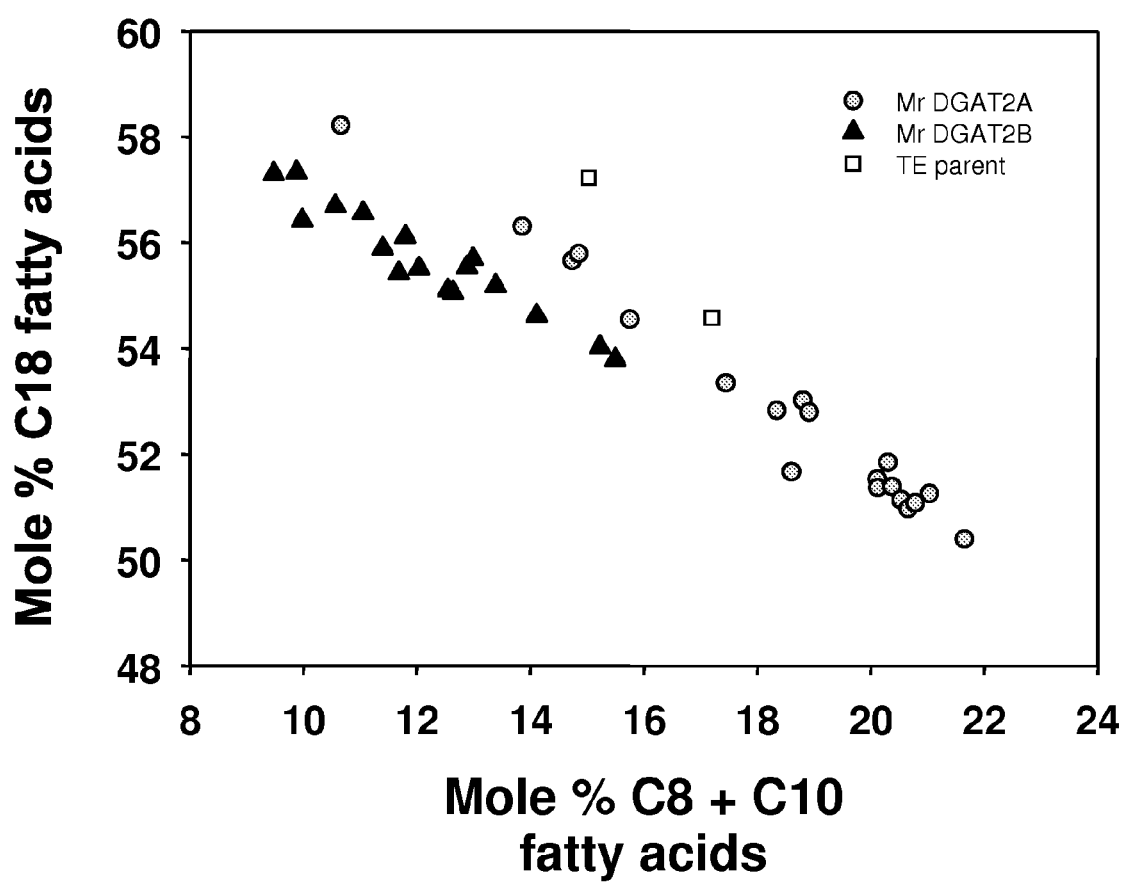
FIG. 27 shows mole percent C8+C10 fatty acids in *Arabidopsis* seed expressing DGAT2A (Mr-1R)+TE compared with the TE parent alone, or TE in combination with *Cuphea hookeriana* LPAAT (lysophosphatidic acid acyltransferase). Data is presented with respect to the conservation of 18C fatty acids to the shorter chain species.

A plasmid (pCGN8829) containing a DGAT2A (SEQ ID NO: 99) gene under control of napin regulatory sequences, is used to transform an *Arabidopsis* plant that was homozygous for *Cuphea hookeriana* thioesterase gene, FatB2. The introduced thioesterase gene alters the fatty acid composition of the triacyglycerol fraction, producing up to 17 mole % C8+C10 fatty acids in the seed oil (up from less than 0.1%). Fatty acid analysis of the mature seed revealed a 30% increase in medium-chain fatty acids in plants expressing both *M. ramanniana* DGAT2A and *Cuphea hookeriana* FatB2 relative to those expressing *Cuphea hookeriana* FatB2 alone or to those expressing *Cuphea hookeriana* FatB2 in combination with *Cuphea hookeriana* lysophosphatidic acid acyltransferase (LPAAT) which may enable medium-chain fatty acids to enter the sn-2 position of the glycerol molecule (FIG. 27).

Figure 28:
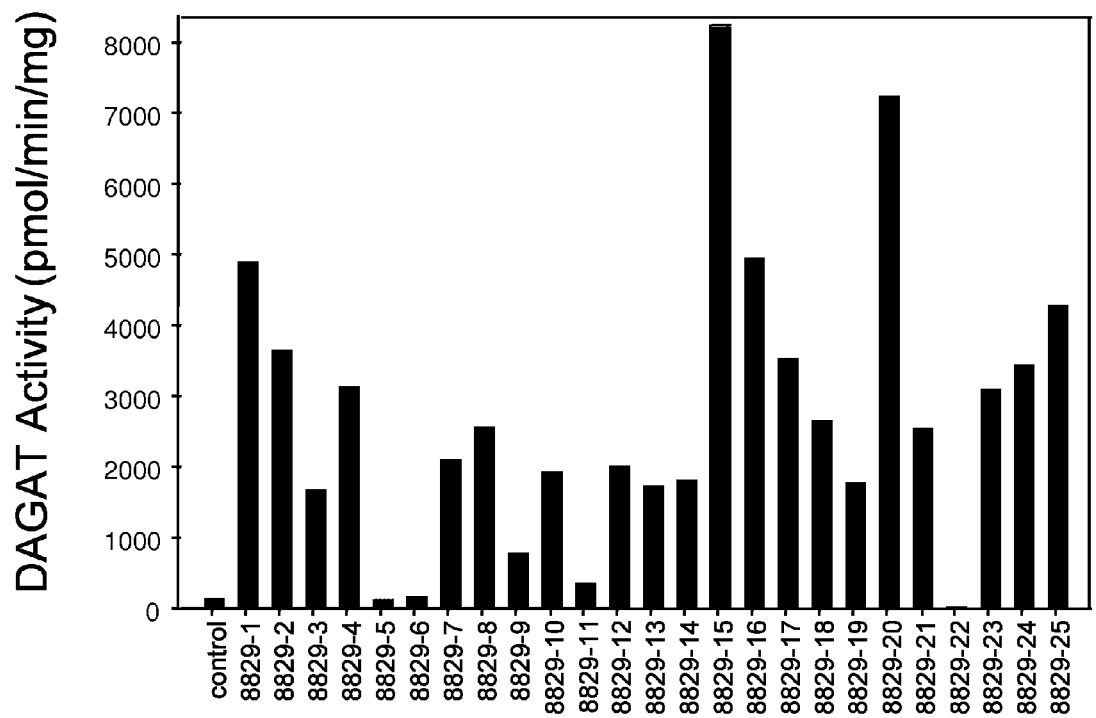
FIG. 28 shows DGAT activity assay results in developing $R_1$ canola seed.
Figure 29:
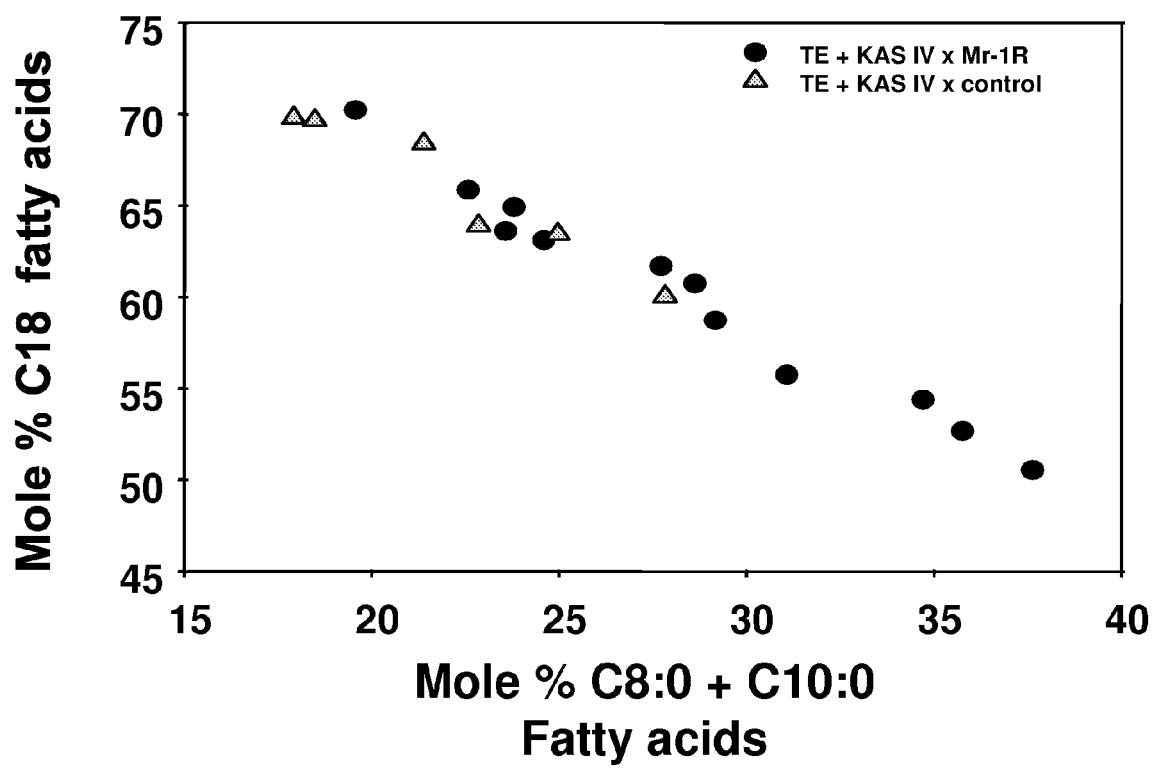
FIG. 29 shows mole percent C8+C10 fatty acids in canola seed expressing DGAT2A crossed to canola expressing pCGN4807/5401 (*Cuphea hookeriana* thioesterase (TE) and β-ketoacyl-ACP synthase IV (KAS IV) genes) compared to pCGN4807/5401 crossed with a canola control. Data is presented with respect to the conversion of 18C fatty acids to the shorter claim species.

The effect of *M. ramanniana* DGAT2A on medium-chain production is also analyzed in Canola (rapeseed). Canola is transformed with pCGN8829 using *Agrobacterium* infection and enzyme assays are performed on pooled, developing $R_1$ seed. Several plants exhibited significant (12-67 fold) increases in DGAT activity relative to untransformed plants (FIG. 28). Canola plants with the highest DGAT activity are crossed with plants expressing two genes from *Cuphea hookeriana* that contribute to medium-chain production, the FatB2 gene (pCGN4804) and the KAS IV gene (pCGN5401). As a control, plants expressing pCGN4804/5401 are also crossed with non-transgenic canola. The $F_1$ progeny are segregating with respect to all genes so plants are advanced another generation. $F_2$ plants are self-pollinated and $F_3$ seed are evaluated for mole % C8+C10 fatty acid. A 35% increase in medium-chain fatty acids is detected in the $F_2$ progeny if the pCGN4804/5401xpCGN8829 cross relative to the cross between CGN4804/5401 X non-transgenic canola (FIG. 29).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. An isolated polynucleotide that encodes a polypeptide with diacylglycerol acyltransferase activity and is selected from the group consisting of:
   a) an isolated polynucleotide comprising SEQ ID NO: 37;
   b) an isolated polynucleotide comprising a nucleotide sequence which has at least 70% identity to that of SEQ ID NO: 37 over the entire length of SEQ ID NO: 37;
   c) an isolated polynucleotide that hybridizes, under stringent conditions, to SEQ ID NO: 37 or a fragment thereof;
   d) an isolated polynucleotide comprising a nucleotide sequence which has at least 70% identity to that of SEQ ID NO: 84 over the entire length of SEQ ID NO: 84;
   e) an isolated polynucleotide that hybridizes, under stringent conditions, to SEQ ID NO: 84 or a fragment thereof; and
   f) an isolated polynucleotide complementary to the polynucleotide sequence of (a), (b), (c), (d), or (e).

2. A nucleic acid construct comprising as operably linked components in the 5' to 3' direction of transcription:
   a transcriptional initiation region; and
   the isolated polynucleotide sequence of claim 1 encoding said polypeptide with diacylglycerol acyltransferase activity.

3. A host cell comprising the nucleic acid construct according to claim 2.

4. The host cell of claim 3, wherein said host cell is selected from the group consisting of bacterial, insect, fungal, mammalian, and plant.

5. A plant comprising the cell of claim 4.

6. The plant of claim 5, wherein the plant is selected from the group consisting of corn, rapeseed, sunflower, safflower, cotton, soybean, peanut, coconut and oil palm.

7. A plant cell comprising the construct of claim 2.

8. The plant cell of claim 7, wherein the plant cell is from a plant selected from the group consisting of corn, rapeseed, sunflower, safflower, cotton, soybean, peanut, coconut and oil palm.

9. The plant cell of claim 8, wherein the plant cell is a corn cell.

10. A plant comprising the construct of claim 2.

11. The plant of claim 10, wherein the plant is of a plant species selected from the group consisting of corn, rapeseed, sunflower, safflower, cotton, soybean, peanut, coconut and oil palm.

12. The plant of claim 10, wherein the plant is a corn plant.

13. The isolated polynucleotide of claim 1, comprising a nucleotide sequence which has at least 80% identity to that of SEQ ID NO: 37 over the entire length of SEQ ID NO: 37.

14. The isolated polynucleotide of claim 1, comprising a nucleotide sequence which has at least 90% identity to that of SEQ ID NO: 37 over the entire length of SEQ ID NO: 37.

15. The isolated polynucleotide of claim 1, comprising a nucleotide sequence which has at least 95% identity to that of SEQ ID NO: 37 over the entire length of SEQ ID NO: 37.

16. The isolated polynucleotide of claim 1, comprising a nucleotide sequence which has at least 97% identity to that of SEQ ID NO: 37 over the entire length of SEQ ID NO: 37.

17. The isolated polynucleotide of claim 1, comprising a nucleotide sequence which has at least 80% identity to that of SEQ ID NO: 84 over the entire length of SEQ ID NO: 84.

18. The isolated polynucleotide of claim 1, comprising a nucleotide sequence which has at least 90% identity to that of SEQ ID NO: 84 over the entire length of SEQ ID NO: 84.

19. The isolated polynucleotide of claim 1, comprising a nucleotide sequence which has at least 95% identity to that of SEQ ID NO: 84 over the entire length of SEQ ID NO: 84.

20. The isolated polynucleotide of claim 1, comprising a nucleotide sequence which has at least 97% identity to that of SEQ ID NO: 84 over the entire length of SEQ ID NO: 84.

21. The isolated polynucleotide of claim 1, wherein the polypeptide with diacylglycerol acyltransferase activity comprises the following amino acids at a position equivalent to the following positions of SEQ ID NO: 37: Y103, F104, P105, Y120, P126, H127, F163, R169, G176, L189, V201, G203, G204, E207, L220, R223, G225, F226, A230, G234, L237, V238, P239, F243, G244, F284, P292, G302, P304, I305, V307, Y327.

* * * * *